United States Patent
Johnson et al.

(10) Patent No.: US 9,962,531 B2
(45) Date of Patent: May 8, 2018

(54) INFLATOR FOR DILATION OF ANATOMICAL PASSAGEWAY

(71) Applicant: Acclarent, Inc., Menlo Park, CA (US)

(72) Inventors: Gregory W. Johnson, Milford, OH (US); Emron J. Henry, Cincinnati, OH (US); Jeffrey S. Swayze, Hamilton, OH (US); Cory G. Kimball, Cincinnati, OH (US); Kenneth E. Carper, Cincinnati, OH (US); Daniel L. Geiger, Ft. Thomas, KY (US); Kyle A. Lehr, Cincinnati, OH (US)

(73) Assignee: ACCLARENT, INC., Irvine, CA (US)

( * ) Notice: Subject to any disclaimer, the term of this patent is extended or adjusted under 35 U.S.C. 154(b) by 659 days.

(21) Appl. No.: 13/837,577

(22) Filed: Mar. 15, 2013

(65) Prior Publication Data
US 2014/0074140 A1   Mar. 13, 2014

Related U.S. Application Data

(60) Provisional application No. 61/725,523, filed on Nov. 13, 2012, provisional application No. 61/698,788, filed on Sep. 10, 2012.

(51) Int. Cl.
*A61M 29/00* (2006.01)
*A61M 29/02* (2006.01)
(Continued)

(52) U.S. Cl.
CPC ............. *A61M 29/02* (2013.01); *A61B 17/24* (2013.01); *A61M 5/31586* (2013.01);
(Continued)

(58) Field of Classification Search
CPC ........ A61M 25/10182; A61M 5/31586; A61M 2025/1022; A61M 5/31501;
(Continued)

(56) References Cited

U.S. PATENT DOCUMENTS 4,655,749 A   4/1987   Fischione
4,723,938 A   2/1988   Goodin et al.
(Continued)

FOREIGN PATENT DOCUMENTS

JP   2008-099917 A   5/2008
WO   WO 92/006735   4/1992
(Continued)

OTHER PUBLICATIONS

Design U.S. Appl. No. 29/466,466, filed Sep. 9, 2013.
(Continued)

*Primary Examiner* — Jonathan Miles
*Assistant Examiner* — Majid Jamialahmadi
(74) *Attorney, Agent, or Firm* — Frost Brown Todd LLC

(57) ABSTRACT

A dilation catheter system is provided to dilate the ostium of a paranasal sinus; or to dilate some other anatomical passageway (e.g., within the ear, nose, or throat, etc.). The dilation catheter system may include a dilation catheter, a dilator, a guide catheter, and an inflator. The dilation catheter may be positioned between the dilator and the inflator. The guide catheter may be inserted within the affected passageway to allow the dilator to be positioned through the guide catheter and into the affected passageway. The inflator may then be actuated to transfer fluid from the inflator, through the dilation catheter, and into the dilator. The transfer of fluid may inflate the dilator to an expanded state to open or dilate the affected passageway.

4 Claims, 33 Drawing Sheets

(51) Int. Cl.
*A61B 17/24* (2006.01)
*A61M 5/315* (2006.01)
*A61M 25/10* (2013.01)
A61M 25/01 (2006.01)
A61M 25/00 (2006.01)
A61M 25/09 (2006.01)

(52) U.S. Cl.
CPC ... *A61M 25/10182* (2013.11); *A61M 25/0108* (2013.01); *A61M 2025/0046* (2013.01); *A61M 2025/09125* (2013.01)

(58) Field of Classification Search
CPC .......... A61M 2005/31508; A61M 2005/3131; A61M 25/10181; A61M 25/10184; A61M 2005/2073; A61M 5/31528; A61M 5/31548
USPC .... 606/192, 92–94; 604/194, 220, 208, 210, 604/211; 222/153.01, 153.02, 153.03, 222/153.13; 401/176–182, 171, 172
See application file for complete search history.

(56) References Cited

U.S. PATENT DOCUMENTS

| 4,919,121 | A | | 4/1990 | Rydell et al. |
| 5,213,115 | A | | 5/1993 | Zytkovicz et al. |
| 5,242,430 | A | * | 9/1993 | Arenas et al. ............... 16/110.1 |
| 5,279,563 | A | * | 1/1994 | Brucker ............ A61M 25/1018 604/100.03 |
| 5,324,265 | A | * | 6/1994 | Murray ............... A61M 5/3234 604/110 |
| 5,743,889 | A | * | 4/1998 | Sams ................ A61M 5/31551 604/207 |
| 7,207,971 | B2 | | 4/2007 | Hart et al. |
| 7,630,676 | B2 | | 12/2009 | Pirwitz |
| 7,654,997 | B2 | | 2/2010 | Makower et al. |
| 7,803,150 | B2 | | 9/2010 | Chang et al. |
| 7,959,607 | B2 | | 6/2011 | Smit et al. |
| D746,977 | S | | 1/2016 | Johnson et al. |
| 2002/0165497 | A1 | * | 11/2002 | Greene ......................... 604/198 |
| 2006/0004323 | A1 | | 1/2006 | Chang et al. |
| 2007/0129751 | A1 | | 6/2007 | Muni et al. |
| 2007/0208301 | A1 | | 9/2007 | Evard et al. |
| 2008/0183128 | A1 | | 7/2008 | Morriss et al. |
| 2010/0030031 | A1 | | 2/2010 | Goldfarb et al. |
| 2011/0004057 | A1 | | 1/2011 | Goldfarb et al. |
| 2012/0078118 | A1 | | 3/2012 | Jenkins et al. |

FOREIGN PATENT DOCUMENTS

| WO | WO 94/015120 | 7/1994 |
| WO | WO 97/044077 | 11/1997 |
| WO | WO 2006/130491 | 12/2006 |

OTHER PUBLICATIONS

U.S. Appl. No. 14/020,924, filed Sep. 9, 2013.
U.S. Appl. No. 61/698,788, filed Sep. 10, 2012.
U.S. Appl. No. 61/725,523, filed Nov. 13, 2012.
European Search Report dated Apr. 4, 2014 re Application No. 13 762 706.3.
International Preliminary Report on Patentability dated Mar. 10, 2015 re Application No. PCT/US2013/058702.
International Preliminary Report on Patentability dated Dec. 2, 2013 re Application No. PCT/US2013/058699.
Chinese Office Action, First Office Action, dated Sep. 5, 2016 for Application No. CN 201380058551.7, 5 pgs.
Chinese Search Report, First Search, dated Aug. 24, 2016 for Application No. CN 201380058551.7, 3 pgs.
International Search Report and Written Opinion dated Dec. 2, 2013 re Application No. PCT/US2013/058702, 14 pgs.
International Preliminary Report on Patentability dated Mar. 10, 2015 re Application No. PCT/US2013/058699, 7 pgs.
Japanese Office Action, Notification of Reasons for Refusal, dated Aug. 1, 2017 for Application No. JP 2015-531274, 5 pgs.

* cited by examiner

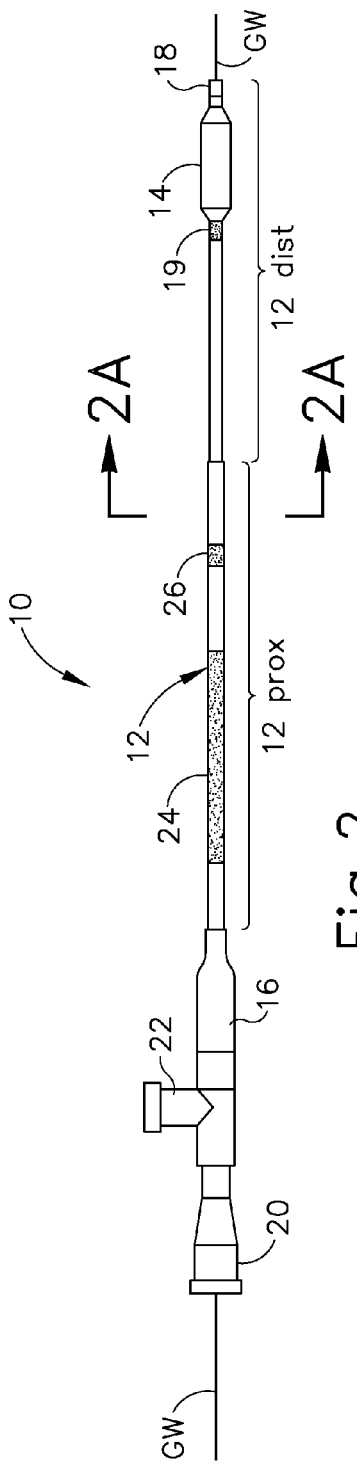
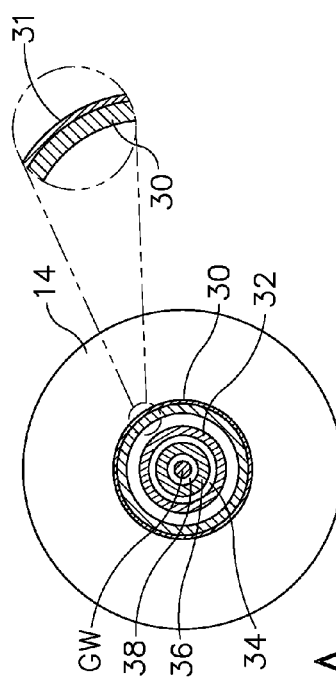
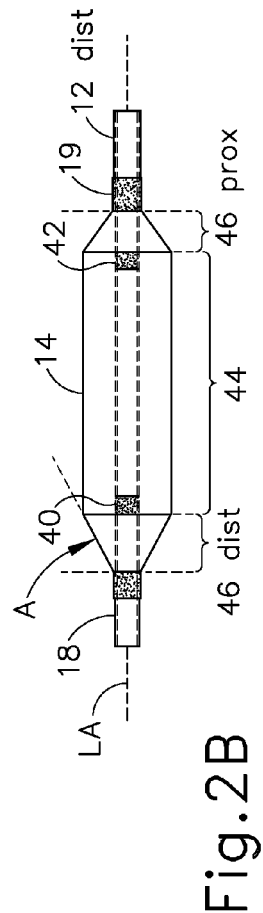
Fig. 2
Fig. 2A
Fig. 2B

INFLATOR FOR DILATION OF ANATOMICAL PASSAGEWAY

PRIORITY

This application claims priority to U.S. Provisional Pat. App. No. 61/725,523, entitled "Inflator for Dilation of Anatomical Passageway," filed Nov. 13, 2012, the disclosure of which is incorporated by reference herein.

This application also claims priority to U.S. Provisional Pat. App. No. 61/698,788, entitled "Inflator for Dilation of Anatomical Passageway," filed Sep. 10, 2012, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, the disclosure of which is incorporated by reference herein. An example of such an illuminating guidewire is the Relieva Luma Sentry™ Sinus Illumination System by Acclarent, Inc. of Menlo Park, Calif.

It may be desirable to provide easily controlled inflation/deflation of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 2 depicts a side view of the dilation catheter of FIG. 1, with the dilator in an expanded configuration;

FIG. 2A depicts a cross sectional view through line 2A-2A of FIG. 2 with an enlarged break-out view of a portion thereof;

FIG. 2B depicts an enlarged side view of the dilator of FIG. 1;

Figure 1:
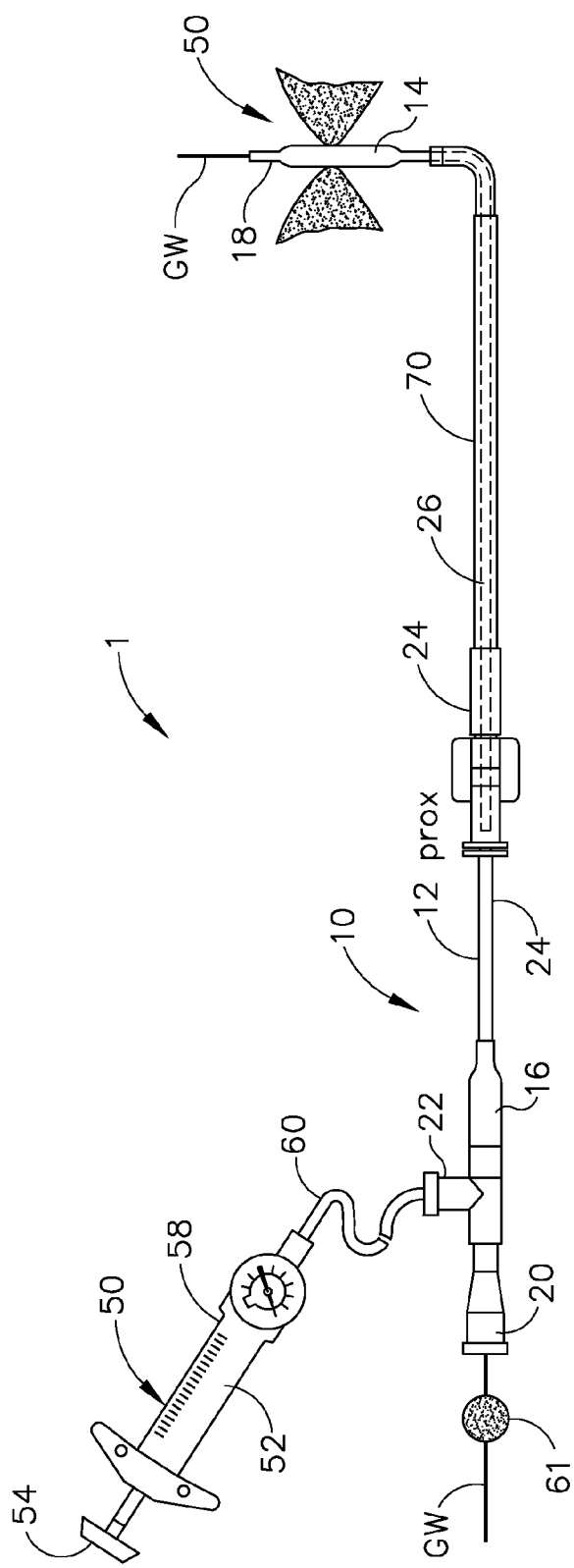
FIG. 1 depicts a side view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (1), which may be used to dilate the ostium of a paranasal sinus; or to dilate some other anatomical passageway (e.g., within the ear, nose, or throat, etc.). Dilation catheter system (1) of this example comprises a dilation catheter (10), a dilator (14), a guide catheter (70), and an inflator (50). In some versions, at least part of system (1) is configured similar to the Relieva® Spin Balloon Sinuplasty™ System by Acclarent, Inc. of Menlo Park, Calif. Dilator (14) of the present example is coupled to a distal end of dilation catheter (10), and inflator (50) is coupled to a proximal portion of dilation catheter (10), such that dilation catheter (10) provides fluid communication between inflator (50) and dilator (14). Dilation catheter (10) is slidably positioned through guide catheter (70). In a dilation procedure, guide catheter (70) may first be positioned near the targeted anatomical passageway. A guidewire (GW) may then be advanced through guide catheter (70) and into the affected passageway. Dilation catheter (10) may be advanced over the guidewire (GW) to position dilator (14) within the targeted anatomical passageway. Inflator (50) may then be actuated to transfer fluid from inflator (50) through dilation catheter (10) and into dilator (14). The transfer of fluid expands dilator (14) to an expanded state to open or dilate the targeted anatomical passageway. The fluid may then be returned to inflator (50) such that dilator (14) is deflated. This process may be repeated to dilate several anatomical passageways.

A. Exemplary Dilation Catheter

FIGS. 2-2B show additional views of dilation catheter (10) with guidewire (GW) operatively inserted therethrough. In some versions, at least part of dilation catheter (10) is configured similar to the Relieva Ultirra™ Sinus Balloon Catheter and/or the Relieva Solo Pro™ Sinus Balloon Catheter by Acclarent, Inc. of Menlo Park, Calif. Dilation catheter (10) of the present example comprises an elongate catheter shaft (12) having a proximal shaft section (12prox) that is substantially rigid and a distal shaft section (12dist) that is more flexible than proximal shaft section (12prox). An expandable dilator (14), such as a balloon or other suitable mechanical or non-inflational dilator, is mounted on distal shaft section (12dist) and a distal tip member (18) protrudes beyond the distal end of dilator (14), as shown. A proximal "T"-hub (16) is attached to the proximal end of the proximal shaft section (12prox). This proximal "T"-hub (16) has a proximal Luer connector (20) and a side arm Luer connector (22), which has a female Luer connector that extends substantially perpendicular to the longitudinal axis of hub (16). When compared to a typical "Y"-hub, side arm Luer connector (22) of this "T"-hub (16) is further away from proximal Luer connector (20) and is oriented at a right angle to proximal Luer connector (20). Thus, tubing connected to this perpendicular side arm Luer connector (22) may be less likely to obstruct or block proximal Luer connector (20) than might otherwise occur with a typical "Y"-hub; and the operator may be less likely to confuse proximal Luer connector (20) with the Luer connector on side arm Luer connector (22). Of course, some other versions of system (1) may use a conventional "Y"-hub and/or some other component(s) instead of using "T"-hub (16).

As shown in FIG. 2A, proximal shaft section (12prox) comprises a rigid outer tube (30), a flexible middle tube (32) disposed substantially coaxially within the lumen of the rigid outer tube (30), and an inner tube (36) disposed substantially coaxially within the lumen of the middle tube (32). Outer tube (30) may be formed of stainless steel hypotube having an outer diameter of 0.076 inches and an inner diameter of 0.068 inches. As an alternative to stainless steel hypotube, outer tube (30) may be formed of rigid non-metallic material such as polyetheretherketone (PEEK) or other rigid plastics suitable for such application. Of course, any other suitable material(s) and/or dimensions may be used to form outer tube (30). Furthermore, other rigid reinforcing members may be used in, or in lieu of, outer tube (30), such as wires (e.g., round, flat, square or of other cross section), partial tubes (e.g., arcs), etc. Middle tube (32) may be formed of Pebax having an inner diameter of 0.055 inches, an outer diameter of 0.065+/−0.003 inches. Again, any other suitable material(s) and/or dimensions may be used to form middle tube (32). Inner tube (36) may be formed of polyether block copolymer tubing (e.g., Pebax® Resin, Arkema, Inc., Philadelphia, Pa.) having an inner diameter of 0.038 inches, an outer diameter of 0.048 inches. Yet again, any other suitable material(s) and/or dimensions may be used to form inner tube (36). Outer tube (30) terminates at the end of proximal shaft section (12prox). Middle tube (32) and inner tube (36) extend beyond the distal end of outer tube (30), forming distal shaft section (12dist).

In the present example, a polyether block copolymer film laminate (31) (e.g., Pebax® Resin, Arkema, Inc., Philadelphia, Pa.) is heat shrunk onto the outer surface of catheter shaft (12) from proximal hub (16) to dilator (14). Laminate (31) may provide a smooth outer surface and smooth the step-down in diameter from the distal end of proximal shaft section (12prox) to the proximal end of distal shaft section (12dist) (e.g., such that laminate (31) provides a smooth surface over the distal end of outer tube (30) and the adjacent outer surface of middle tube (32)). The smooth step down may also be formed by an adhesive fillet. In other versions, the smooth step down may be formed by tapering or chamfering the structure of the distal end of the proximal shaft, eliminating the need for a laminate or adhesive.

The proximal end of middle tube (32) extends into and is secured to hub (16), distal to side arm Luer connector (22). The proximal end of inner tube (36) extends into and is secured within hub (16), proximal to side arm Luer connector (22) and in direct alignment and fluid communication with proximal Luer connector (20). The distal end of middle tube (32) terminates within dilator (14) and the proximal end of dilator (14) is secured to the outer surface of middle tube (32). The distal end of inner tube (36) also extends through dilator (14) and protrudes distally beyond dilator (14), forming the relatively flexible distal tip member (18) as shown in FIG. 1. The distal end of dilator (14) is secured to the outer surface of inner tube (36). In this manner, inner tube lumen (38) extends through the entire catheter shaft (12) from proximal Luer connector (20) through distal tip (18) and may be used as a guidewire lumen or as a working lumen for infusion of irrigation solution, medicaments, contrast media or other substances and/or for aspiration of blood, fluids or debris. Guidewires that may be advantageously used in conjunction with dilation catheter (10) may have a length of 60 cm to 80 cm and may be either 0.014 inch or 0.035 inch, such as those commercially available as the Relieva Vigor® Sinus Guidewires (Acclarent, Inc., Menlo Park, Calif.) or sizes in between such as 0.018 inch, 0.020 inch, or 0.033 inch. Although the drawings show an over-the-wire catheter having a guidewire lumen that extends through the entire length of the catheter, it is to be appreciated that guidewire lumens extending less than the entire length of the catheter (e.g., rapid exchange guidewire lumens) may be used as an alternative to the over-the-wire lumen shown. Additionally, in some versions, rather than advancing the catheter over a guidewire, the catheter may be equipped with a fixed guidewire tip such as any of those described in U.S. Pub. No. 2007/0208301, entitled "Catheters with Non-Removable Guide Members Usable for Treatment of Sinusitis," published Sep. 6, 2007, the disclosure of which is incorporated by reference herein. Still other suitable guidewire configurations will be apparent to those of ordinary skill in the art in view of the teachings herein.

Inner tube lumen (38) may be lined or coated with a lubricious material to facilitate passage of guidewire (GW) through inner tube lumen (38). The diameter of inner tube (36) may be changed to accommodate guidewires of different diameter. In the present example, inner tube lumen (38) is sized to receive a 0.035 inch diameter guidewire (GW). Inner tube lumen (38) may be internally lined or coated with a 2% solution of linear polydimethylsiloxane (PDMS) (e.g., Dow Corning® 360 Medical Fluid, Dow Corning Corporation, Midland, Mich.) diluted in isopropyl alcohol or another silicone material (such as a 2% solution of Dow-Corning MDX4-4159 in isopropyl alcohol). The coating may be cured at room temperature.

Luminal space (34) between the outer surface of inner tube (36) and the inner surface of middle tube (32) is in fluid communication with side arm Luer connector (22) and extends to the interior of dilator (14). Thus, luminal space (34) serves as the passageway through which inflation fluid passes into and out of dilator (14). The size of luminal space (34) and the relatively short length of catheter shaft (12) are optimized to minimize drag on inflation fluid passing through luminal space (34) and allow for rapid deflation of dilator (14). By way of example only, a clearance of 0.006 to 0.007 inches between the inner and outer members may be used for a catheter length of 20-35 cm. The deflation time may be approximately 5-10 seconds, and the deflation time may be measured with application of negative pressure on the inflation/deflation lumen using a 20 cc inflation device that is filled with 10 cc contrast/saline mixture.

Of course, dilation catheter (10) may have a variety of other components, features, properties, and/or configurations. Various suitable alternatives will be apparent to those of ordinary skill in the art in view of the teachings herein.

B. Exemplary Dilator

FIG. 2B shows dilator (14) in greater detail. Dilator (14) of the present example comprises a non-compliant balloon formed of polyethylene terephthalate (PET) film having a thickness of 0.8 mm. Of course, any other suitable material(s) and/or thickness may be used. Dilator (14) has a cylindrical mid-region (44) and tapered proximal and distal end regions (46prox) and (46dist). Dilator (14) may have an overall length of 2.6 cm or any other suitable length. Cylindrical midregion (44) of dilator (14) may have a length of 16 mm and each tapered end region (46prox, 46dist) may have a length of 5 mm. Dilator (44) may have a burst pressure of at least 14 to 16 atmospheres. The outer diameter of dilator (14), when inflated to a pressure of 14 atmospheres, may be in the range of 5.0 mm to 5.5 mm. Dilator (14) may be sized for dilation of the ostia of paranasal sinuses, and such dilator (14) is offered in sizes having outer diameters of 5 mm or 7 mm when inflated to a pressure of 14 atmospheres. Dilation catheters (10) having the 5 mm diameter dilator (14) may be more suitable for use in subjects of small body size, while dilation catheters (10) having the 7 mm diameter dilator (14) may be more suitable for use in subjects having a large body size. Smaller or larger balloons may be used for dilating structures other than the ostia of paranasal sinuses (e.g., airways, Eustachian tube or naso-lacrimal duct dilations, etc.). Larger balloons and higher pressures may be used for dilating revision patients (i.e., patients who have had prior ostial dilations or whose ostia have been previously modified by surgery). Other suitable dimensions and configurations that may be used for dilator (14) will be apparent to those of ordinary skill in the art in view of the teachings herein.

Tapered end regions (46prox, 46dist) are tapered at angle (A) relative to the longitudinal axis (LA) of catheter shaft (12) on which dilator (14) is mounted. This angle of taper (A) may be in the range of about 10 degrees to about 30 degrees, or within any other suitable range. A 20 degree angle of taper (A) may provide an improved transition from the dilator working length to the dilator necks, lower profile, improved crossing, improved tracking, and easier withdrawal of the dilator into the sinus guide catheter after dilator inflation and deflation. It also may also provide optimal performance with minimum increase of overall dilator length.

It may be desirable for the relatively stiff proximal shaft portion (12prox) to extend all the way to or near the proximal end of dilator (14). Such a catheter (10) having a rigid shaft from its proximal end to or near dilator (14) may be advanced directly into the sphenoid sinus ostium (SO) with or without the use of a guide catheter (70). In some versions, the proximal end of dilator (14) could be bonded to the relatively rigid proximal shaft portion (12prox). Such a construction may allow the flexible distal tip (18) to track turns in the anatomy and may be useable to dilate certain passageways (e.g., the sphenoid sinus ostium (SO)) without disrupting the normal anatomy. Additionally, versions with relatively short distal shaft sections (e.g., 1-2 cm beyond the distal end of the rigid proximal shaft portion) may be particularly suitable for dilating the ostia of frontal sinuses. Also, in some versions, proximal shaft section (12prox) may be malleable so that it may be shaped (e.g., bent or formed to a desired curve or multi-curve shape) to facilitate access to any desired passageways or locations.

While expandable dilator (14) of the present example comprises a balloon, it should be understood that various other types of expandable dilators may be used, including but not limited to expandable cages, struts, and other expandable mechanical assemblies may be used as an alternative to a balloon. Some non-limiting examples of expandable dilators other than balloons have previously been described in U.S. Pub. No. 2007/0129751, entitled "Devices, Systems and Methods Useable for Treating Frontal Sinusitis," published Jun. 7, 2007, the disclosure of which is incorporated by reference herein; U.S. Pat. No. 7,803,150, entitled "Devices, Systems and Methods Useable for Treating Frontal Sinusitis," issued Sep. 28, 2010, the disclosure of which is incorporated by reference herein; U.S. Pub. No. 2006/0004323, entitled "Apparatus and Methods for Dilating and Modifying Ostia of Paranasal Sinuses and Other Intranasal or Paranasal Structures," published Jan. 5, 2006, the disclosure of which is incorporated by reference herein; and U.S. Pat. No. 7,654,997, entitled "Devices, Systems and Methods for Diagnosing and Treating Sinusitis and Other Disorders of the Ears, Nose and/or Throat," issued Feb. 2, 2010, the disclosure of which is incorporated by reference herein. In versions of system (1) that incorporate non-balloon versions of dilator (14), such dilators may be actuated in numerous ways as will be apparent to those of ordinary skill in the art in view of the teachings herein. By way of example only, even if such dilators do not expand by filling up with a fluid like a balloon, they may still be actuated by fluid transfers (e.g., in a hydraulic fashion). Thus, the various forms of inflator (50) described herein may still be used to selectively expand such non-balloon versions of dilator (14). Still other suitable forms that dilator (14) may take will be apparent to those of ordinary skill in the art in view of the teachings herein.

C. Exemplary Guide Catheter

FIG. 1 shows a system (1) comprising a guide catheter (70) having a 90 degree curve formed therein in combination with a dilation catheter (10). In some versions, at least part of guide catheter (70) is configured similar to the Relieva Flex™ Sinus Guide Catheter by Acclarent, Inc. of Menlo Park, Calif. It may be desirable for guide catheter (70) to have other preformed curves. Dilation catheter (10) may have a shaft that is about 20 cm in length, with proximal shaft section (12prox) being about 11.3 cm in length and distal shaft section (12dist) being about 8.7 cm in length. Thus, prior to or during the procedure, the entire distal shaft section (12dist) of dilation catheter (10) may be initially advanced into rigid guide catheter (70) without the distal portion of dilation catheter (10) passing through the curve of guide catheter (70) and with only a portion of the rigid proximal shaft section (12prox) of dilation catheter (10) protruding out of the proximal end of guide catheter (70). To facilitate such positioning of dilation catheter (10) within guide catheter (70), and with reference again to FIG. 2, a first shaft marker (26) is provided on proximal shaft section (12prox) of dilation catheter shaft (12). The distal edge of first shaft marker (26) may be about 2.7 cm proximal to the distal end of proximal shaft section (12prox) and about 11.4 cm from the distal end of distal tip member (18). If the operator advances dilation catheter (10) into guide catheter (70) until the distal edge of first shaft marker (26) is flush with the proximal end of guide catheter (70), the entire distal shaft portion (12dist) as well as the distal-most portion of proximal shaft portion (12prox) may be housed within guide catheter (70) such that the distal end of dilation catheter (10) may be located proximal to the curve formed near the distal end of guide catheter (70). Such positioning of dilation catheter (10) within guide catheter (70) provides a guide catheter/dilation catheter assembly that is substantially rigid from proximal hub (16) of dilation catheter (10) to the distal end of guide catheter (70). As a result, the operator may hold or support the entire assembly by grasping or supporting just one location on either dilation catheter (10) or guide catheter (70). For example, the user may hold or support the entire assembly by using his or her fingers to grasp or support either the proximal hub of guide catheter (70), proximal hub (16) of dilation catheter (10), somewhere on proximal shaft section (12prox) of the dilation catheter, or on the shaft of guide catheter (70). Such rigidity may also substantially eliminate the potential for the exposed portion of dilation catheter (10) to droop down onto the patient's chest or onto the adjacent operating table.

When inserted into the patient's body, the overall length of the portion of system (1) that remains exposed (e.g., the proximal part of guide catheter (70) extending out of the patient's nose and the proximal part of dilation catheter (10) extending out of the proximal end of guide catheter (70)) is not only rigid, but sufficiently short (e.g., less than 9 cm) to be easily manageable and capable of being held or supported by a single hand of the operator, thereby allowing the operator's other hand to be used for other purposes, such as for advancing/retracting guidewire (GW) or advancing/retracting dilation catheter (10).

Second shaft marker (24) correlates to the position of dilator (14). If dilation catheter (10) is advanced to a position where the distal edge of second shaft marker (24) is flush with the proximal end of guide catheter (70), the distal tip of the dilation catheter (10) may be flush with the distal tip of guide catheter (70). When the proximal edge of second shaft marker (24) is flush with the proximal end of guide catheter (70), the entire dilator (14) may have advanced out of the distal end of guide catheter (70), and the operator may know that it is safe to inflate dilator (14). As seen in FIG. 1, dilator (14) is advanced some distance out of the distal end of guide catheter (70) until dilator (14) is positioned within the sinus ostium (SO) or other passageway to be dilated. As seen in the enlarged view of dilator (14) shown in FIG. 2B, proximal and distal radiographic markers (40, 42) are provided on the catheter at either end of cylindrical segment (44) of dilator (14). A "C"-arm fluoroscope may be positioned and used to image those proximal and distal markers (40, 42) as well as the sinus ostium (SO), and the position of dilation catheter (10) may be adjusted as needed until the sinus ostium (SO) is midway between proximal and distal radiographic markers (40, 42). Thereafter, an inflator (50) attached to side arm Luer connector (22) may be used to inflate the dilator (14), thereby dilating the sinus ostium (SO) as shown in FIG. 1. In keeping with the operator's ability to use a single hand to hold or support the exteriorized portion of the system, inflator (50) may be attached to side arm Luer connector (22) in advance and may be controlled by a foot pedal that is actuated by the operator's foot.

In some applications of system (1) shown in FIG. 1, an endoscope may be placed in the nose and used to view all or part of the procedure. Because the exposed portion of system (1) is substantially rigid and is less than about 15 cm in length in the present example, the operator may use a single hand to hold the endoscope as well as dilation catheter/guide catheter system (1). Alternatively, a scope holder may be used to hold the endoscope in a fixed position while the operator positions and uses system (1).

Optionally, a stop member (61) may be attached to the guidewire (GW) as shown in FIG. 1. Stop member (61) may serve to prevent dilation catheter (10) and/or guide catheter (70) from inadvertently sliding off of the proximal end of the guidewire (GW). Also, such member (61) may limit the length of guidewire (GW) that may be advanced through dilation catheter (10). This may prevent the operator from advancing too much of the guidewire (GW) into the subject's sinus, which may injure or damage the mucosa lining the sinus cavity. In some versions, member (61) may comprise a standard guidewire torquer of the type commercially available and well known in the fields of interventional cardiology and/or radiology. One example of a commercially available guidewire torquer that is useable with catheter (10) in this application is a two part torquer available as Part No. 97333 from Qosina, Corp., Edgewood, N.Y. Other suitable components that may be used will be apparent to those of ordinary skill in the art in view of the teachings herein. Similarly, it should be understood that guide catheter (70) may have a variety of other components, features, properties, and/or configurations. Various suitable alternatives will be apparent to those of ordinary skill in the art in view of the teachings herein.

D. Exemplary Inflator

FIG. 1 shows an exemplary conventional inflator (50) that is coupled with side arm Luer connector (22) via a flexible conduit (60) (e.g., a flexible, surgical grade tube). Inflator (50) of this example comprises a syringe barrel (52) that defines a variable fluid volume and a plunger (54) that translates relative to barrel (52) do vary the fluid volume within barrel (52). Barrel (52) includes graduated markings (54) to indicate the amount of fluid within barrel (52). Inflator (50) also includes a gauge (58) to show the pressure of fluid within barrel (52). It should be understood that barrel (52) is in fluid communication with dilator (14) via conduit (60) and dilation catheter (10), such that fluid may be transferred to and from dilator (14) by advancing plunger (54) distally relative to barrel (52) or retracting plunger (54) proximally relative to barrel (52), respectively. Thus, an operator may inflate dilator (14) by advancing plunger (54) distally relative to barrel (52); and may deflate dilator by retracting plunger (54) proximally relative to barrel (52). It should also be understood that the pressure reading shown by gauge (58) may be indicative of the fluid pressure within dilator (14). In the present example, the fluid within this fluid circuit is saline, though any other suitable fluid may be used.

Inflator (50) shown in FIG. 1 is just one example of an inflator that may be incorporated into system (1). Additional merely illustrative examples of inflators (150, 250, 350, 450, 550, 650, 750) are shown in FIGS. 3-6 and 10-12; and will be described in greater detail below. It should be understood that these exemplary alternative inflators (150, 250, 350, 450, 550, 650, 750) may be readily coupled with conduit (60) in place of inflator (50) described above, for use in system (1). In some versions, inflator (150, 250, 350, 450, 550, 650, 750) may be directly coupled with side arm Luer connector (22), such that conduit (60) is simply omitted. Other suitable configurations and arrangements will be apparent to those of ordinary skill in the art in view of the teachings herein.

1. Exemplary Alternative Inflator with Knob and Pushbutton Thread Release

Figure 3:
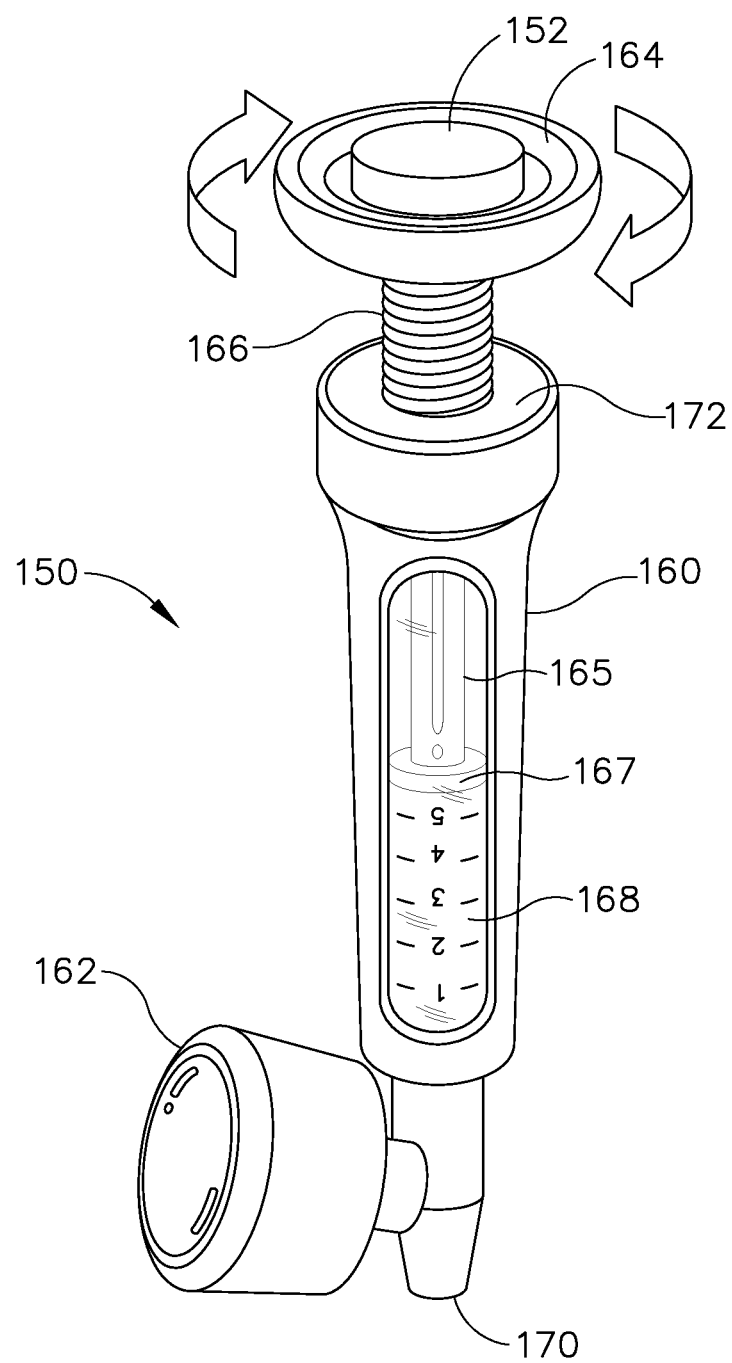
FIG. 3 depicts a perspective view of an exemplary inflator for use with the system of FIG. 1.

FIG. 3 shows an exemplary inflator (150) that comprises a body (160), an actuator knob (164), and a pressure gauge (162). Body (160) of the present example is formed as a substantially hollow cylinder, similar to syringe barrel (52) described above, although other suitable configurations may be used. Body (160) comprises a reservoir (168), a distal port (170), and a proximal cap (172). A rod (165) extends into body (160). Plunger (167) is coupled to a distal end of rod (165) and extends outwardly to the inner diameter of body (160) to form a substantially fluid tight seal with body (160). The volume between plunger (167) and the distal end of body (160) forms reservoir (168). Reservoir (168) may be configured to hold about 3 to about 5 cc of fluid (e.g., saline). Rod (165) and plunger (167) may translate proximally and distally to adjust the size of reservoir (168). When rod (165) and plunger (167) translate proximally, the volume of reservoir (168) increases. When rod (165) and plunger (167) translate distally, the volume of reservoir (168) decreases. Port (170) at the distal end of body (160) is in fluid communication with reservoir (168) such that fluid may flow into and out of reservoir (168) via port (170). Port (170) may be coupled with conduit (60) of system (1).

Actuator knob (164) is coupled to body (160) via a threaded shaft (166), which is in selective threaded engagement with proximal cap (172) of body (160). Threaded shaft (166) is configured to rotate unitarily with actuator knob (164). Thus, rotation of actuator knob (164) relative to body (160) will cause threaded shaft (166) to translate relative to body (160) when the threading of threaded shaft (166) is engaged with proximal cap (172). Threaded shaft (166) is further coupled with rod (165) such that when actuator knob (164) is rotated relative to body (160), rod (165) and plunger (167) translate proximally or distally relative to body (165) based on the direction in which actuator knob (164) and threaded shaft (166) are rotated. In some versions, threaded shaft (166) and rod (165) are the same structure, such that threaded shaft (166) extends all the way to plunger (167). In some such versions, threaded shaft (166) rotates freely relative to plunger (167).

In the present example, push button (152) is operable to disengage the threading of threaded shaft (166) relative to proximal cap (172), to thereby permit threaded shaft (166) to translate freely relative to body (160) when push button (152) is in a depressed position. Various suitable features that may be used to provide such operability will be apparent to those of ordinary skill in the art in view of the teachings herein. By way of example only, the threading of threaded shaft (166) may be selectively retractable inwardly relative to the longitudinal axis of threaded shaft (166). A translating cam component (not shown) that is coupled with push button (152) may be operable to extend and/or retract the threading of threaded shaft (166) based on the position of push button (152). For instance, when push button (152) is not being depressed, the cam component may be biased to a position where it urges the threading outwardly and holds the threading in the outward position, into engagement with threaded cap (172). The threading may itself be resiliently biased to retract inwardly, such that when push button (152) is depressed, the cam component disengages the threading and the threading retracts inwardly to disengage body (160). It should also be understood that push button (152) may be resiliently biased toward the non-depressed position. Still other suitable components and configurations that may be used to provide the above-described selective engagement between threaded shaft (166) and proximal cap (172) will be apparent to those of ordinary skill in the art in view of the teachings herein.

Gauge (162) of the present example is positioned distal of reservoir (168) to measure the pressure within system (1). Gauge (162) may include a pivoting pin that indicates fluid pressure based on the angular position of the pin. Alternatively, gauge (162) may provide any other suitable type of indication of fluid pressure, including but not limited to other types of fluid pressure indication described below. In the present example, gauge (162) is operable to indicate pressure levels up to at least about 12 atmospheres. For instance, some uses of system (1) may include inflation of dilator (14) to a range between about 10 atmospheres and about 12 atmospheres in order to sufficiently dilate a targeted anatomical passageway. Gauge (162) may thus provide the user with real time feedback indicating the fluid pressure within dilator (14) to enable the user to determine whether the desired pressure level has been achieved.

In an exemplary use of inflator (150), a user may start with plunger (167) advanced to a distal position in body (160). The user may then position port (170) in a bowl or other container of saline to draw fluid from. In instances where port (170) is coupled with one end of conduit (60), the user may position the other end of conduit (60) in the saline. In either case, the user may then retract plunger (167) relative to body (160) to draw the saline (or other fluid) into reservoir (168). In some instances, the user depresses button (152) to disengage threading of threaded shaft (166) from proximal cap (172), thereby permitting the user to freely pull plunger (167) proximally without having to rotate actuator knob (164). The user may nevertheless grasp actuator knob (164) in order to translate plunger (167) proximally. The user may observe the position of plunger (167) relative to indicia on body (160) and may initially draw in more fluid than the user expects to need in order to sufficiently inflate dilator (14). The user may then remove port (170) or conduit (60) from the saline container and advance plunger (167) distally in order to purge air from reservoir (168). For instance, the user may orient inflator (150) such that port (170) is positioned upwardly to gather air at the top of reservoir (168) before advancing plunger (167) distally in order to purge air from reservoir (168).

Once reservoir (168) has been sufficiently filled with fluid and air has been purged, the user may couple inflator (150) with dilation catheter (10), such as by coupling port (170) with side arm Luer connector (22) via a flexible conduit (60). With dilator (14) being suitably positioned within an anatomical passageway (e.g., a sinus ostium (SO), etc.), the user may then advance plunger (167) distally in order to transfer fluid from reservoir (168) to dilator (14). In some instances, this act may begin with free translation of threaded shaft (166) relative to proximal cap (172), with the user depressing push button (152) to disengage the threading, and with the user gripping actuator knob (164) to translate threaded shaft (166) and plunger (167) distally. At some point, however, the user may release push button (152) to engage the threading of threaded shaft (166) with proximal cap (172), and may finish the final stages of distal translation of plunger (167) by rotating actuator knob (164). This may enable the user to more precisely "dial in" the appropriate amount of pressure in dilator (14), observing the pressure reading at gauge (162) while rotating actuator knob (164).

In some instances, the user simply relies on tactile feedback in the form of physical resistance to pushing of actuator knob (164) in order to determine the appropriate time to transition from pushing of actuator knob (164) (with push button (152) depressed) to rotating of actuator knob (164) (with push button (152) released). In addition or in the alternative, the user may determine the appropriate time to transition from pushing of actuator knob (164) to rotating of actuator knob (164) based on the position of plunger (167) relative to one or more markings on body (160). Other suitable forms of feedback that may be used to determine an appropriate transition time from pushing of actuator knob (164) to rotating of actuator knob (164) will be apparent to those of ordinary skill in the art in view of the teachings herein.

Once the user has attained the desired level of pressure in dilator (14) within the anatomical passageway to dilate the anatomical passageway, the user may pause for an approximate, predetermined period of time (e.g., approximately three seconds, etc.). The user may then once again depress push button (152) and pull knob (164) proximally relative to body (160), to thereby retract plunger (167) for withdrawal of fluid from dilator (14). With dilator (14) now deflated, dilator (14) may be retracted from the patient. Alternatively, if the user wishes to dilate additional anatomical passageways, dilator (14) may be positioned in the next anatomical passageway, and the user may repeat the above steps to dilate that next anatomical passageway. Thus, the same volume of fluid within reservoir (168) may be used repeatedly to dilate a plurality of anatomical passageways, without having to withdraw dilator (14) from the patient, and without having to decouple inflator (150) from the rest of system (1), until all of the desired dilations have been completed.

In the foregoing example, the threading of threaded shaft (166) is engaged with proximal cap (172) when push button (152) is not being depressed. In some other versions, the threading of threaded shaft (166) is engaged with proximal cap (172) only when push button (152) is being depressed. Other suitable variations of inflator (150) will be apparent to those of ordinary skill in the art in view of the teachings herein. Similarly, other suitable ways in which inflator (150) may be used will be apparent to those of ordinary skill in the art in view of the teachings herein.

2. Exemplary Alternative Inflator with Knob and Rotary Thread Release

Figure 4:
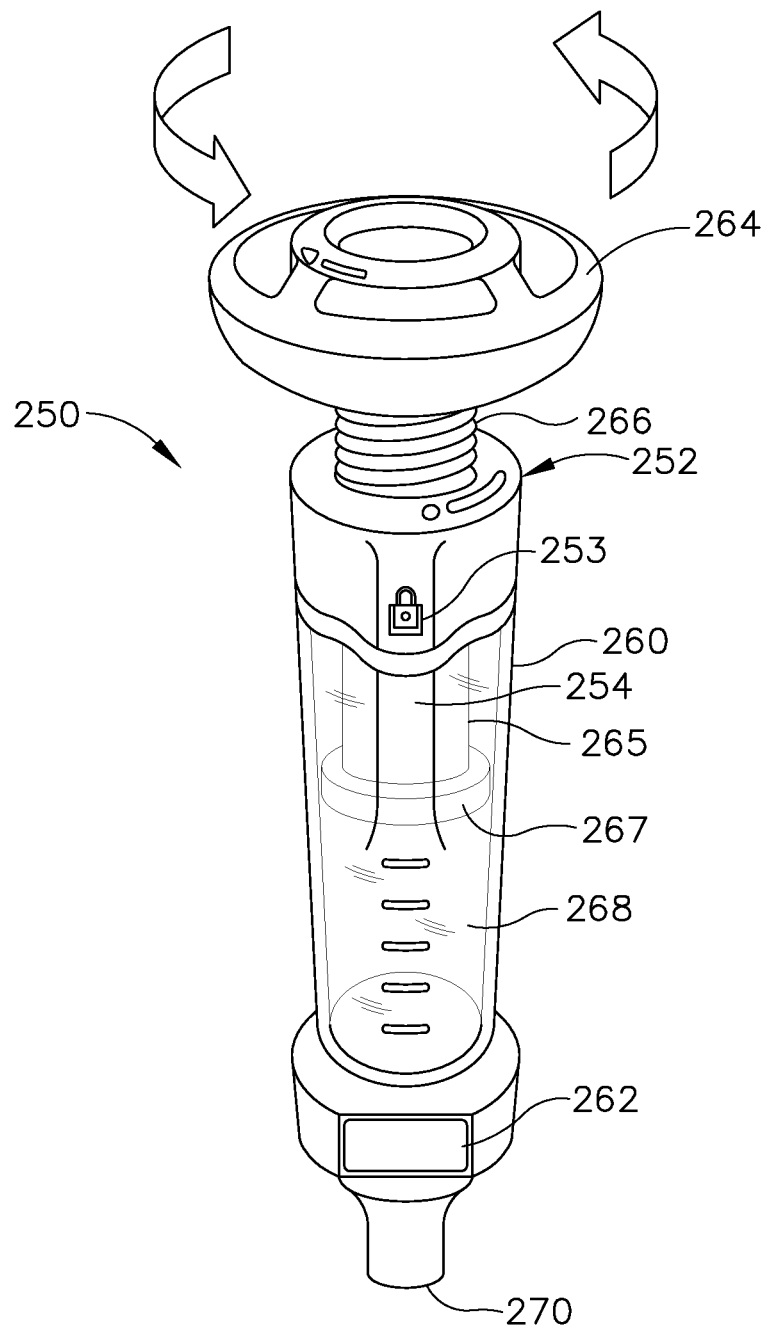
FIG. 4 depicts a perspective view of another exemplary inflator.

FIG. 4 shows another exemplary inflator (250). Inflator (250) of this example is substantially similar to inflator (150) described above with reference to FIG. 3. In particular, inflator (250) comprises a body (260), an actuator knob (264), and a pressure gauge (262). Body (260) of the present example is formed as a substantially hollow cylinder, similar to syringe barrel (52) described above, although other suitable configurations may be used. Body (260) comprises a reservoir (268), a distal port (270), and a rotary locking feature (252) at the proximal end of body (260). A rod (265) extends into body (260). Plunger (267) is coupled to a distal end of rod (265) and extends outwardly to the inner diameter of body (260) to form a substantially fluid tight seal with body (260). The volume between plunger (267) and the distal end of body (260) forms reservoir (268). Reservoir (268) may be configured to hold about 3 to about 5 cc of fluid (e.g., saline). Rod (265) and plunger (267) may translate proximally and distally to adjust the size of reservoir (268). When rod (265) and plunger (267) translate proximally, the volume of reservoir (268) increases. When rod (265) and plunger (267) translate distally, the volume of reservoir (268) decreases. Port (270) at the distal end of body (260) is in fluid communication with reservoir (268) such that fluid may flow into and out of reservoir (268) via port (270). Port (270) may be coupled with conduit (60) of system (1).

Actuator knob (264) is coupled to body (260) via a threaded shaft (266), which is in selective threaded engagement with rotary locking feature (252) of body (260). Threaded shaft (266) is configured to rotate unitarily with actuator knob (264). Thus, rotation of actuator knob (264) relative to body (260) will cause threaded shaft (266) to translate relative to body (260) when the threading of threaded shaft (266) is engaged with rotary locking feature (252). Threaded shaft (266) is further coupled with rod (265) such that when actuator knob (264) is rotated relative to body (260), rod (265) and plunger (267) translate proximally or distally relative to body (265) based on the direction in which actuator knob (264) and threaded shaft (266) are rotated. In some versions, threaded shaft (266) and rod (265) are the same structure, such that threaded shaft (266) extends all the way to plunger (267). In some such versions, threaded shaft (266) rotates freely relative to plunger (267).

In the present example, rotary locking feature (252) comprises an annular component that is rotatable relative to body (260) to selectively engage/disengage the threading of threaded shaft (266). In particular, rotary locking feature (252) is operable to selectively disengage the threading of threaded shaft (266), to thereby permit threaded shaft (266) to translate freely relative to body (260) when rotary locking feature (252) is rotated to an unlocked position. Various suitable features that may be used to provide such operability will be apparent to those of ordinary skill in the art in view of the teachings herein. By way of example only, rotary locking feature (252) may include retractable internal threading that is selectively engaged with the external threading of threaded shaft (266) based on the rotational position of rotary locking feature (252) relative to body (260). As another merely illustrative example, an internally threaded member may be positioned within rotary locking feature (252), and rotary locking feature (252) may be configured to selectively secure the rotational position of this internally threaded member relative to body (260) based on the rotational position of rotary locking feature (252) relative to body (260). For instance, the internally threaded member may be rotationally fixed relative to body (260) when rotary locking feature (252) is rotated to a locked position; while the internally threaded member may rotate freely relative to body (260) when rotary locking feature (252) is rotated to an unlocked position. Still other suitable components and configurations that may be used to provide the above-described selective engagement between threaded shaft (266) and body (260) will be apparent to those of ordinary skill in the art in view of the teachings herein.

In addition, body (260) and rotary locking feature (252) of the present example include complementary features to provide feedback to the user indicating whether rotary locking feature (252) is in the locked or unlocked position. In particular, rotary locking feature (252) includes a graphical representation (253) of a padlock that aligns with a complementary indicator on body (260) when rotary locking feature (252) is in the locked position. In addition, body (260) and rotary locking feature (252) have the same asymmetric cross-sectional shape. When rotary locking feature (252) is rotated to the locked position, these cross-sections align such that the outer surfaces of body and rotary locking feature (252) are substantially flush with each other. When rotary locking feature (252) is rotated to the unlocked position, the cross-sections are not aligned and their non-alignment is visually pronounced by the asymmetry of their cross-sections. In other words, the non-alignment of the cross-sections is easy to observe visually and tactilely. Other suitable ways in which the locked/unlocked state of rotary locking feature (252) may be indicated will be apparent to those of ordinary skill in the art in view of the teachings herein.

Gauge (262) of the present example is positioned distal of reservoir (268) to measure the pressure within system (1). Gauge (262) of this example comprises a digital pressure gauge with an LCD or LED screen providing the numerical value of the fluid pressure. Alternatively, gauge (262) may provide any other suitable type of indication of fluid pressure, including but not limited to the other types of fluid pressure indication described herein. In the present example, gauge (262) is operable to indicate pressure levels up to at least about 12 atmospheres. For instance, some uses of system (1) may include inflation of dilator (14) to a range between about 10 atmospheres and about 12 atmospheres in order to sufficiently dilate a targeted anatomical passageway. Gauge (262) may thus provide the user with real time feedback indicating the fluid pressure within dilator (14) to enable the user to determine whether the desired pressure level has been achieved.

In an exemplary use of inflator (250), a user may start with plunger (267) advanced to a distal position in body (260). The user may then position port (270) in a bowl or other container of saline to draw fluid from. In instances where port (270) is coupled with one end of conduit (60), the user may position the other end of conduit (60) in the saline. In either case, the user may then retract plunger (267) relative to body (260) to draw the saline (or other fluid) into reservoir (268). In some instances, rotary locking feature (252) is rotated to the unlocked position at this stage, to disengage threading of threaded shaft (266) relative to body (260), thereby permitting the user to freely pull plunger (267) proximally without having to rotate actuator knob (264). The user may nevertheless grasp actuator knob (264) in order to translate plunger (267) proximally. The user may observe the position of plunger (267) relative to indicia on body (260) and may initially draw in more fluid than the user expects to need in order to sufficiently inflate dilator (14). The user may then remove port (270) or conduit (60) from the saline container and advance plunger (267) distally in order to purge air from reservoir (268). For instance, the user may orient inflator (250) such that port (270) is positioned upwardly to gather air at the top of reservoir (268) before advancing plunger (267) distally in order to purge air from reservoir (268).

Once reservoir (268) has been sufficiently filled with fluid and air has been purged, the user may couple inflator (250) with dilation catheter (10), such as by coupling port (270) with side arm Luer connector (22) via a flexible conduit (60). With dilator (14) being suitably positioned within an anatomical passageway (e.g., a sinus ostium (SO), etc.), the user may then advance plunger (267) distally in order to transfer fluid from reservoir (268) to dilator (14). In some instances, this act may begin with free translation of threaded shaft (266) relative to body (260), with rotary locking feature (252) being rotated to the unlocked position to disengage the threading, and with the user gripping actuator knob (264) to translate threaded shaft (266) and plunger (267) distally. At some point, however, the user may rotate rotary locking feature (252) to the locked position, to engage the threading of threaded shaft (266) with body (260), and may finish the final stages of distal translation of plunger (267) by rotating actuator knob (264). This may enable the user to more precisely "dial in" the appropriate amount of pressure in dilator (14), observing the pressure reading at gauge (262) while rotating actuator knob (264).

In some instances, the user simply relies on tactile feedback in the form of physical resistance to pushing of actuator knob (264) in order to determine the appropriate time to transition from pushing of actuator knob (264) (with rotary locking feature (252) in the unlocked position) to rotating of actuator knob (264) (with rotary locking feature (252) in the locked position). In addition or in the alternative, the user may determine the appropriate time to transition from pushing of actuator knob (264) to rotating of actuator knob (264) based on the position of plunger (267) relative to one or more markings on body (260). Other suitable forms of feedback that may be used to determine an appropriate transition time from pushing of actuator knob (264) to rotating of actuator knob (264) will be apparent to those of ordinary skill in the art in view of the teachings herein.

Once the user has attained the desired level of pressure in dilator (14) within the anatomical passageway to dilate the anatomical passageway, the user may pause for an approximate, predetermined period of time (e.g., approximately three seconds, etc.). The user may then once again rotate rotary locking feature (252) back to the unlocked position and pull knob (264) proximally relative to body (260), to thereby retract plunger (267) for withdrawal of fluid from dilator (14). With dilator (14) now deflated, dilator (14) may be retracted from the patient. Alternatively, if the user wishes to dilate additional anatomical passageways, dilator (14) may be positioned in the next anatomical passageway, and the user may repeat the above steps to dilate that next anatomical passageway. Thus, the same volume of fluid within reservoir (268) may be used repeatedly to dilate a plurality of anatomical passageways, without having to withdraw dilator (14) from the patient, and without having to decouple inflator (250) from the rest of system (1), until all of the desired dilations have been completed.

Other suitable variations of inflator (250) will be apparent to those of ordinary skill in the art in view of the teachings herein. Similarly, other suitable ways in which inflator (250) may be used will be apparent to those of ordinary skill in the art in view of the teachings herein.

3. Exemplary Alternative Inflator with Resiliently Biased Plunger

Figure 5:
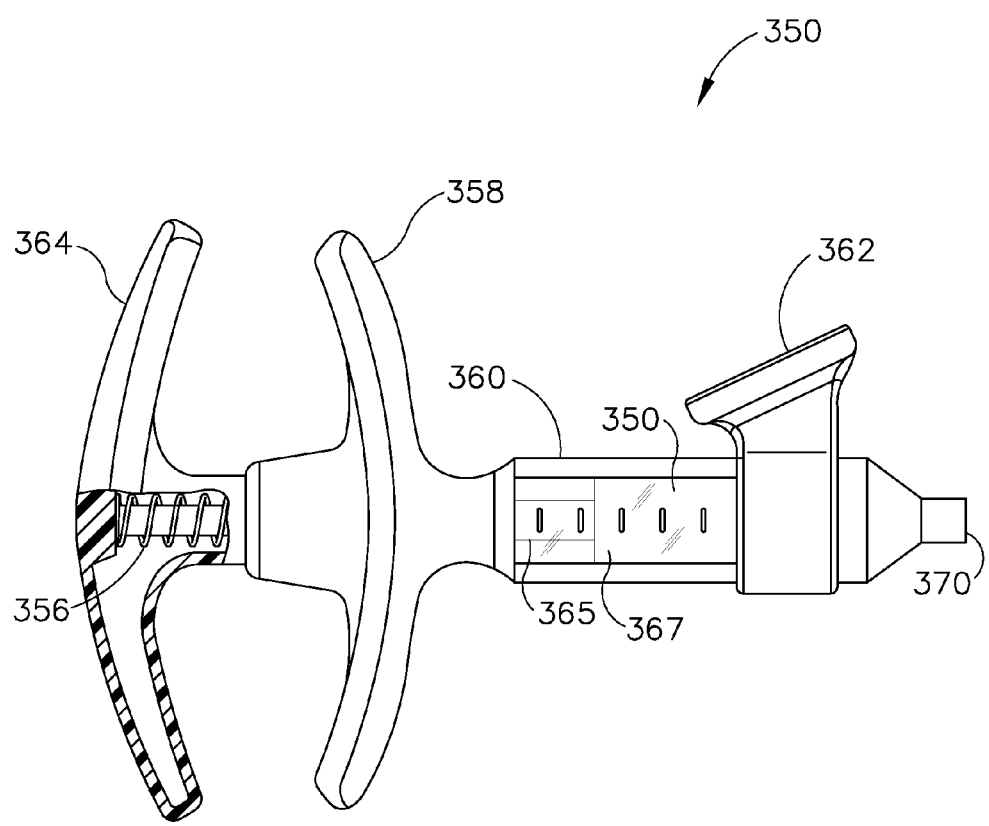
FIG. 5 depicts a side view of another exemplary inflator, with a portion removed.

FIG. 5 shows another exemplary inflator (350). Inflator (350) of this example is configured for one-handed operation. Inflator (350) of this example comprises a body (360), an actuator (364), and a pressure gauge (362). Body (360) of the present example is formed as a substantially hollow cylinder, similar to syringe barrel (52) described above, although other suitable configurations may be used. Body (360) comprises a reservoir (368), a distal port (370), and a handle (358) at the proximal end of body (360). A rod (365) extends into body (360). Plunger (367) is coupled to a distal end of rod (365) and extends outwardly to the inner diameter of body (360) to form a substantially fluid tight seal with body (360). The volume between plunger (367) and the distal end of body (360) forms reservoir (368). Reservoir (368) may be configured to hold about 3 to about 5 cc of fluid (e.g., saline). Rod (365) and plunger (367) may translate proximally and distally to adjust the size of reservoir (368). When rod (365) and plunger (367) translate proximally, the volume of reservoir (368) increases. When rod (365) and plunger (367) translate distally, the volume of reservoir (368) decreases. Port (370) at the distal end of body (360) is in fluid communication with reservoir (368) such that fluid may flow into and out of reservoir (368) via port (370). Port (370) may be coupled with conduit (60) of system (1).

Actuator (364) is unitarily secured to rod (365), such that actuator (364) and rod (365) (and, hence, plunger (367)) translate unitarily relative to body (360). A coil spring (356) is coaxially disposed about rod (365) and bears against both actuator (364) and body (360). Coil spring (356) thus resiliently biases actuator (364) proximally. Of course, any other suitable type of resilient member may be used. Actuator (364) has a "T" shape that is configured to rest in the palm of the user's hand. Handle (358) of body (360) is configured such that a user may wrap his or her fingers around handle (358) with actuator (364) in the palm of the same hand. The user may thus drive actuator (364) distally relative to handle (358) by squeezing with that single hand. As the user thereafter releases their grip, the resilient bias of coil spring (356) returns actuator (364) proximally relative to handle (358). Plunger (367) translates relative to body (360) accordingly.

Gauge (362) of the present example is positioned distal of reservoir (368) to measure the pressure within system (1). Gauge (362) of this example comprises a digital pressure gauge with an LCD or LED screen providing the numerical value of the fluid pressure. Alternatively, gauge (362) may provide any other suitable type of indication of fluid pressure, including but not limited to the other types of fluid pressure indication described herein. In the present example, gauge (362) is operable to indicate pressure levels up to at least about 12 atmospheres. For instance, some uses of system (1) may include inflation of dilator (14) to a range between about 10 atmospheres and about 12 atmospheres in order to sufficiently dilate a targeted anatomical passageway. Gauge (362) may thus provide the user with real time feedback indicating the fluid pressure within dilator (14) to enable the user to determine whether the desired pressure level has been achieved.

In an exemplary use of inflator (350), a user may start with plunger (367) advanced to a distal position in body (360). This may be accomplished by squeezing actuator (364) toward handle (358) with a single hand. The user may then position port (370) in a bowl or other container of saline to draw fluid from. In instances where port (370) is coupled with one end of conduit (60), the user may position the other end of conduit (60) in the saline. In either case, the user may then release actuator (364) relative to handle (358). The resilient bias of coil spring (356) may cause actuator (364) and rod (365) to retract relative to body (360), which may in turn retract plunger (367) relative to body (360) to draw the saline (or other fluid) into reservoir (368). The user may then remove port (370) or conduit (60) from the saline container and advance plunger (367) distally in order to purge air from reservoir (368). For instance, the user may orient inflator (350) such that port (370) is positioned upwardly to gather air at the top of reservoir (368) before advancing plunger (367) distally in order to purge air from reservoir (368).

Once reservoir (368) has been sufficiently filled with fluid and air has been purged, the user may couple inflator (350) with dilation catheter (10), such as by coupling port (370) with side arm Luer connector (22) via a flexible conduit (60). With dilator (14) being suitably positioned within an anatomical passageway (e.g., a sinus ostium (SO), etc.), the user may then advance actuator (364) distally by squeezing actuator (364) and handle (358) with a single hand, in order to transfer fluid from reservoir (368) to dilator (14). The user may observe the pressure reading at gauge (362) while advancing actuator (364) distally in order to determine when the appropriate fluid pressure level has been reached.

Once the user has attained the desired level of pressure in dilator (14) within the anatomical passageway to dilate the anatomical passageway, the user may pause for an approximate, predetermined period of time (e.g., approximately three seconds, etc.). The user may then release their grip on actuator (364) to allow coil spring (356) to translate actuator (364) and rod (365) proximally, to thereby retract plunger (267) for withdrawal of fluid from dilator (14). With dilator (14) now deflated, dilator (14) may be retracted from the patient. Alternatively, if the user wishes to dilate additional anatomical passageways, dilator (14) may be positioned in the next anatomical passageway, and the user may repeat the above steps to dilate that next anatomical passageway. Thus, the same volume of fluid within reservoir (368) may be used repeatedly to dilate a plurality of anatomical passageways, without having to withdraw dilator (14) from the patient, and without having to decouple inflator (350) from the rest of system (1), until all of the desired dilations have been completed.

In some instances, rod (365) and body (360) include complementary detent features (and/or some other type of feature(s)) that provide the user with audible and/or tactile feedback. For instance, such features may provide the user with feedback to indicate longitudinal positions of plunger (367) that are predeterminedly associated with an appropriate pressure level in dilator (14). In addition or in the alternative, such features may provide the user with feedback to indicate that the longitudinal position of plunger (367) is getting close to a position that is predeterminedly associated with an appropriate pressure level in dilator (14), thereby alerting the user to slow their distal advancement of actuator (364) and carefully watch gauge (362). Detent features (and/or some other type of feature(s)) may also provide the user with audible and/or tactile feedback to indicate when plunger (367) has reached a position that is predeterminedly associated with air being purged from reservoir (368) before port (370) is coupled with side arm Luer connector (22). As yet another merely illustrative variation, some versions may provide a manual locking feature that enables the user to selectively secure the position of actuator (364) relative to body—either at one or more predetermined positions and/or at positions selected ad hoc by the user. Other suitable variations of inflator (350) will be apparent to those of ordinary skill in the art in view of the teachings herein. Similarly, other suitable ways in which inflator (350) may be used will be apparent to those of ordinary skill in the art in view of the teachings herein.

4. Exemplary Alternative Inflator with Lever Actuated Crankshaft Assembly

Figure 6:
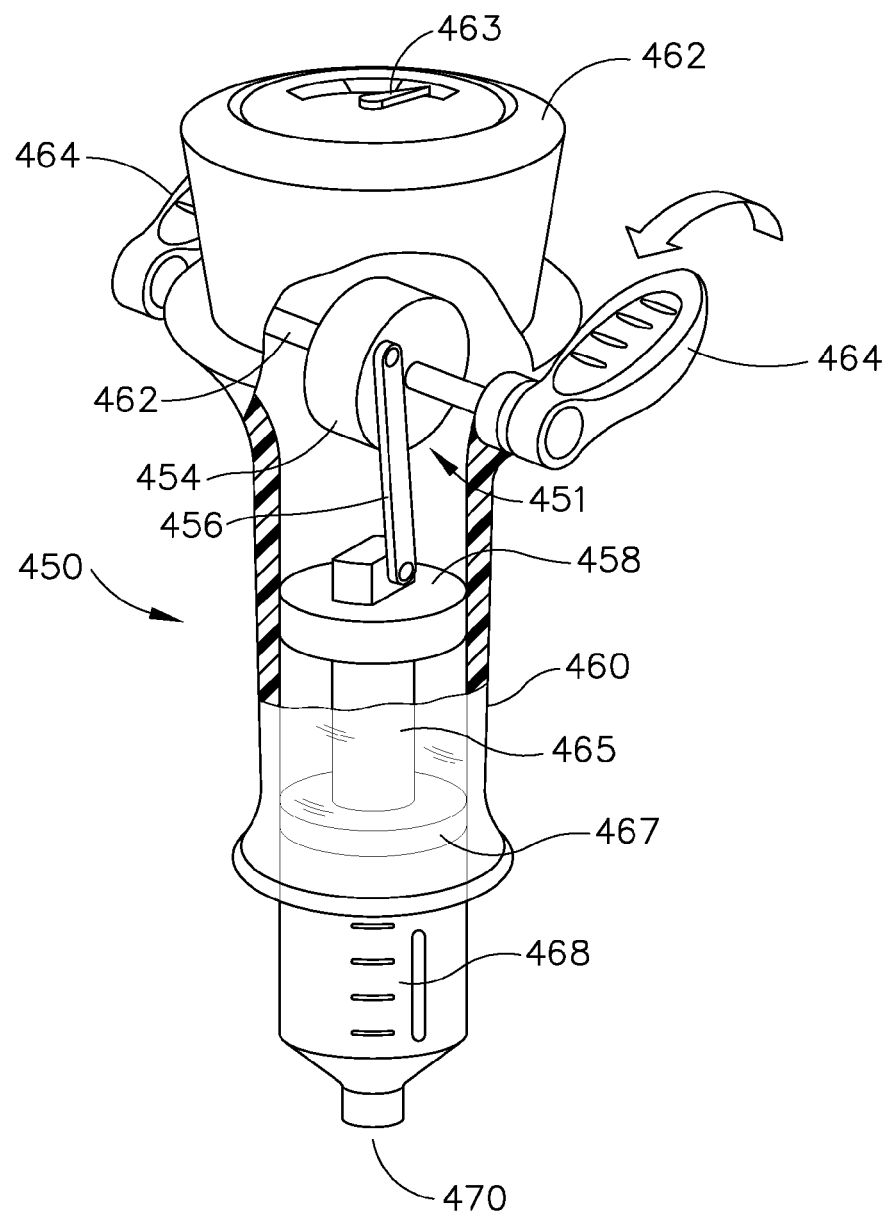
FIG. 6 depicts a perspective view of another exemplary inflator.

FIG. 6 shows another exemplary inflator (450). Inflator (450) of this example comprises a body (460), a pair of actuator levers (464), and a pressure gauge (462). Body (460) of the present example is formed as a substantially hollow cylinder, similar to syringe barrel (52) described above, although other suitable configurations may be used. Body (460) comprises a reservoir (468), a distal port (470), and a crank shaft assembly (451) at the proximal end of body (460). A rod (465) is longitudinally driven by crank shaft assembly (451) as described in greater detail below. Plunger (467) is coupled to a distal end of rod (465) and extends outwardly to the inner diameter of body (460) to form a substantially fluid tight seal with body (460). The volume between plunger (467) and the distal end of body (460) forms reservoir (468). Reservoir (468) may be configured to hold about 3 to about 5 cc of fluid (e.g., saline). Rod (465) and plunger (467) may translate proximally and distally to adjust the size of reservoir (468). When rod (465) and plunger (467) translate proximally, the volume of reservoir (468) increases. When rod (465) and plunger (467) translate distally, the volume of reservoir (468) decreases. Port (470) at the distal end of body (460) is in fluid communication with reservoir (468) such that fluid may flow into and out of reservoir (468) via port (470). Port (470) may be coupled with conduit (60) of system (1).

Figure 7:
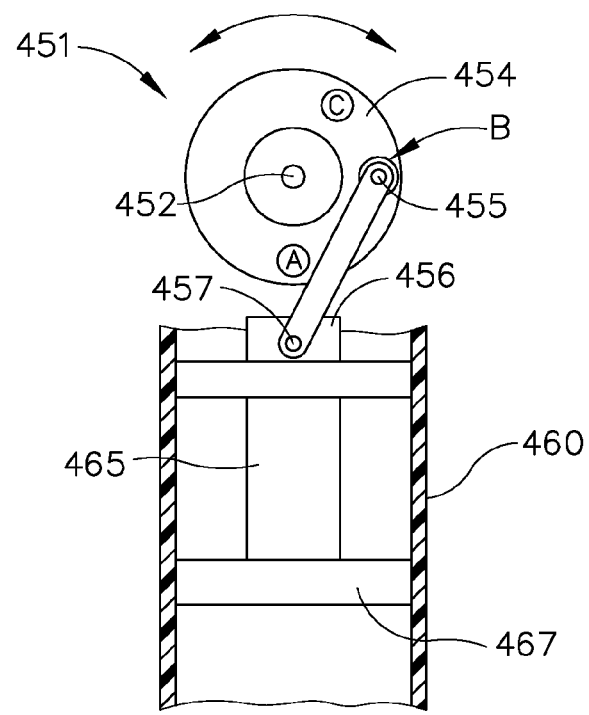
FIG. 7 depicts a side view of the crank shaft assembly from the inflator of FIG. 5.

Crank shaft assembly (451) comprises a crank shaft (452) and a crank wheel (454). Crank shaft (452) and crank wheel (454) are coaxial with each other and rotate unitarily with each other. Actuator levers (464) are secured to opposing ends of crank shaft (452). Actuator levers (464) are operable to rotate crank shaft (452) and crank wheel (454) relative to body (460), about the axis shared by crank shaft (452) and crank wheel (454). As best seen in FIG. 7, crank wheel (454) includes an integral crank pin (455) that extends along an axis that is offset from the axis shared by crank shaft (452) and crank wheel (454). In other words, crank pin (455) is off center relative to crank wheel (454). One end of a connecting rod (456) is pivotally coupled with crank pin (455), while the other end of connecting rod (456) is pivotally coupled with a pin (457) at the head (458) of rod (465). These couplings may include bushings, bearings, and/or other features to provide smooth pivoting movement of connecting rod (456) relative to crank wheel (454) and head (458). It should be understood that the configuration of crank shaft assembly (451) will provide reciprocation of rod (465) and plunger (467) in response to rotation of actuator levers (464) relative to body (460). It should also be understood that positioning of actuator levers (464) on both sides of body (460) may facilitate use by both left-handed and right-handed users.

In the present example, actuator levers (464), crank shaft (452), and crank wheel (454) are operable to rotate through a range of approximately 150°. Alternatively, any other suitable angular range may be provided. In instances providing a limited angular range, the limits may be imposed by bosses or other features that provide hard stops preventing rotation of actuator levers (464), crank shaft (452), and crank wheel (454) beyond the predetermined range. As shown in FIG. 7, there are three predetermined angular positions within the range—position "A," position "B," and position "C." These angular positions are associated with the location of crank pin (455) at particular stages of use of inflator (450) as will be described in greater detail below. It should be understood that inflator (450) may include detent features (and/or some other type of feature(s)) that provide the user with audible and/or tactile feedback to indicate arrival at position "A," position "B," and/or position "C." In some other versions, a detent feature is only used to indicate arrival at position "B," while hard stops indicate arrival at position "A" and position "B." Other suitable forms of feedback will be apparent to those of ordinary skill in the art in view of the teachings herein.

Figures 8, 9:
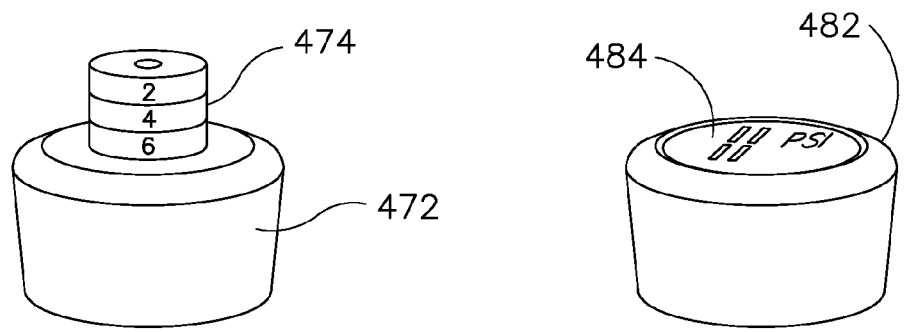
FIG. 8 depicts a perspective view of another exemplary pressure gauge.
FIG. 9 depicts a perspective view of another exemplary pressure gauge.

Gauge (462) of the present example is positioned at the proximal end of body (460), and includes a pivoting pin (463) that indicates fluid pressure based on the angular position of the pin. Alternatively, gauge (462) may provide any other suitable type of indication of fluid pressure. By way of example only, gauge (462) may be substituted with the gauge (472) shown in FIG. 8, which includes a longitudinally sliding pressure indicator (474) similar to a conventional tire pressure gauge. As another merely illustrative alternative, gauge (462) may be substituted with the gauge (482) shown in FIG. 9, which includes a digital display (484) showing the pressure reading in numerical form. Other suitable forms that gauge (462) may take will be apparent to those of ordinary skill in the art in view of the teachings herein. In the present example, gauge (462) is operable to indicate pressure levels up to at least about 12 atmospheres. For instance, some uses of system (1) may include inflation of dilator (14) to a range between about 10 atmospheres and about 12 atmospheres in order to sufficiently dilate a targeted anatomical passageway. Gauge (462) may thus provide the user with real time feedback indicating the fluid pressure within dilator (14) to enable the user to determine whether the desired pressure level has been achieved.

In an exemplary use of inflator (450), a user may start with actuator levers (464) at a position corresponding to crank pin (455) being located at position "A," which further corresponds to plunger (467) being at a distal position in body (460). The user may then position port (470) in a bowl or other container of saline to draw fluid from. In instances where port (470) is coupled with one end of conduit (60), the user may position the other end of conduit (60) in the saline. In either case, the user may then pivot actuator levers (464) to a position corresponding to crank pin (455) being located at position "C," which further corresponds to plunger (467) being at a proximal position in body (460). This proximal movement of plunger (467) draws the saline (or other fluid) into reservoir (468). The user may then remove port (470) or conduit (60) from the saline container and pivot actuator levers (464) to a position corresponding to crank pin (455) being located at position "B," which further corresponds to plunger (467) being at an intermediate position in body (460). It should be understood that transitioning crank pin (455) from position "A" to position "C" will entail pivoting actuator levers (464) in a first direction; while transitioning crank pin (455) from position "C" to position "B" will entail pivoting actuator levers (464) in a second direction. It should also be understood that the distal movement of plunger (467) resulting from the transition of crank pin (455) from position "C" to position "B" may purge air from reservoir (468). For instance, the user may orient inflator (450) such that port (470) is positioned upwardly to gather air at the top of reservoir (468) before advancing plunger (467) distally in order to purge air from reservoir (468).

Once reservoir (468) has been sufficiently filled with fluid and air has been purged, the user may couple inflator (450) with dilation catheter (10), such as by coupling port (470) with side arm Luer connector (22) via a flexible conduit (60). With dilator (14) being suitably positioned within an anatomical passageway (e.g., a sinus ostium (SO), etc.), the user may then pivot actuator levers (464) to a position corresponding to crank pin (455) being located back at position "A," which again corresponds to plunger (467) being at a distal position in body (460). This drives fluid from reservoir (468) to dilator (14) to thereby inflate dilator (14). In some instances, the volumes are all known and predetermined, such that dilator (14) always reaches an appropriate pressure level as soon as plunger (467) reaches a position associated with crank pin (455) being located at position "A." Thus, in some such versions, gauge (462) may be omitted. In some other versions, inflator (450) may permit a fine level of fluid pressure adjustment, via levers (464) or otherwise, after plunger (467) reaches a position associated with crank pin (455) being located at position "A."

Once the user has attained the desired level of pressure in dilator (14) within the anatomical passageway to dilate the anatomical passageway, the user may pause for an approximate, predetermined period of time (e.g., approximately three seconds, etc.). The user may then once again pivot levers (464) to move crank pin (455) back to position "B," which will cause plunger (467) to retract back to the intermediate position, which will in turn withdraw the fluid from dilator (14). With dilator (14) now deflated, dilator (14) may be retracted from the patient. Alternatively, if the user wishes to dilate additional anatomical passageways, dilator

(14) may be positioned in the next anatomical passageway, and the user may repeat the above steps to dilate that next anatomical passageway. Thus, the same volume of fluid within reservoir (468) may be used repeatedly to dilate a plurality of anatomical passageways, without having to withdraw dilator (14) from the patient, and without having to decouple inflator (450) from the rest of system (1), until all of the desired dilations have been completed.

Other suitable variations of inflator (450) will be apparent to those of ordinary skill in the art in view of the teachings herein. Similarly, other suitable ways in which inflator (450) may be used will be apparent to those of ordinary skill in the art in view of the teachings herein.

5. Exemplary Alternative Inflator with Knob Actuated Crankshaft

Figure 10:
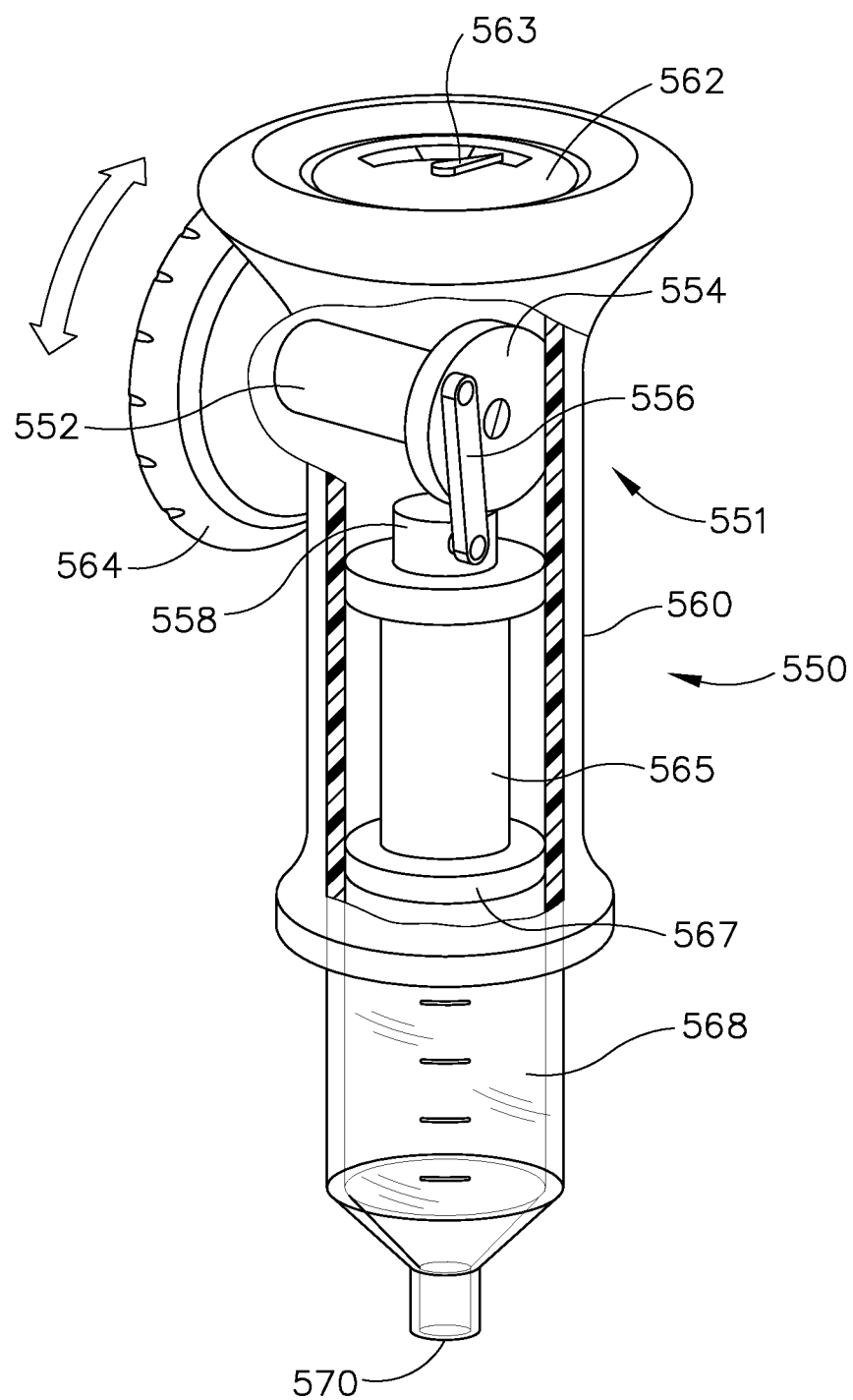
FIG. 10 depicts a perspective view of another exemplary inflator.

FIG. 10 shows another exemplary inflator (550), which is substantially similar to inflator (450) described above. Inflator (550) of this example comprises a body (560), an actuator knob (564), and a pressure gauge (562). Body (560) of the present example is formed as a substantially hollow cylinder, similar to syringe barrel (52) described above, although other suitable configurations may be used. Body (560) comprises a reservoir (568), a distal port (570), and a crank shaft assembly (551) at the proximal end of body (560). A rod (565) is longitudinally driven by crank shaft assembly (551) in a manner similar to rod (465) being driven by crank shaft assembly (451) described above. Plunger (567) is coupled to a distal end of rod (565) and extends outwardly to the inner diameter of body (560) to form a substantially fluid tight seal with body (560). The volume between plunger (567) and the distal end of body (560) forms reservoir (568). Reservoir (568) may be configured to hold about 3 to about 5 cc of fluid (e.g., saline). Rod (565) and plunger (567) may translate proximally and distally to adjust the size of reservoir (568). When rod (565) and plunger (567) translate proximally, the volume of reservoir (568) increases. When rod (565) and plunger (567) translate distally, the volume of reservoir (568) decreases. Port (570) at the distal end of body (560) is in fluid communication with reservoir (568) such that fluid may flow into and out of reservoir (568) via port (570). Port (570) may be coupled with conduit (60) of system (1).

Crank shaft assembly (551) comprises a crank shaft (552) and a crank wheel (554). Crank shaft (552) and crank wheel (554) are coaxial with each other and rotate unitarily with each other. Actuator knob (564) is secured to one end of crank shaft (552). In some other versions, an additional actuator knob (564) may be secured to the other end of crank shaft (552). Actuator knob (564) is operable to rotate crank shaft (552) and crank wheel (554) relative to body (560), about the axis shared by crank shaft (552) and crank wheel (554). A connecting rod (556) is pivotally coupled with an off center crank pin of crank wheel (554); and is further pivotally coupled with a pin at the head (558) of rod (565). These couplings may include bushings, bearings, and/or other features to provide smooth pivoting movement of connecting rod (556) relative to crank wheel (554) and head (558). It should be understood that the configuration of crank shaft assembly (551) will provide reciprocation of rod (565) and plunger (567) in response to rotation of actuator knob (564) relative to body (560).

In the present example, actuator knob (564), crank shaft (552), and crank wheel (554) are operable to rotate through a range of approximately 150°. Alternatively, any other suitable angular range may be provided. In instances providing a limited angular range, the limits may be imposed by bosses or other features that provide hard stops preventing rotation of actuator knob (564), crank shaft (552), and crank wheel (554) beyond the predetermined range. In some versions, there are three predetermined angular positions within the range—such as positions substantially similar to position "A," position "B," and position "C" shown in FIG. 7. These angular positions are associated with the location of the crank pin at particular stages of use of inflator (550) as will be described in greater detail below. It should be understood that inflator (550) may include detent features (and/or some other type of feature(s)) that provide the user with audible and/or tactile feedback to indicate arrival at position "A," position "B," and/or position "C." In some other versions, a detent feature is only used to indicate arrival at position "B," while hard stops indicate arrival at position "A" and position "B." Other suitable forms of feedback will be apparent to those of ordinary skill in the art in view of the teachings herein.

Gauge (562) of the present example is positioned at the proximal end of body (560), and includes a pivoting pin (563) that indicates fluid pressure based on the angular position of the pin. Alternatively, gauge (562) may provide any other suitable type of indication of fluid pressure, including but not limited to the other types of fluid pressure indication described herein. In the present example, gauge (562) is operable to indicate pressure levels up to at least about 12 atmospheres. For instance, some uses of system (1) may include inflation of dilator (14) to a range between about 10 atmospheres and about 12 atmospheres in order to sufficiently dilate a targeted anatomical passageway. Gauge (562) may thus provide the user with real time feedback indicating the fluid pressure within dilator (14) to enable the user to determine whether the desired pressure level has been achieved.

In an exemplary use of inflator (550), a user may start with actuator knob (564) at a position corresponding to the crank pin being located at position "A," which further corresponds to plunger (567) being at a distal position in body (560). The user may then position port (570) in a bowl or other container of saline to draw fluid from. In instances where port (570) is coupled with one end of conduit (60), the user may position the other end of conduit (60) in the saline. In either case, the user may then rotate actuator knob (564) to a position corresponding to the crank pin being located at position "C," which further corresponds to plunger (567) being at a proximal position in body (560). This proximal movement of plunger (567) draws the saline (or other fluid) into reservoir (568). The user may then remove port (570) or conduit (60) from the saline container and rotate actuator knob (564) to a position corresponding to the crank pin being located at position "B," which further corresponds to plunger (567) being at an intermediate position in body (560). It should be understood that transitioning the crank pin from position "A" to position "C" will entail rotating actuator knob (564) in a first direction; while transitioning the crank pin from position "C" to position "B" will entail rotating actuator knob (564) in a second direction. It should also be understood that the distal movement of plunger (567) resulting from the transition of the crank pin from position "C" to position "B" may purge air from reservoir (568). For instance, the user may orient inflator (550) such that port (570) is positioned upwardly to gather air at the top of reservoir (568) before advancing plunger (567) distally in order to purge air from reservoir (568).

Once reservoir (568) has been sufficiently filled with fluid and air has been purged, the user may couple inflator (550)

with dilation catheter (10), such as by coupling port (570) with side arm Luer connector (22) via a flexible conduit (60). With dilator (14) being suitably positioned within an anatomical passageway (e.g., a sinus ostium (SO), etc.), the user may then rotate actuator knob (564) to a position corresponding to the crank pin being located back at position "A," which again corresponds to plunger (567) being at a distal position in body (560). This drives fluid from reservoir (568) to dilator (14) to thereby inflate dilator (14). In some instances, the volumes are all known and predetermined, such that dilator (14) always reaches an appropriate pressure level as soon as plunger (567) reaches a position associated with the crank pin being located at position "A." Thus, in some such versions, gauge (562) may be omitted. In some other versions, inflator (550) may permit a fine level of fluid pressure adjustment, via knob (564) or otherwise, after plunger (567) reaches a position associated with the crank pin being located at position "A."

Once the user has attained the desired level of pressure in dilator (14) within the anatomical passageway to dilate the anatomical passageway, the user may pause for an approximate, predetermined period of time (e.g., approximately three seconds, etc.). The user may then once again rotate knob (564) to move the crank pin back to position "B," which will cause plunger (567) to retract back to the intermediate position, which will in turn withdraw the fluid from dilator (14). With dilator (14) now deflated, dilator (14) may be retracted from the patient. Alternatively, if the user wishes to dilate additional anatomical passageways, dilator (14) may be positioned in the next anatomical passageway, and the user may repeat the above steps to dilate that next anatomical passageway. Thus, the same volume of fluid within reservoir (568) may be used repeatedly to dilate a plurality of anatomical passageways, without having to withdraw dilator (14) from the patient, and without having to decouple inflator (550) from the rest of system (1), until all of the desired dilations have been completed.

Other suitable variations of inflator (550) will be apparent to those of ordinary skill in the art in view of the teachings herein. Similarly, other suitable ways in which inflator (550) may be used will be apparent to those of ordinary skill in the art in view of the teachings herein.

6. Exemplary Alternative Inflator with Knob Actuated Eccentric Cam

Figure 11:
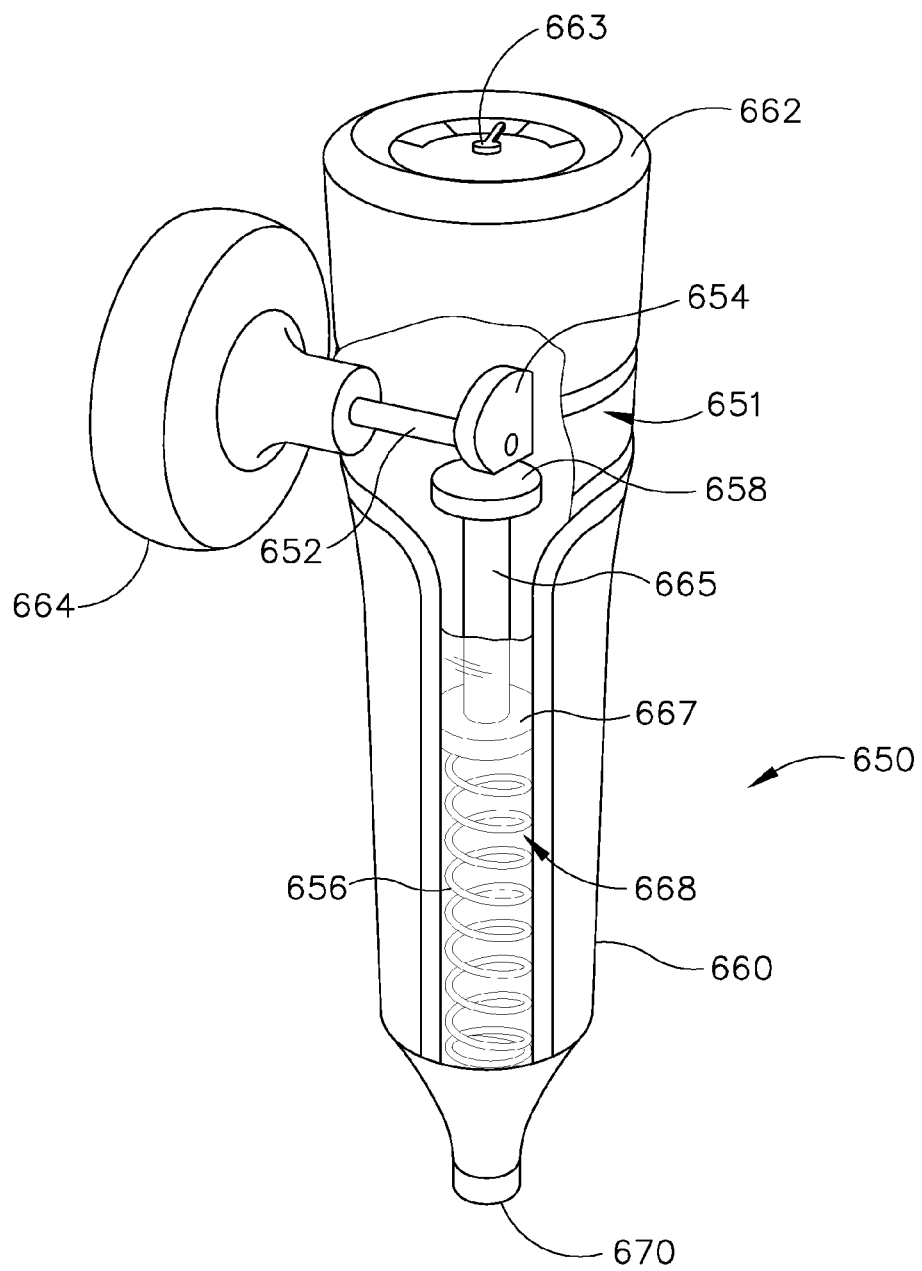
FIG. 11 depicts a perspective view of another exemplary inflator.

FIG. 11 depicts another exemplary inflator (650). Inflator (650) of this example comprises a body (660), an actuator knob (664), and a pressure gauge (662). Body (660) of the present example is formed as a substantially hollow cylinder, similar to syringe barrel (52) described above, although other suitable configurations may be used. Body (660) comprises a reservoir (668), a distal port (670), and a cam drive assembly (651) at the proximal end of body (660). A rod (665) is longitudinally driven by cam drive assembly (651) as will be described in greater detail below. Plunger (667) is coupled to a distal end of rod (665) and extends outwardly to the inner diameter of body (660) to form a substantially fluid tight seal with body (660). The volume between plunger (667) and the distal end of body (660) forms reservoir (668). Reservoir (668) may be configured to hold about 3 to about 5 cc of fluid (e.g., saline). Rod (665) and plunger (667) may translate proximally and distally to adjust the size of reservoir (668). When rod (665) and plunger (667) translate proximally, the volume of reservoir (668) increases. When rod (665) and plunger (667) translate distally, the volume of reservoir (668) decreases. Port (670) at the distal end of body (660) is in fluid communication with reservoir (668) such that fluid may flow into and out of reservoir (668) via port (670). Port (670) may be coupled with conduit (60) of system (1).

Cam drive assembly (651) comprises a cam shaft (652) and a rotary cam (654). Cam shaft (652) and rotary cam (654) rotate unitarily with each other. Actuator knob (664) is secured to one end of cam shaft (652). In some other versions, an additional actuator knob (664) may be secured to the other end of cam shaft (652). Actuator knob (664) is operable to rotate cam shaft (652) and rotary cam (654) relative to body (660), about the axis defined by cam shaft (652). Rotary cam (654) has an asymmetric profile that includes a round section and a flat section. Rotary cam (654) is also eccentrically disposed relative to the longitudinal axis of cam shaft (652). The outer perimeter of rotary cam (654) is positioned to engage a cam plate (658), which is secured to the proximal end of rod (665). A coil spring (656) resiliently biases rod (665) proximally, thereby urging cam plate (658) into engagement with rotary cam (654). While coil spring (656) is located in reservoir (668) in the present example, it should be understood that coil spring (656) may be located elsewhere. For instance, coil spring (656) may be positioned above cam plate (658), and may pull cam plate (658) into engagement with rotary cam (654) instead of pushing cam plate (658) into engagement with rotary cam (654). It should also be understood that any other suitable type of component(s) may be used to provide a resilient bias to cam plate (658), in addition to or in lieu of coil spring (656). In some other versions, a torsion spring is coupled to cam shaft (652) and coil spring (656) is omitted.

In the present example, the asymmetric profile of rotary cam (654) and the eccentric positioning of rotary cam (654) on cam shaft (652) provide translation of cam plate (658), and thereby translation of rod (665) and plunger (667), in response to rotation of knob (664). In some versions, rotary cam (654) includes flats along its perimeter, with such flats corresponding to certain stages of use of inflator (650) similar to those associated with crank pin positions "A," "B," and "C," described above with respect to inflators (450, 550). These flats may also provide tactile feedback to the user. For instance, as the user rotates knob (664) to transition from one stage to another, the user may feel a slight resistance as rotary cam (654) bears against cam plate (658) during the transition from one flat of rotary cam (654) to the next flat. Once the next flat reaches cam plate (658), knob (664) may effectively come to an abrupt stop, providing a sudden change in force required for further rotation. The user may thus sense the arrival at the next operational stage by feeling the change in force through knob (664). Other suitable forms of feedback will be apparent to those of ordinary skill in the art in view of the teachings herein.

Gauge (662) of the present example is positioned at the proximal end of body (660), and includes a pivoting pin (663) that indicates fluid pressure based on the angular position of the pin. Alternatively, gauge (662) may provide any other suitable type of indication of fluid pressure, including but not limited to the other types of fluid pressure indication described herein. In the present example, gauge (662) is operable to indicate pressure levels up to at least about 12 atmospheres. For instance, some uses of system (1) may include inflation of dilator (14) to a range between about 10 atmospheres and about 12 atmospheres in order to sufficiently dilate a targeted anatomical passageway. Gauge (662) may thus provide the user with real time feedback indicating the fluid pressure within dilator (14) to enable the user to determine whether the desired pressure level has been achieved.

In an exemplary use of inflator (650), a user may start with actuator knob (664) at a position corresponding to plunger (667) being located at a distal position in body (660). The user may then position port (670) in a bowl or other container of saline to draw fluid from. In instances where port (670) is coupled with one end of conduit (60), the user may position the other end of conduit (60) in the saline. In either case, the user may then rotate actuator knob (664) to a position corresponding to plunger (667) being located at a proximal position in body (660). In particular, this rotation of knob (664) repositions rotary cam (654) such that a flat or other perimeter feature provides clearance for cam plate (658) to travel proximally, which cam plate (658) does under the resilient bias provided by spring (656). The resulting proximal movement of plunger (667) draws the saline (or other fluid) into reservoir (668). The interaction between cam plate (658) and a flat or other feature on rotary cam (654) may provide tactile feedback to the user via knob (664), indicating that plunger (667) has reached the proximal position. The user may then remove port (670) or conduit (60) from the saline container and rotate actuator knob (664) to a position corresponding to plunger (667) being located at a longitudinally intermediate position in body (660). Again, this rotation of knob (664) repositions rotary cam (654) such that a perimeter feature of rotary cam (654) drives cam plate (658) distally. The resulting distal movement of plunger (667) may purge air from reservoir (668). For instance, the user may orient inflator (650) such that port (670) is positioned upwardly to gather air at the top of reservoir (668) before advancing plunger (667) distally in order to purge air from reservoir (668). The interaction between cam plate (658) and a flat or other feature on rotary cam (654) may provide tactile feedback to the user via knob (664), indicating that plunger (667) has reached the intermediate position.

Once reservoir (668) has been sufficiently filled with fluid and air has been purged, the user may couple inflator (650) with dilation catheter (10), such as by coupling port (670) with side arm Luer connector (22) via a flexible conduit (60). With dilator (14) being suitably positioned within an anatomical passageway (e.g., a sinus ostium (SO), etc.), the user may then rotate actuator knob (664) to a position corresponding to plunger (667) being at a distal position in body (660). Again, this rotation of knob (664) repositions rotary cam (654) such that a perimeter feature of rotary cam (654) drives cam plate (658) distally. The resulting distal movement of plunger (667) drives fluid from reservoir (668) to dilator (14) to thereby inflate dilator (14). The interaction between cam plate (658) and a flat or other feature on rotary cam (654) may provide tactile feedback to the user via knob (664), indicating that plunger (667) has reached the distal position. In some instances, the volumes are all known and predetermined, such that dilator (14) always reaches an appropriate pressure level as soon as rotary cam (654) reaches a position where plunger (667) is driven to a distal-most position. Thus, in some such versions, gauge (662) may be omitted. In some other versions, inflator (650) may permit a fine level of fluid pressure adjustment, via knob (664) or otherwise, after plunger (667) is driven to a distal position associated by rotary cam (654).

Once the user has attained the desired level of pressure in dilator (14) within the anatomical passageway to dilate the anatomical passageway, the user may pause for an approximate, predetermined period of time (e.g., approximately three seconds, etc.). The user may then once again rotate knob (664) to cause plunger (667) to retract back to the intermediate position, which will in turn withdraw the fluid from dilator (14). With dilator (14) now deflated, dilator (14) may be retracted from the patient. Alternatively, if the user wishes to dilate additional anatomical passageways, dilator (14) may be positioned in the next anatomical passageway, and the user may repeat the above steps to dilate that next anatomical passageway. Thus, the same volume of fluid within reservoir (668) may be used repeatedly to dilate a plurality of anatomical passageways, without having to withdraw dilator (14) from the patient, and without having to decouple inflator (650) from the rest of system (1), until all of the desired dilations have been completed.

Other suitable variations of inflator (650) will be apparent to those of ordinary skill in the art in view of the teachings herein. Similarly, other suitable ways in which inflator (650) may be used will be apparent to those of ordinary skill in the art in view of the teachings herein.

7. Exemplary Alternative Inflator with Palm Grip and Thumb Drive

Figure 12:
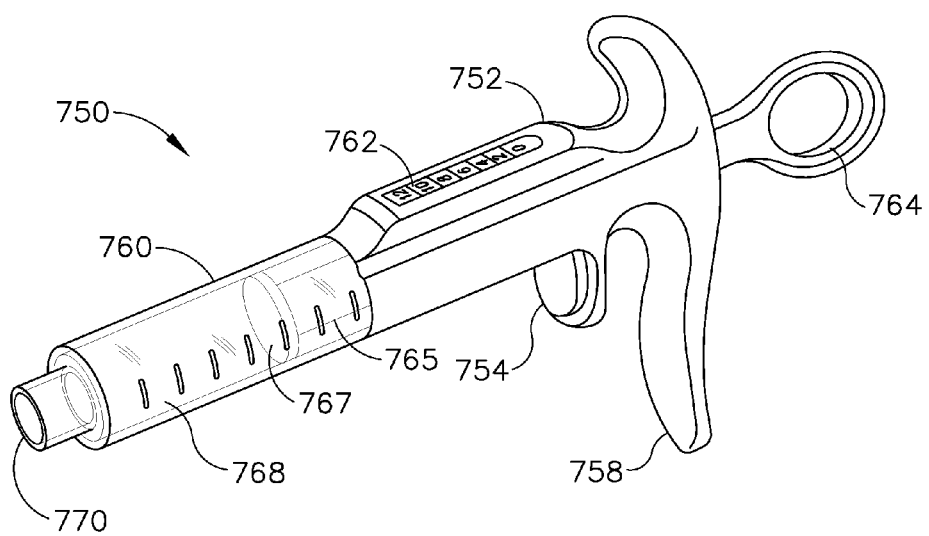
FIG. 12 depicts a perspective view of another exemplary inflator.

FIG. 12 depicts another exemplary inflator (750). Inflator (750) of this example is configured for one-handed operation. Inflator (750) of this example comprises a body (760), an actuator (764), and a pressure gauge (762). Body (760) of the present example is formed as a substantially hollow cylinder, similar to syringe barrel (52) described above, although other suitable configurations may be used. Body (760) comprises a reservoir (768), a distal port (770), and a handle (758) at the proximal end of body (760). A rod (765) extends into body (760). Plunger (767) is coupled to a distal end of rod (765) and extends outwardly to the inner diameter of body (760) to form a substantially fluid tight seal with body (760). The volume between plunger (767) and the distal end of body (760) forms reservoir (768). Reservoir (768) may be configured to hold about 3 to about 5 cc of fluid (e.g., saline). Rod (765) and plunger (767) may translate proximally and distally to adjust the size of reservoir (768). When rod (765) and plunger (767) translate proximally, the volume of reservoir (768) increases. When rod (765) and plunger (767) translate distally, the volume of reservoir (768) decreases. Port (770) at the distal end of body (760) is in fluid communication with reservoir (768) such that fluid may flow into and out of reservoir (768) via port (770). Port (770) may be coupled with conduit (60) of system (1).

Actuator (764) is unitarily secured to rod (765), such that actuator (764) and rod (765) (and, hence, plunger (767)) translate unitarily relative to body (760). In some versions, a coil spring (not shown) and/or some other type of resilient member resiliently biases actuator (764) proximally, though this is of course merely optional. Actuator (764) includes a ring that is configured to receive a user's thumb. Handle (758) of body (760) is configured such that a user may wrap his or her fingers around handle (758) with the thumb of the same hand being disposed in the ring of actuator (764). The user may thus drive actuator (764) distally relative to handle (758), and retract actuator (764) proximally relative to handle (758), using just that single hand. Plunger (767) translates relative to body (760) accordingly.

Inflator (750) of this example also includes a lock/unlock button (754) positioned near handle (758). It should be understood that button (754) may be positioned such that it can be actuated by the same single hand that is being used to hold handle (758) and drive actuator (764), without that hand having to be repositioned to transition among any of those operations. In some versions, inflator (750) includes a locking assembly that will lock the longitudinal position of actuator (764), rod (765), and plunger (767) relative to body (760) unless button (754) is being depressed. For instance, at least part of rod (765) may include sawteeth and/or some other locking feature(s) that are engaged by a pawl or other type of ratcheting feature. The pawl or other type of ratcheting feature may be resiliently biased to engage that part of rod (765), such that the longitudinal position of actuator (764), rod (765), and plunger (767) relative to body (760) will be locked by default. When the user wishes to translate actuator (764), rod (765), and plunger (767) relative to body (760), the user presses button (754) to release the pawl or other type of ratcheting feature from the locking feature(s) of rod (765). Once the desired longitudinal position has been reached, the user may release button (754) to selectively lock actuator (764), rod (765), and plunger (767) at the longitudinal position. As another merely illustrative example, actuator (764), rod (765), and plunger (767) may be configured to translate freely relative to body (760) by default, and button (754) may be configured to lock the longitudinal position of actuator (764), rod (765), and plunger (767) when button (754) is being depressed. Button (754) may thus serve as a brake in such instances. Various suitable ways in which button (754) may selectively lock and/or unlock the longitudinal position of actuator (764), rod (765), and plunger (767) relative to body (760) will be apparent to those of ordinary skill in the art in view of the teachings herein.

Gauge (762) of the present example is positioned proximal to reservoir (768) and is configured to measure the pressure within system (1). Gauge (762) of this example comprises a U-tube type of liquid column gauge or manometer. Graduated markings adjacent to the liquid column in gauge (762) indicate the numerical value of the fluid pressure. Alternatively, gauge (762) may provide any other suitable type of indication of fluid pressure, including but not limited to the other types of fluid pressure indication described herein. In the present example, gauge (762) is operable to indicate pressure levels up to at least about 12 atmospheres. For instance, some uses of system (1) may include inflation of dilator (14) to a range between about 10 atmospheres and about 12 atmospheres in order to sufficiently dilate a targeted anatomical passageway. Gauge (762) may thus provide the user with real time feedback indicating the fluid pressure within dilator (14) to enable the user to determine whether the desired pressure level has been achieved.

In an exemplary use of inflator (750), a user may start with plunger (767) advanced to a distal position in body (760). This may be accomplished by driving actuator (764) toward handle (758) with the user's thumb. The user may then position port (770) in a bowl or other container of saline to draw fluid from. In instances where port (770) is coupled with one end of conduit (60), the user may position the other end of conduit (60) in the saline. In either case, the user may then pull actuator (764) proximally relative to handle (758) with the user's thumb. This will in turn retract plunger (767) relative to body (760) to draw the saline (or other fluid) into reservoir (768). The user may then remove port (770) or conduit (60) from the saline container and advance plunger (767) distally in order to purge air from reservoir (768). For instance, the user may orient inflator (750) such that port (770) is positioned upwardly to gather air at the top of reservoir (768) before advancing plunger (767) distally in order to purge air from reservoir (768).

Once reservoir (768) has been sufficiently filled with fluid and air has been purged, the user may couple inflator (750) with dilation catheter (10), such as by coupling port (770) with side arm Luer connector (22) via a flexible conduit (60). With dilator (14) being suitably positioned within an anatomical passageway (e.g., a sinus ostium (SO), etc.), the user may then drive actuator (764) distally toward handle (758) with the user's thumb, in order to transfer fluid from reservoir (768) to dilator (14). The user may observe the pressure reading at gauge (762) while advancing actuator (764) distally in order to determine when the appropriate fluid pressure level has been reached.

Once the user has attained the desired level of pressure in dilator (14) within the anatomical passageway to dilate the anatomical passageway, the user may pause for an approximate, predetermined period of time (e.g., approximately three seconds, etc.). The user may then pull actuator (764) proximally relative to handle (758) with the user's thumb. This will in turn retract plunger (767) relative to body (760) to draw fluid from dilator (14). With dilator (14) now deflated, dilator (14) may be retracted from the patient. Alternatively, if the user wishes to dilate additional anatomical passageways, dilator (14) may be positioned in the next anatomical passageway, and the user may repeat the above steps to dilate that next anatomical passageway. Thus, the same volume of fluid within reservoir (768) may be used repeatedly to dilate a plurality of anatomical passageways, without having to withdraw dilator (14) from the patient, and without having to decouple inflator (750) from the rest of system (1), until all of the desired dilations have been completed.

In some instances, rod (765) and body (760) include complementary detent features (and/or some other type of feature(s)) that provide the user with audible and/or tactile feedback. For instance, such features may provide the user with feedback to indicate longitudinal positions of plunger (767) that are predeterminedly associated with an appropriate pressure level in dilator (14). In addition or in the alternative, such features may provide the user with feedback to indicate that the longitudinal position of plunger (767) is getting close to a position that is predeterminedly associated with an appropriate pressure level in dilator (14), thereby alerting the user to slow their distal advancement of actuator (764) and carefully watch gauge (762). Detent features (and/or some other type of feature(s)) may also provide the user with audible and/or tactile feedback to indicate when plunger (767) has reached a position that is predeterminedly associated with air being purged from reservoir (768) before port (770) is coupled with side arm Luer connector (22). Other suitable variations of inflator (750) will be apparent to those of ordinary skill in the art in view of the teachings herein. Similarly, other suitable ways in which inflator (750) may be used will be apparent to those of ordinary skill in the art in view of the teachings herein.

8. Exemplary Alternative Inflator with Rotary Drive and Button Release

Figure 13:
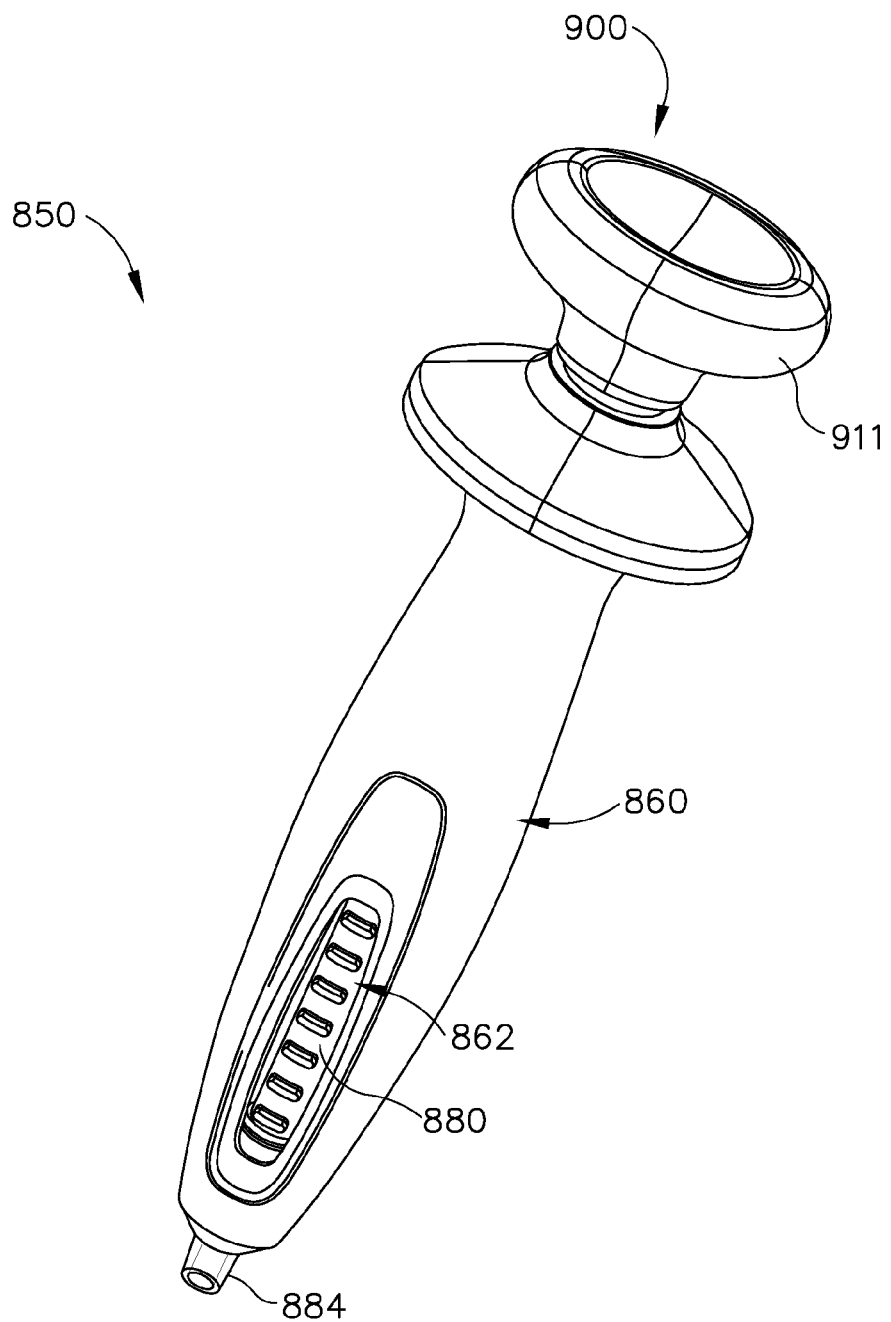
FIG. 13 depicts a perspective view of another exemplary inflator.
Figure 14:
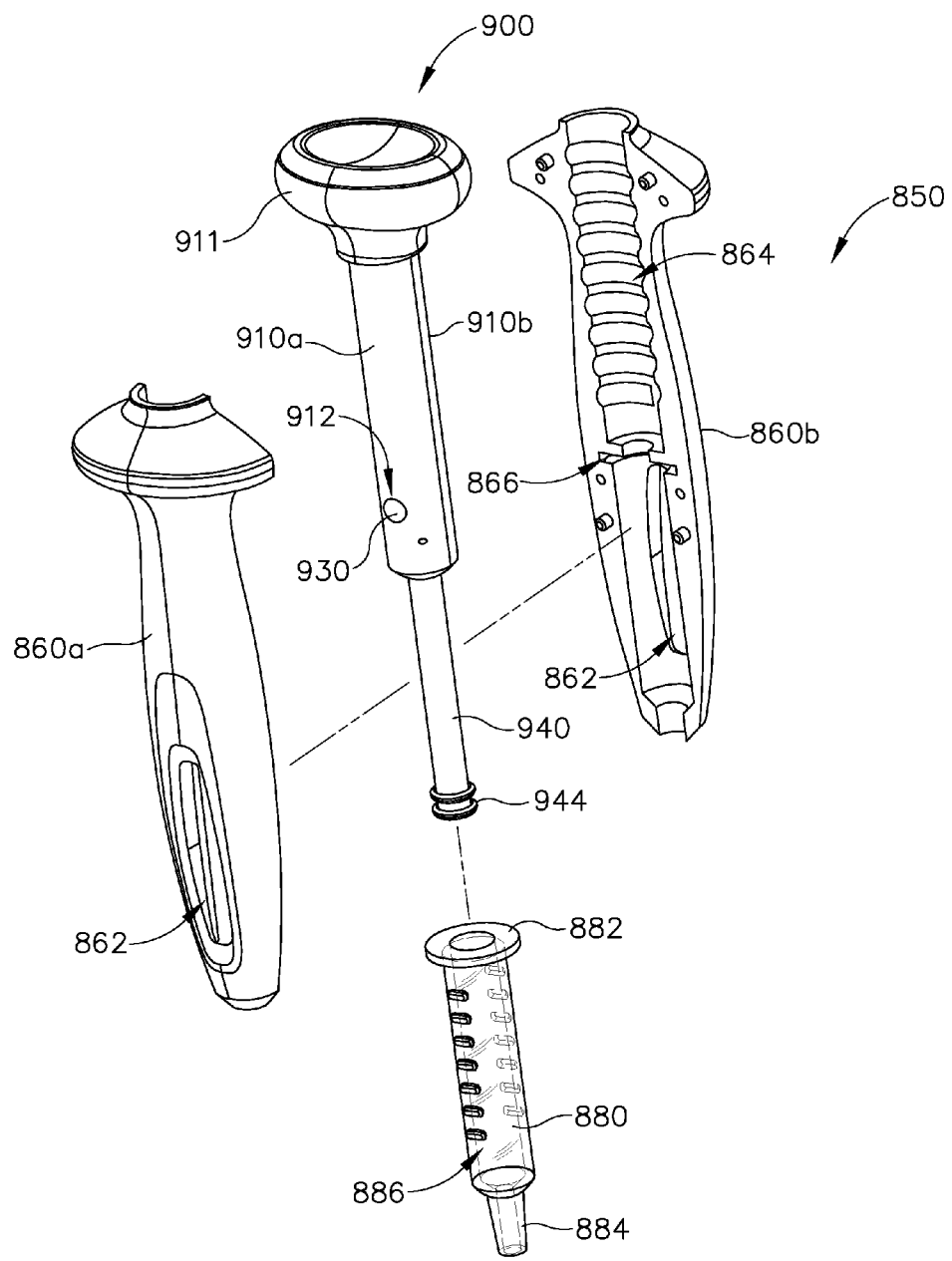
FIG. 14 depicts an exploded view of the inflator of FIG. 13.
Figure 15:
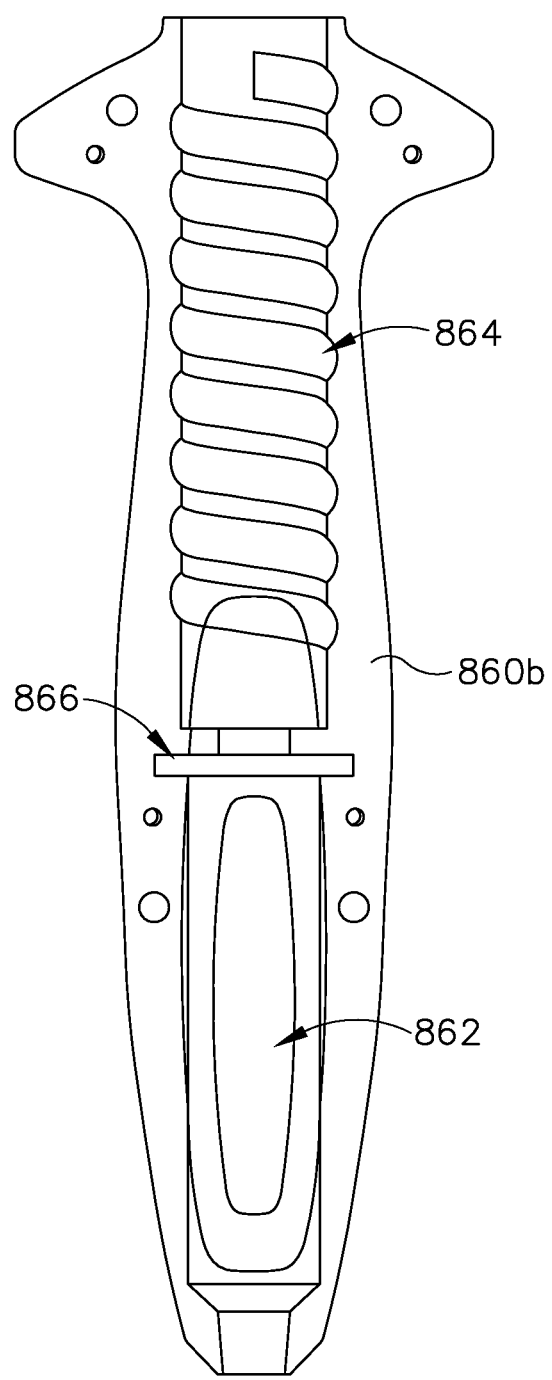
FIG. 15 depicts a side elevational view of a housing half of the inflator of FIG. 13.

FIGS. 13-17C depict another exemplary inflator (850). Inflator (850) of this example includes a housing (860), a syringe barrel (880), and a plunger actuation assembly (900). Housing (860) is formed by two halves (860a, 860b) that are joined together to contain syringe barrel (880) and plunger actuation assembly (900). As best seen in FIGS. 13-15, each half (860a, 860b) includes a window (862) that permits viewing of syringe barrel (880). In particular, a user of inflator (850) may see how much fluid is in syringe barrel (880) by viewing syringe barrel (880) through window (862). As best seen in FIG. 15, each half (860a, 860b) also includes a respective helically oriented groove (864) and flange recess (866). Grooves (864) of halves (860a, 860b) are configured to align with each other when halves (860a, 860b) are joined, to form a continuous helical thread in housing (860). Flange recesses (866) of halves (860a, 860b) are configured to align with each other when halves (860a, 860b) are joined, to capture and retain the upper flange (882) of syringe barrel (880). The distal port (884) of syringe barrel (880) protrudes from housing (860). Distal port (884) is configured to communicate fluid to and from the reservoir (886) defined by syringe barrel (880).

Figure 16:
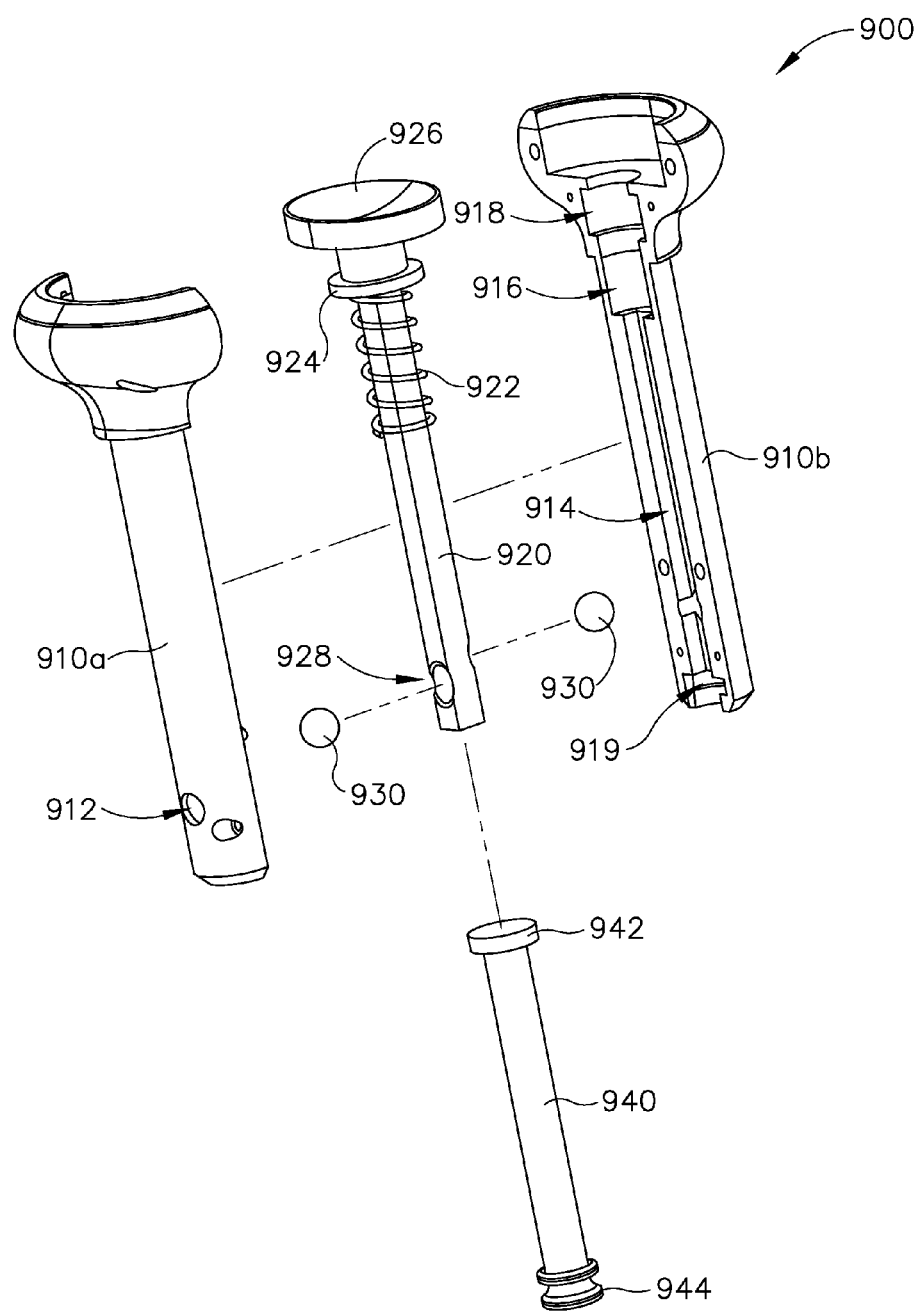
FIG. 16 depicts an exploded view of a plunger actuation assembly of the inflator of FIG. 13.

As shown in FIGS. 14 and 16, plunger actuation assembly (900) of this example comprises a pair of rotary actuator halves (910a, 910b), a translating rod (920), a pair of ball bearings (930), and a plunger (940). Rotary actuator halves (910a, 910b) cooperate to define a knob (911) when halves (910a, 910b) are assembled together. Each half (910a, 910b) has a respective bearing aperture (912), rod recess (914), spring recess (916), and a rod flange recess (918). Bearing apertures (912) are configured to enable portions of bearings (930) to protrude through apertures (912) without letting bearings (930) pass fully through apertures (912) when plunger actuation assembly (900) is assembled. When halves (910a, 910b) are assembled together, rod recesses (914) cooperate to slidingly receive rod (920), enabling rod to translate longitudinally relative to assembled halves (910a, 910b). Spring recesses (916) align with each other to capture the distal end of a spring (922), which is configured to resiliently bias rod (920) upwardly relative to assembled halves (910a, 910b). Rod flange recesses (918) together encompass a flange (924) of rod (920) and thereby constrain longitudinal movement of rod (920) relative to assembled halves (910a, 910b) while still permitting some degree of longitudinal movement of rod (920) relative to assembled halves (910a, 910b). As will be described in greater detail below, such translation of rod (920) selectively unlocks engagement between bearings (930) and grooves (864).

Each rotary actuator half (910a, 910b) also includes a plunger flange recess (919). Plunger flange recesses (919) cooperate to capture a proximal flange (942) of plunger (940). Plunger (940) thus translates unitarily with assembled halves (910a, 910b) relative to housing (860) and relative to syringe barrel (880). A piston (944) at the distal end of plunger (940) is positioned within syringe barrel (880). As also noted above, syringe barrel (880) is secured by housing (860). It should therefore be understood that plunger (940) is configured to reciprocate within syringe barrel (880) to selectively vary the volume of reservoir (886) in syringe barrel (880), to thereby draw fluid into or expel fluid from reservoir (886).

Figure 17A:
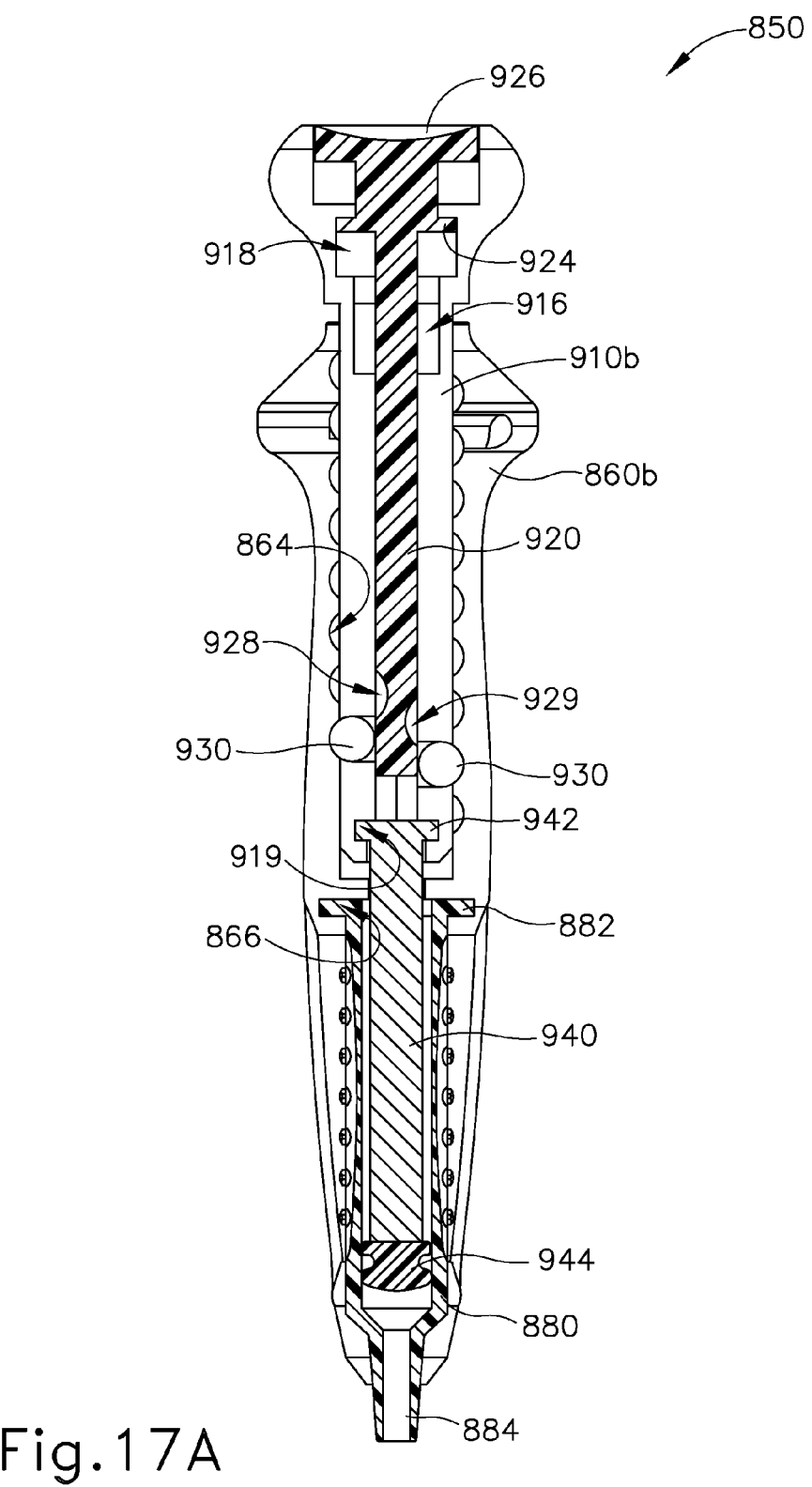
FIG. 17A depicts a cross-sectional side view of the inflator of FIG. 13, with the plunger actuation assembly in a distal and locked position.
Figure 17B:
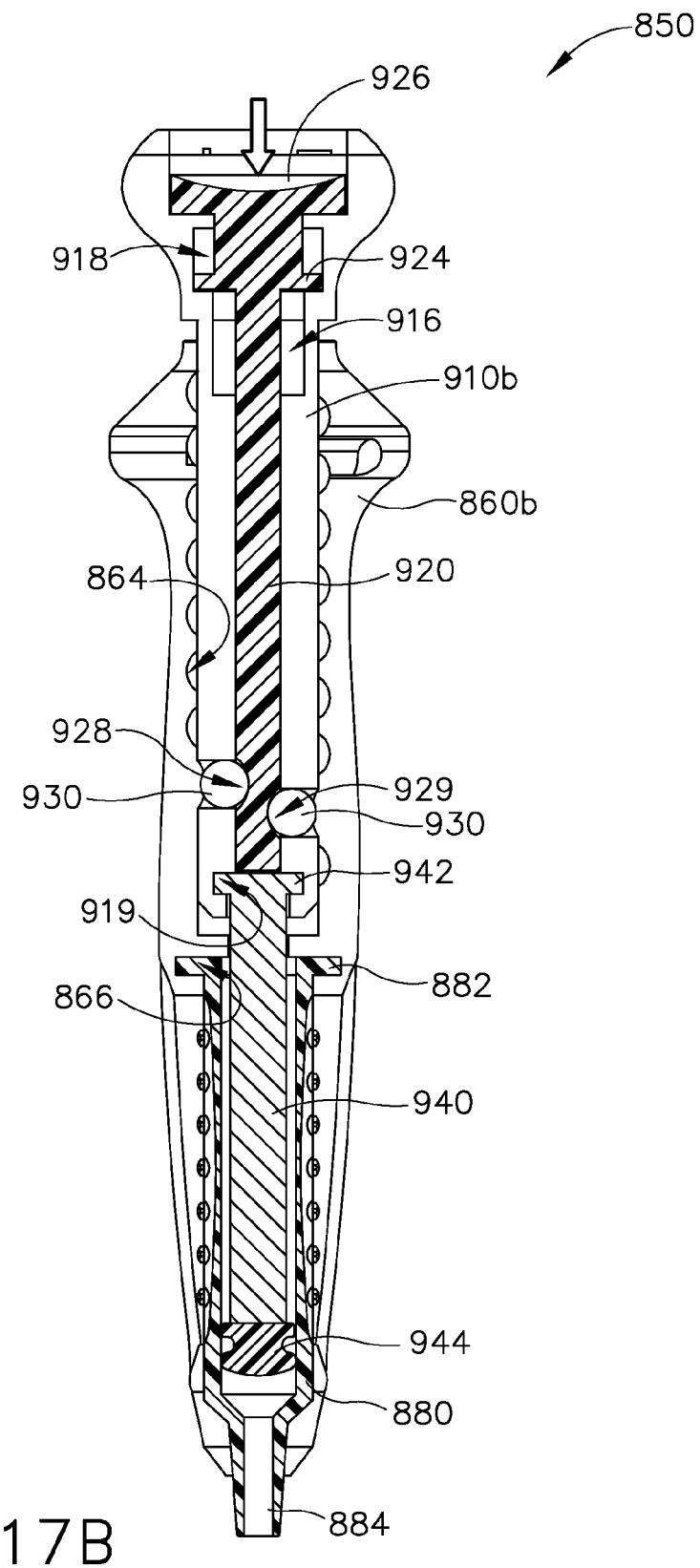
FIG. 17B depicts a cross-sectional side view of the inflator of FIG. 13, with the plunger actuation assembly in a distal and unlocked position.

As noted above, translating rod (920) of the present example comprises a spring (922) and a flange (924). While spring (922) of the present example comprises a coil spring, it should be understood that any other suitable type of resilient member may be used to resiliently bias rod (920). Rod (920) of the present example further includes a pushbutton (926), a first lateral recess (928), and a second lateral recess (929). Lateral recesses (928, 929) are positioned just proximal to the distal end of rod (920), and are sized to receive portions of bearings (930) when rod (920) is translated to a distal position as shown in FIG. 17B. Rod (920) is configured such that rod (920) drives bearings (930) outwardly when rod (920) is in a proximal position as shown in FIG. 17A (in which spring (922) is omitted). When bearings (930) are in this position, bearings (930) protrude through apertures (912) and engage grooves (864). When bearings (930) are engaged with grooves (864), bearings (930) prevent plunger actuation assembly (900) from translating freely relative to housing (860). However, the relationship between bearings (930) and the helical threading formed by grooves (864) will provide translation of plunger actuation assembly (900) when plunger actuation assembly (900) is rotated relative to housing (860). When rod (920) is translated to the distal position shown in FIG. 17B, bearings (930) retract into recesses (928, 929), disengaging grooves (864). When bearings (930) are disengaged from grooves (864), plunger actuation assembly (900) translates freely relative to housing (860). While grooves (928, 929) are longitudinally offset relative to each other in the present example, it should be understood that grooves (928, 929) may alternatively be located at a common longitudinal position.

Figure 17C:
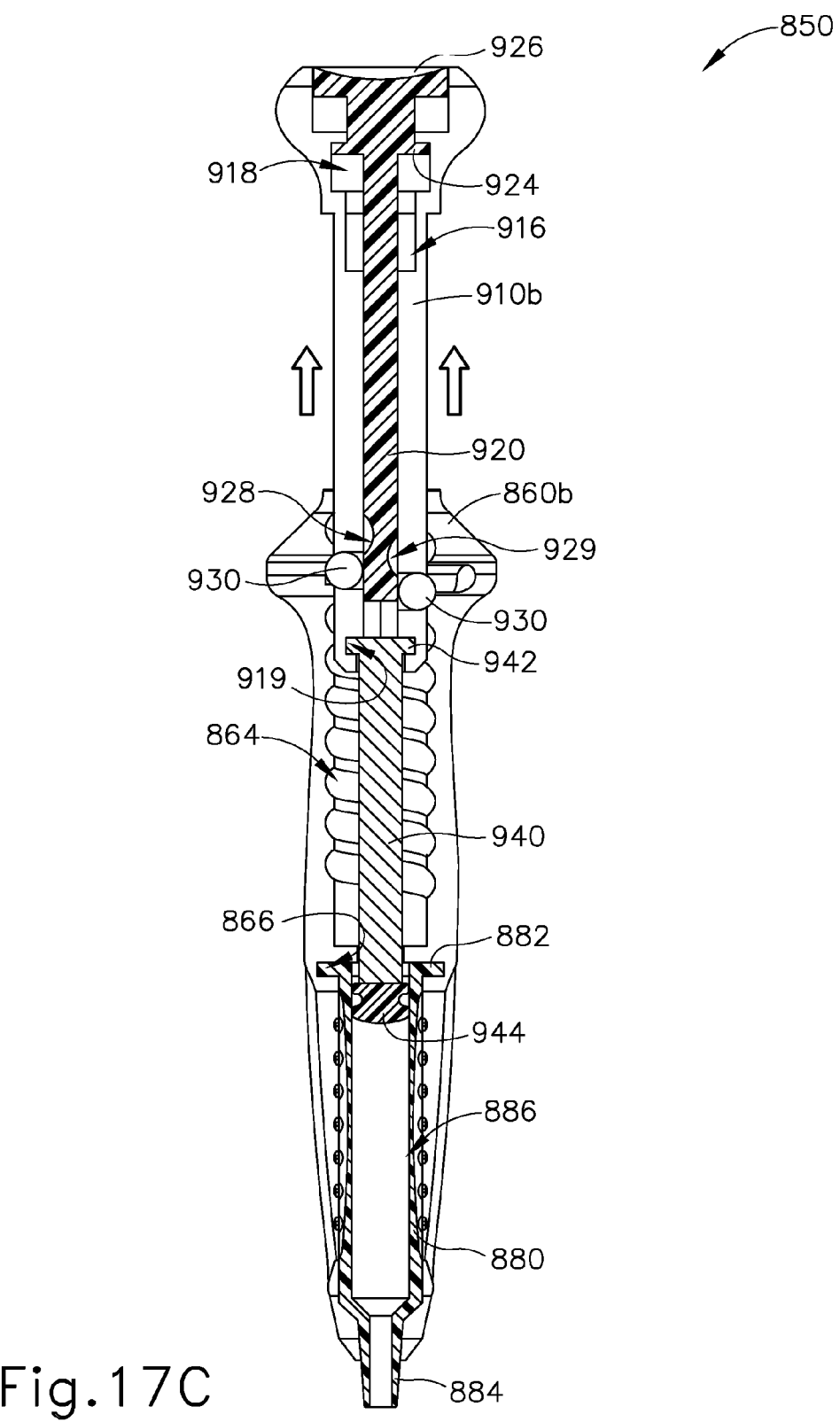
FIG. 17C depicts a cross-sectional side view of the inflator of FIG. 13, with the plunger actuation assembly in a proximal and locked position.
Figure 18:
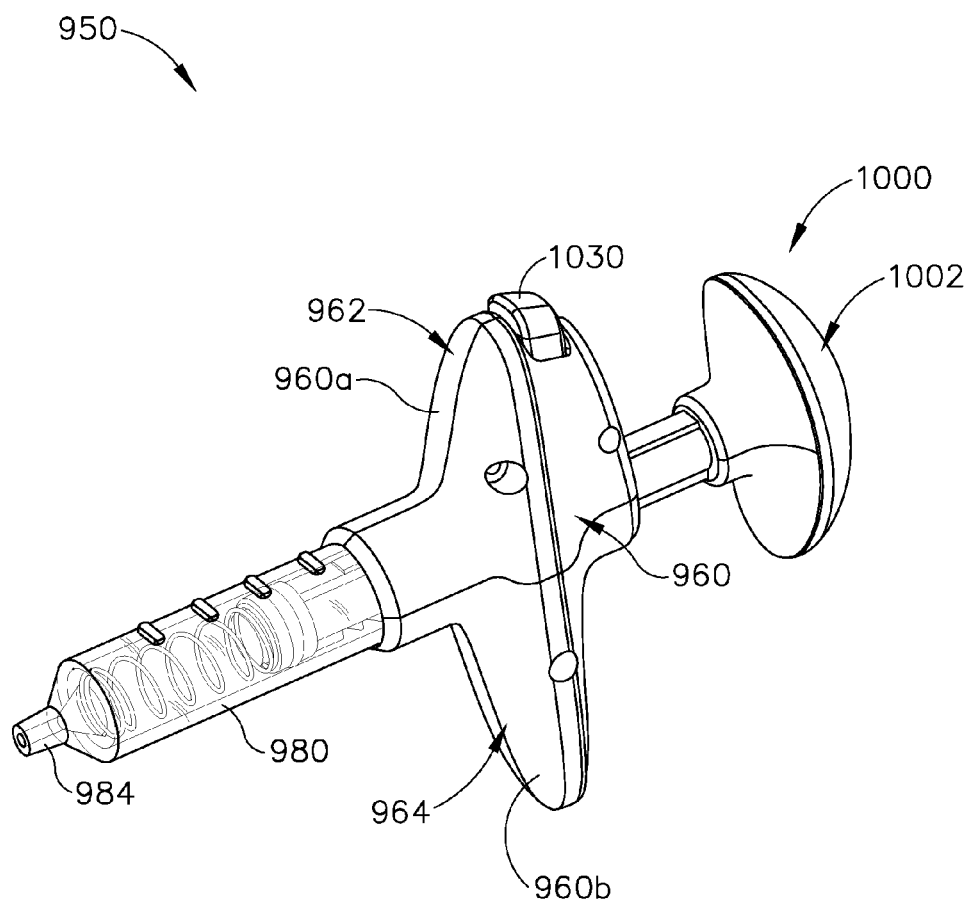
FIG. 18 depicts a perspective view of another exemplary inflator.

In an exemplary use of inflator (850), a user may start with plunger (940) advanced to a distal position as shown in FIG. 17A. The user may then position port (884) in a bowl or other container of saline to draw fluid from. In instances where port (884) is coupled with one end of conduit (60), the user may position the other end of conduit (60) in the saline. In either case, the user may then advance rod (920) distally by pushing on pushbutton (926), thereby disengaging bearings (930) from grooves (864) as shown in FIG. 17B. Next, the user may pull plunger actuation assembly (900) proximally relative to housing (860), which will in turn retract plunger (940) relative to syringe barrel (880) to draw the saline (or other fluid) into reservoir (886). The user may then remove port (884) or conduit (60) from the saline container and release pushbutton (926). This will enable spring (922) to drive rod (920) upwardly relative to halves (910a, 910b), which will result in rod (920) driving bearings (930) outwardly into engagement with grooves (864) as shown in FIG. 17C.

At this stage, the user may advance plunger (940) distally in order to purge air from reservoir (886). For instance, the user may orient inflator (850) such that port (884) is positioned upwardly to gather air at the top of reservoir (886) before advancing plunger (940) distally in order to purge air from reservoir (886). To purge air from reservoir (886), the user may depress pushbutton (926) again to disengage bearings (930) from grooves (864), then push plunger actuation assembly (900) distally relative to housing (860) to advance plunger (940) within syringe barrel (880). Alternatively, the user may refrain from depressing pushbutton (926), and may instead rotate knob (911) relative to housing (860). Due to the engagement between bearings (930) and grooves (864) this rotation of knob (911) relative to housing (860) will drive plunger actuation assembly (900) distally relative to housing (860), thereby advancing plunger (940) within syringe barrel (880).

Once reservoir (886) has been sufficiently filled with fluid and air has been purged, the user may couple inflator (850) with dilation catheter (10), such as by coupling port (884) with side arm Luer connector (22) via a flexible conduit (60). In some instances, a conventional fluid pressure gauge (not shown) may be coupled in the fluid path between port (884) and side arm Luer connector (22) (e.g., via a "T" fitting, etc.). Of course, inflator (850) may alternatively include an integral pressure gauge. With dilator (14) being suitably positioned within an anatomical passageway (e.g., a sinus ostium (SO), etc.), the user may then advance plunger actuation assembly (900) distally relative to housing (860) to advance plunger (940) within syringe barrel (880), thereby transferring fluid from reservoir (886) to dilator (14). The user may observe the pressure reading at the pressure gauge while advancing plunger actuation assembly (900) distally in order to determine when the appropriate fluid pressure level has been reached.

In some instances, the advancement of plunger actuation assembly (900) occurs in two stages. In the first stage, the user may depress pushbutton (926) again to disengage bearings (930) from grooves (864), then push plunger actuation assembly (900) distally relative to housing (860) to advance plunger (940) within syringe barrel (880) through a first range of motion that approaches but does not quite reach the desired fluid pressure. In the second stage, the user may release pushbutton (926) to re-engage bearings (930) with grooves (864), then rotate knob (911) relative to housing (860) to drive plunger actuation assembly (900) distally relative to housing (860), thereby advancing plunger (940) within syringe barrel (880) through a second range of motion in a more precisely controlled fashion until reaching the desired fluid pressure.

Once the user has attained the desired level of pressure in dilator (14) within the anatomical passageway to dilate the anatomical passageway, the user may pause for an approximate, predetermined period of time (e.g., approximately three seconds, etc.). The user may then depress pushbutton (926) to once again disengage bearings (930) from grooves (864), then pull plunger actuation assembly (900) proximally relative to housing (860). This will retract plunger (940) relative to syringe barrel (880), thereby drawing fluid from dilator (14). With dilator (14) now deflated, dilator (14) may be retracted from the patient. Alternatively, if the user wishes to dilate additional anatomical passageways, dilator (14) may be positioned in the next anatomical passageway, and the user may repeat the above steps to dilate that next anatomical passageway. Thus, the same volume of fluid within reservoir (886) may be used repeatedly to dilate a plurality of anatomical passageways, without having to withdraw dilator (14) from the patient, and without having to decouple inflator (850) from the rest of system (1), until all of the desired dilations have been completed. Other suitable variations of inflator (850) will be apparent to those of ordinary skill in the art in view of the teachings herein. Similarly, other suitable ways in which inflator (850) may be used will be apparent to those of ordinary skill in the art in view of the teachings herein.

9. Exemplary Alternative Inflator with Ratcheting Drive and Button Release

FIGS. 18-21E depict another exemplary inflator (950). Inflator (950) of this example includes a housing (960), a syringe barrel (980), and a plunger actuator (1000). Housing (960) is formed by two halves (960a, 960b) that are joined together to contain syringe barrel (980) and plunger actuator (1000). Housing (960) defines two finger grip features (962, 964) while the proximal end of plunger actuator (1000) includes a palm grip feature (1002). These grip features (962, 964, 1002) are configured to enable a user to grasp and manipulate inflator (950) with a single hand by wrapping their fingers about finger grip features (962, 964) while positioning palm grip feature (1002) in the palm of the same hand. As will be described in greater detail below, inflator (950) may be selectively actuated by the user squeezing their hand to drive plunger actuator (1000) distally relative to housing (960); or by releasing their grip to enable plunger actuator (1000) to retract proximally relative to housing (960).

Figure 19:
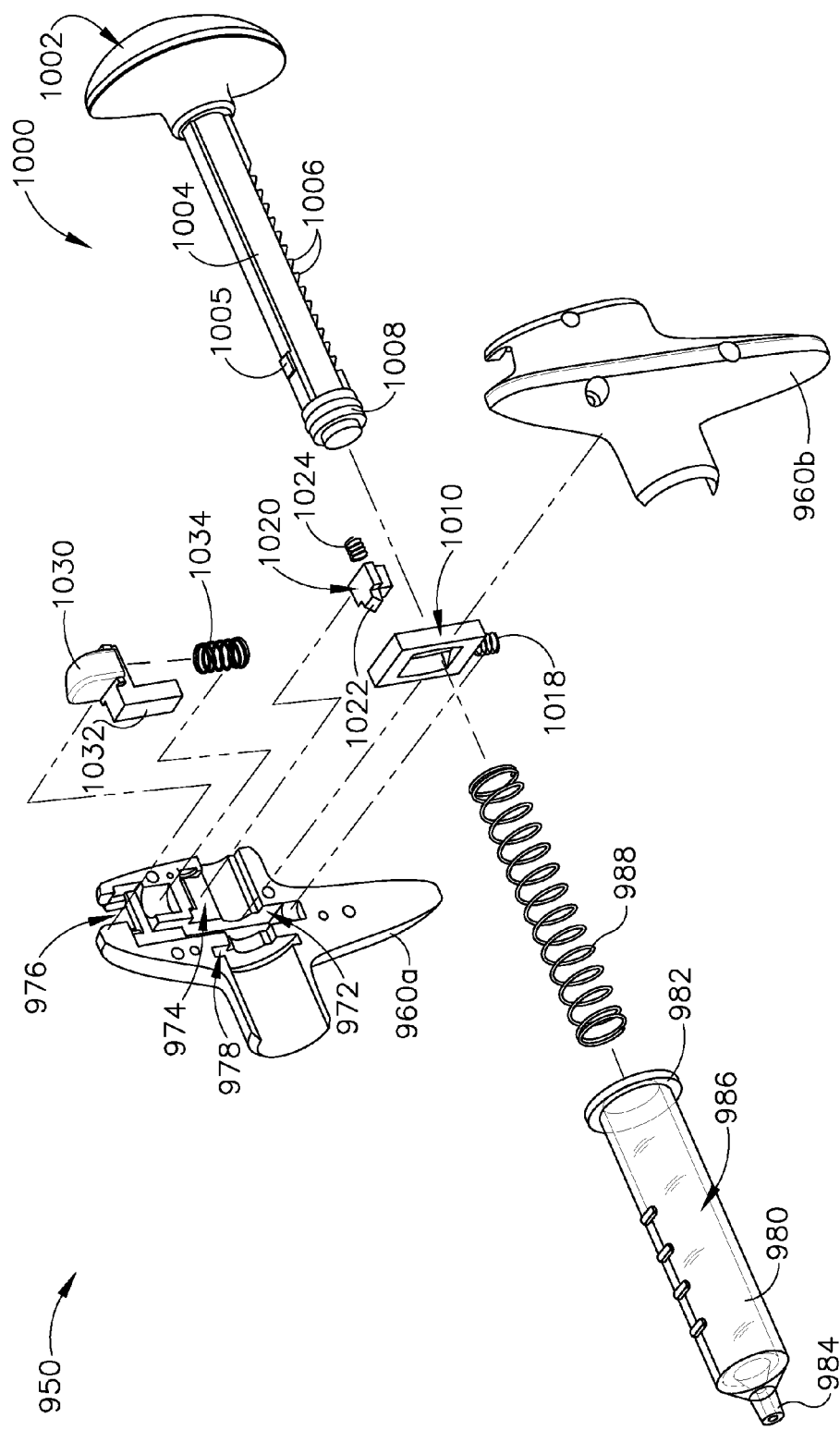
FIG. 19 depicts an exploded view of the inflator of FIG. 18.

As best seen in FIG. 19, each housing half (960a, 960b) defines a corresponding ratcheting block recess (972), a block latch recess (974), a pushbutton recess (976), and a flange recess (978). Ratcheting block recesses (972) cooperate to receive a ratcheting block (1010) and associated spring (1018). Spring (1018) biases ratcheting block (1010) upwardly within recess (972). Block latch recesses (974) cooperate to receive a block latch (1020) and associated spring (1024). Spring (1024) biases block latch (1020) distally within recess (974). Pushbutton recesses (976) cooperate to receive a pushbutton (1030) and associated spring (1034). Spring (1034) biases pushbutton (1030) upwardly within recess (972). While springs (1018, 1024, 1034) all comprise coil springs in the present example, it should be understood that any other suitable types of resilient components or features may be used. Flange recesses (978) cooperate to receive upper flange (982) of syringe barrel (980), thereby fixedly securing syringe barrel (980) to housing (960). Other suitable features and configurations for housing (960) will be apparent to those of ordinary skill in the art in view of the teachings herein.

FIG. 19 also shows additional features of plunger actuator (1000). In particular, plunger actuator (1000) of this example comprises a shaft (1004) extending distally from palm grip feature (1002), with a set of sawteeth (1006) on the underside of shaft (1004). Shaft (1004) also includes a latch engagement feature (1005) projecting from the upper side of shaft (1004). Latch engagement feature (1005) is configured to interact with latch (1020) as will be described in greater detail below. Shaft terminates in a piston (944), which is positioned within syringe barrel (980). Plunger actuator (1000) is operable to translate relative to housing (960), to thereby reciprocate piston (944) within syringe barrel (980). It should be understood that such reciprocation will selectively vary the volume of reservoir (986) in syringe barrel (980), to thereby draw fluid into or expel fluid from reservoir (986). As shown in FIGS. 19 and 21A-21E, a spring (988) is positioned inside reservoir (986), between the distal face of piston (1008) and the distal interior wall of reservoir (986), to bias plunger actuator (1000) proximally relative to syringe barrel (980). While spring (988) comprises a coil spring in the present example, any other suitable type of resilient member may be used. Furthermore, spring (988) may be positioned elsewhere in inflator (950).

Figure 20:
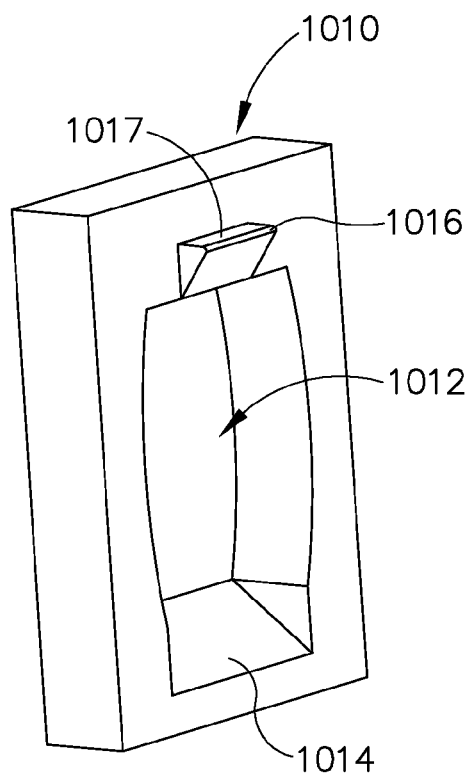
FIG. 20 depicts a perspective view of a ratchet block of the inflator of FIG. 18.

FIG. 20 shows the proximal side of ratcheting block (1010). As shown, ratcheting block (1010) defines an aperture (1012) that is sized and configured to receive shaft (1004) of plunger actuator (1000). A pawl feature (1014) is located at the bottom of aperture (1012) and is shaped to complement sawteeth (1006) of shaft (1004). A latch cam feature (1016) is located at the top of aperture (1012) and is shaped to complement a cam feature (1022) of block latch (1020). As will be described in greater detail below, ratcheting block (1010) is operable to permit plunger actuator (1000) to freely translate from a proximal position to a distal position; while preventing plunger actuator (1000) from retracting proximally when plunger actuator (1000) is released during translation from the proximal position to the distal position. As will also be described in greater detail below, block latch (1020) is configured to keep ratcheting block (1010) disengaged from plunger actuator (1000) after pushbutton (1030) is actuated, until plunger actuator (1000) reaches a proximal home position.

Figure 21A:
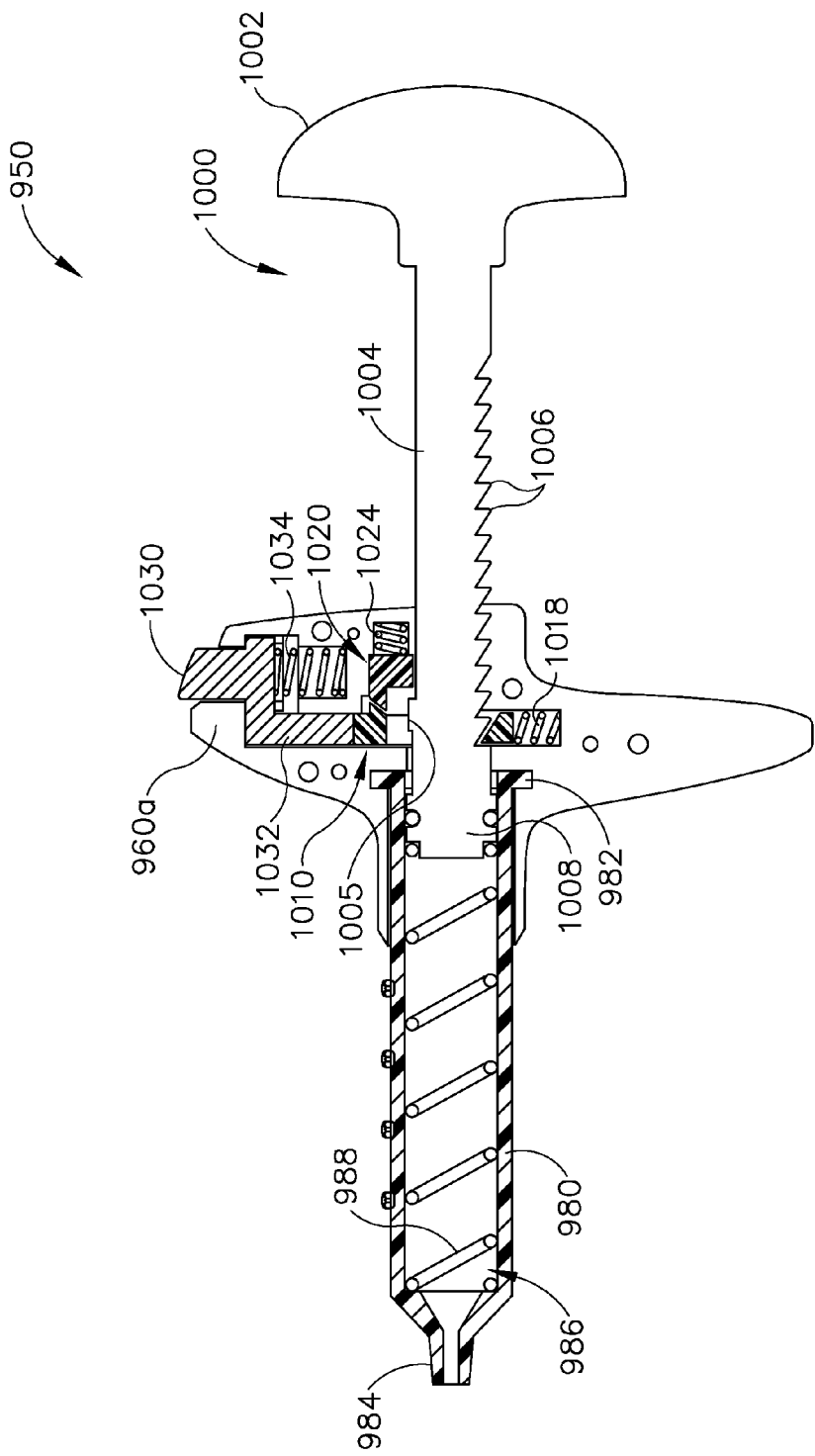
FIG. 21A depicts a cross-sectional side view of the inflator of FIG. 18, with the plunger in a proximal position.
Figure 21B:
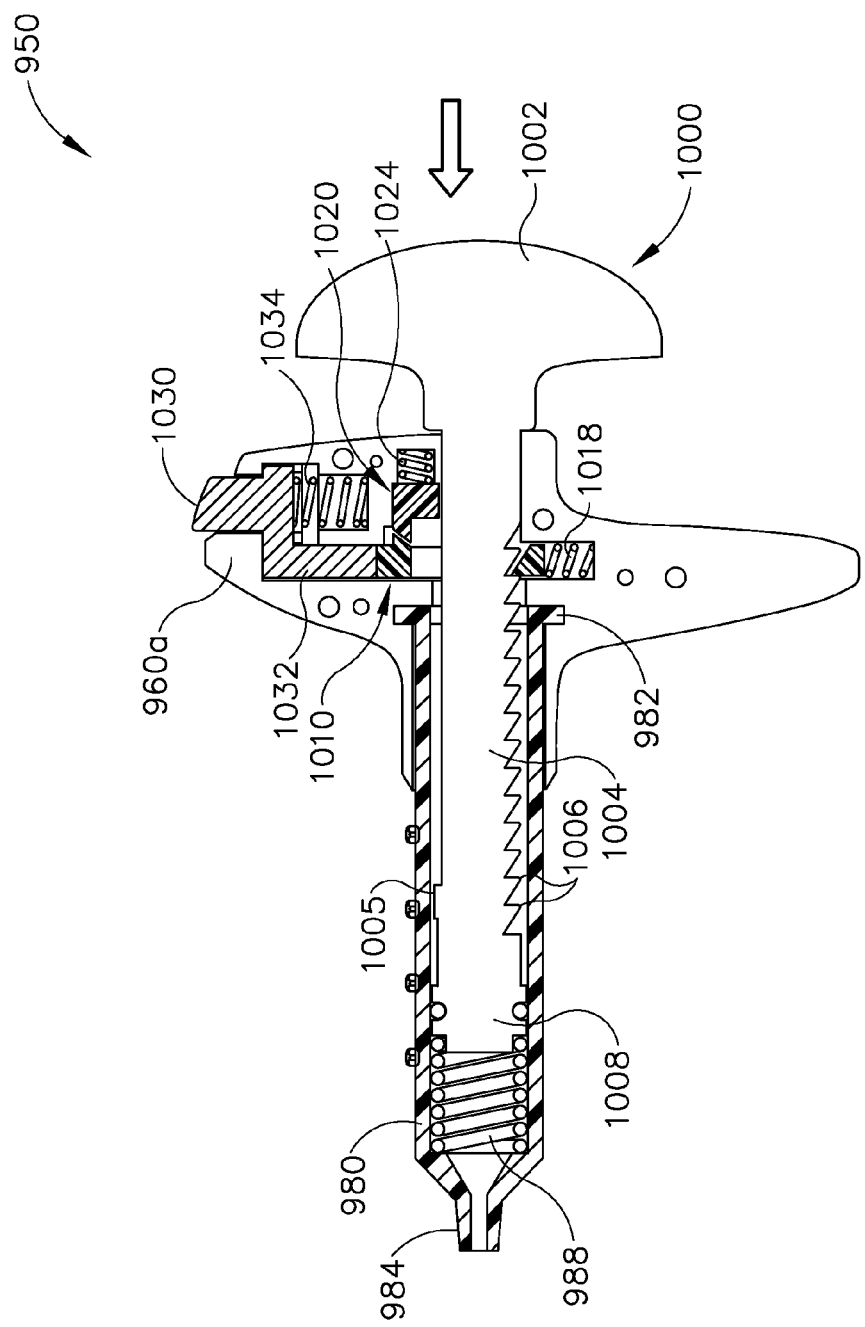
FIG. 21B depicts a cross-sectional side view of the inflator of FIG. 18, with the plunger in a distal position.

FIGS. 21A-21E depict a series showing interactions between the above-described components during operation of inflator (950). In particular, FIG. 21A shows plunger actuator (1000) in a proximal position. Ratcheting block (1010) is in an upper position and pushbutton (1030) is also in an upper position. Block latch (1020) is in a distal position. FIG. 21B shows plunger actuator (1000) advanced to a distal position. Ratcheting block (1010) remains in an upper position, pushbutton (1030) remains in an upper position, and block latch (1020) remains in a distal position. During the advancement of plunger actuator (1000) from the proximal position (FIG. 21A) to the distal position (FIG. 21B), pawl feature (1014) ratchets along sawteeth (1006) due to the resilient bias of spring (1018). If the user were to relax their grip on grip features (962, 964, 1002) during advancement of plunger actuator (1000), engagement between pawl feature (1014) and sawteeth (1006) would prevent plunger actuator (1000) from moving proximally, despite the proximally directed bias from spring (988). Plunger actuator (1000) would thus maintain its longitudinal position relative to housing (960) and also maintain its position after reaching the stage shown in FIG. 21B, until the user depresses pushbutton (1030).

Figure 21C:
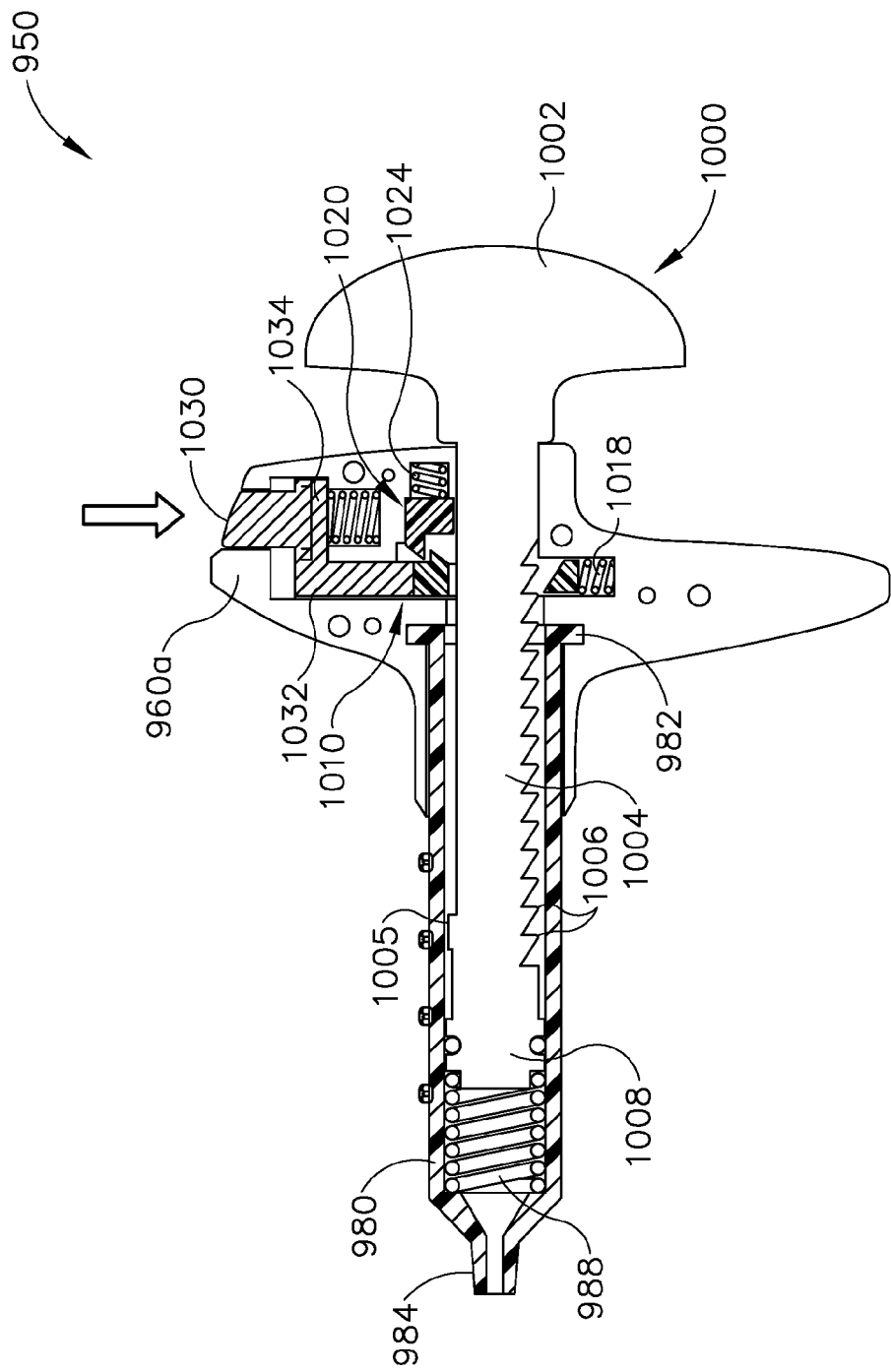
FIG. 21C depicts a cross-sectional side view of the inflator of FIG. 18, with the plunger in a distal position, and with a button actuated to release the ratchet block from the plunger driver.
Figure 21D:
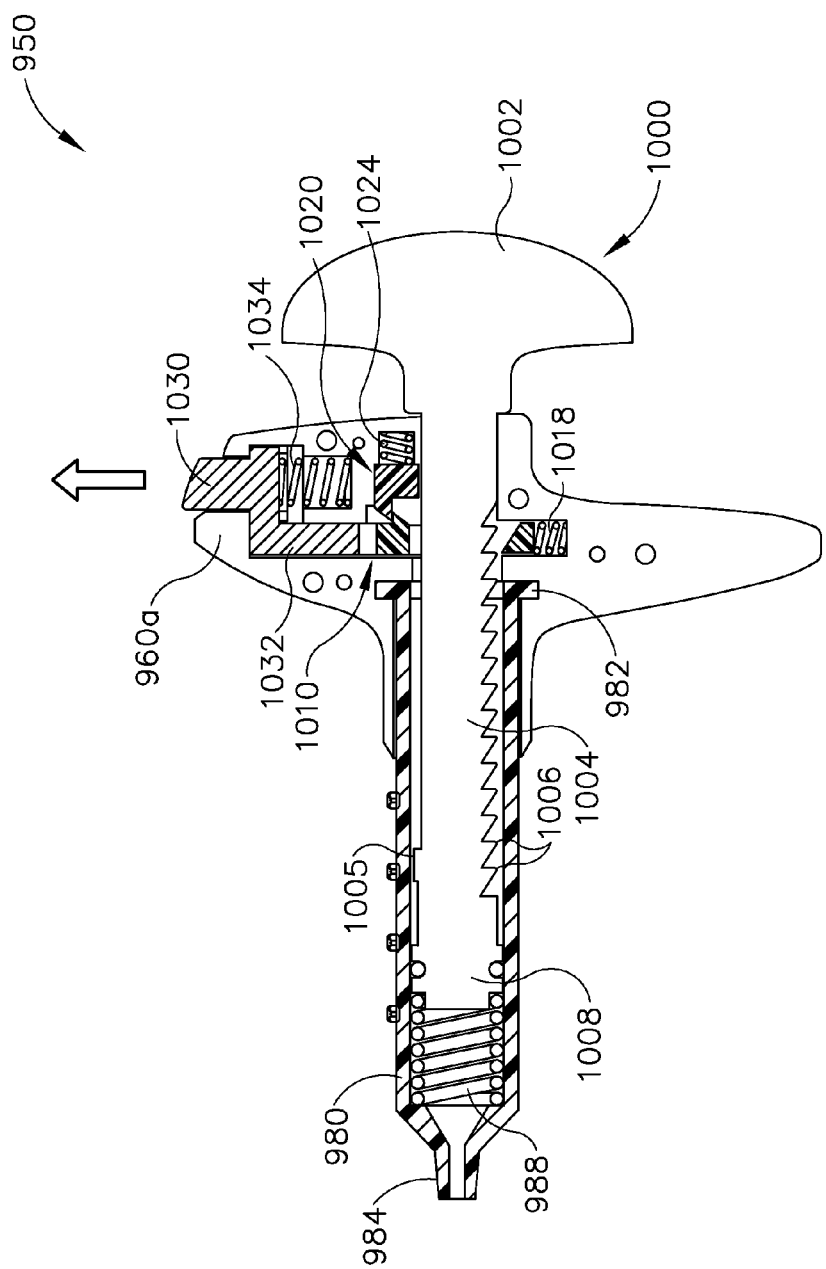
FIG. 21D depicts a cross-sectional side view of the inflator of FIG. 18, with the plunger in a distal position, with the button released, and with a latch holding the ratchet block in a position where the ratchet block remains disengaged from the plunger driver.

Pushbutton (1030) includes an integral, downwardly oriented projection (1032) that is operable to drive ratcheting block (1010) downwardly when pushbutton (1030) is pushed downwardly. As shown in FIG. 21C, the resulting downward movement of ratcheting block (1010) disengages pawl feature (1014) from sawteeth (1006). In addition, the downward movement of ratcheting block (1010) results in camming interaction between cam features (1016, 1022). This camming interaction drives block latch (1020) proximally until cam feature (1016) moves downwardly past cam feature (1022). As soon as cam feature (1016) passes cam feature (1022), spring (1024) drives block latch (1020) distally such that cam feature (1022) is positioned over an upper shelf (1017) of cam feature (1016). This resulting arrangement prevents ratcheting block (1010) from moving upwardly, such that block latch (1020) effectively locks ratcheting block (1010) in the downward position where pawl feature (1014) is disengaged from sawteeth (1006). This lock is maintained even after pushbutton (1030) is released as shown in FIG. 21D. It should be understood that, at this stage, the only thing maintaining the longitudinal position of plunger actuator (1000) relative to housing (960) is the user's grip on grip features (962, 964, 1002).

Figure 21E:
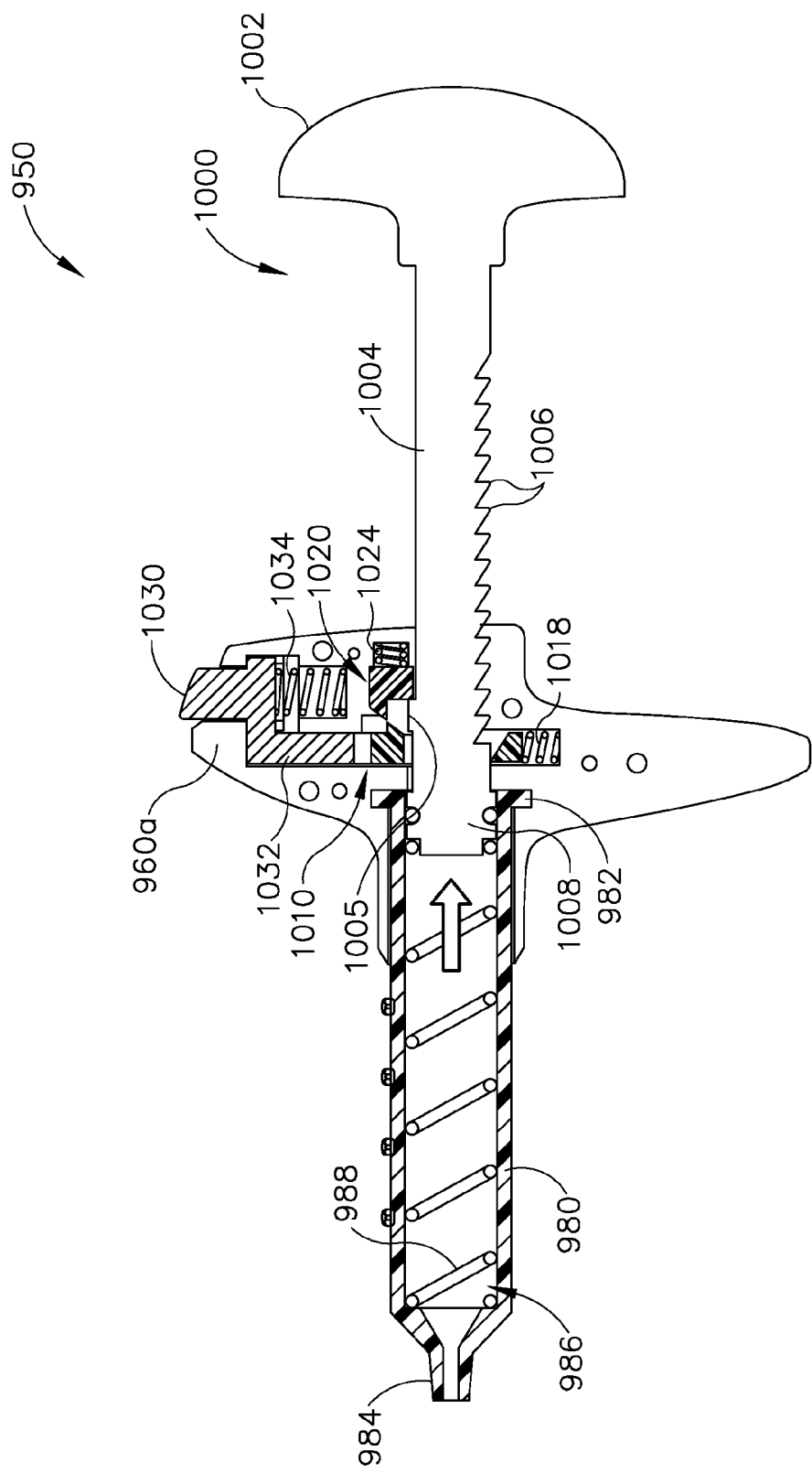
FIG. 21E depicts a cross-sectional side view of the inflator of FIG. 18, with the plunger in a proximal position, and with a latch disengagement feature of the plunger driver disengaging the latch from the ratchet block.

When the user relaxes their grip on grip features (962, 964, 1002), spring (988) drives plunger actuator (1000) proximally, as shown in the transition from FIG. 21D to FIG. 21E. Once plunger actuator (1000) reaches the proximal position shown in FIG. 21E, latch engagement feature (1005) drives block latch (1020) proximally, which disengages cam feature (1022) from upper shelf (1017) of cam feature (1016). This disengagement of cam feature (1016) enables spring (1018) to drive ratcheting block (1010) upwardly. In some versions, ratcheting block (1010) does not actually travel upwardly until the user advances plunger actuator (1000) distally just enough to enable pawl feature (1014) to seat within a valley preceding the first sawtooth (1006), as shown in FIG. 21A. The above components may be configured such that block latch (1020) does not travel distally (under the influence of spring (1024)) enough to engage ratcheting block (1010) until ratcheting block has first traveled upwardly far enough for upper shelf (1017) to clear cam feature (1022). In other words, block latch (1020) does not impede upward movement of ratcheting block (1010) during the transition from the arrangement shown in FIG. 21E back to the arrangement shown in FIG. 21A.

In an exemplary use of inflator (950), a user may start with plunger actuator (1000) advanced to a distal position as shown in FIG. 21B. The user may then position port (984) in a bowl or other container of saline to draw fluid from. In instances where port (984) is coupled with one end of conduit (60), the user may position the other end of conduit (60) in the saline. In either case, the user may then depress pushbutton (1030) to disengage ratcheting block (1010) from shaft (1040) as shown in FIG. 21C. While maintaining a grip on grip features (962, 964, 1002), the user may release pushbutton (1030) as shown in FIG. 21D. Next, the user may relax their grip on grip features (962, 964, 1002), allowing spring (988) to drive plunger actuator (1000) proximally toward the position shown in FIG. 21E. This will in turn translate piston (1008) proximally within syringe barrel (980), thereby drawing the saline (or other fluid) into reservoir (986). The user may then remove port (984) or conduit (60) from the saline container.

At this stage, the user may advance plunger actuator (1000) distally in order to purge air from reservoir (986). For instance, the user may orient inflator (950) such that port (984) is positioned upwardly to gather air at the top of reservoir (986) before squeezing on grip features (962, 964, 1002) to advance plunger actuator (1000) distally in order to purge air from reservoir (986). As the user advances plunger actuator (1000) distally, pawl feature (1014) will ratchet along sawteeth (1006) to prevent plunger actuator (1000) from retracting proximally if and when the user relaxes their grip on grip features (962, 964, 1002).

Once reservoir (986) has been sufficiently filled with fluid and air has been purged, the user may couple inflator (950) with dilation catheter (10), such as by coupling port (984) with side arm Luer connector (22) via a flexible conduit (60). In some instances, a conventional fluid pressure gauge (not shown) may be coupled in the fluid path between port (984) and side arm Luer connector (22) (e.g., via a "T" fitting, etc.). Of course, inflator (950) may alternatively include an integral pressure gauge. With dilator (14) being suitably positioned within an anatomical passageway (e.g., a sinus ostium (SO), etc.), the user may then advance plunger actuator (1000) distally relative to housing (960) to advance piston (1008) within syringe barrel (980), thereby transferring fluid from reservoir (986) to dilator (14). The user may observe the pressure reading at the pressure gauge while advancing plunger actuator (1000) distally in order to determine when the appropriate fluid pressure level has been reached. Again, pawl feature (1014) will ratchet along sawteeth (1006) as the user advances plunger actuator (1000) distally, to prevent plunger actuator (1000) from retracting proximally if and when the user relaxes their grip on grip features (962, 964, 1002).

Once the user has attained the desired level of pressure in dilator (14) within the anatomical passageway to dilate the anatomical passageway, the user may pause for an approximate, predetermined period of time (e.g., approximately three seconds, etc.). The user may then depress pushbutton (1030) to once again disengage ratcheting block (1010) from sawteeth (1006), then relax their grip on grip features (962, 964, 1002). This will allow spring (988) to drive plunger actuator (1000) proximally, thereby drawing fluid from dilator (14) back into reservoir (986). With dilator (14) now deflated, dilator (14) may be retracted from the patient. Alternatively, if the user wishes to dilate additional anatomical passageways, dilator (14) may be positioned in the next anatomical passageway, and the user may repeat the above steps to dilate that next anatomical passageway. Thus, the same volume of fluid within reservoir (986) may be used repeatedly to dilate a plurality of anatomical passageways, without having to withdraw dilator (14) from the patient, and without having to decouple inflator (950) from the rest of system (1), until all of the desired dilations have been completed. Other suitable variations of inflator (950) will be apparent to those of ordinary skill in the art in view of the teachings herein. Similarly, other suitable ways in which inflator (950) may be used will be apparent to those of ordinary skill in the art in view of the teachings herein.

10. Exemplary Alternative Inflator with Ratcheting Drive and Thumbring Release FIGS. 22-27C depict another exemplary inflator (1050). Inflator (1050) of this example includes a housing (1060), a syringe barrel (1080), and a plunger actuator assembly (1100). Housing (1060) of this example is formed as a single piece that defines a pair of upper finger grip features (1062) and a pair of lower finger grip features (1064). During use of inflator (1050), a user may place their index finger between the upper grip features (1062) and their other three fingers between the lower finger grip features (1064). The proximal end of plunger actuator assembly (1100) defines a thumb ring (1102). Grip features (1062, 1064) and thumb ring (1102) are configured to enable a user to grasp and manipulate inflator (1050) with a single hand by engaging their fingers with finger grip features (1062, 1064) and inserting their thumb of the same hand through thumb ring (1102). As will be described in greater detail below, inflator (1050) may be selectively actuated by the user advancing their thumb distally to drive plunger actuator assembly (1100) distally relative to housing (1060); or by retracting their thumb proximally to pull plunger actuator assembly (1100) proximally relative to housing (1060).

Figure 22:
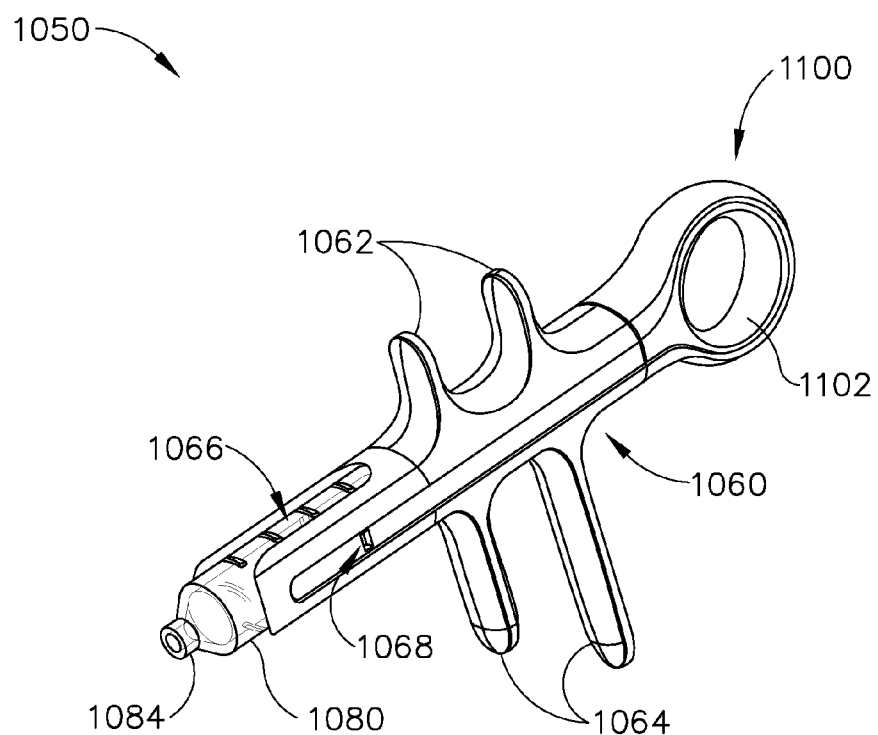
FIG. 22 depicts a perspective view of another exemplary inflator.
Figure 23:
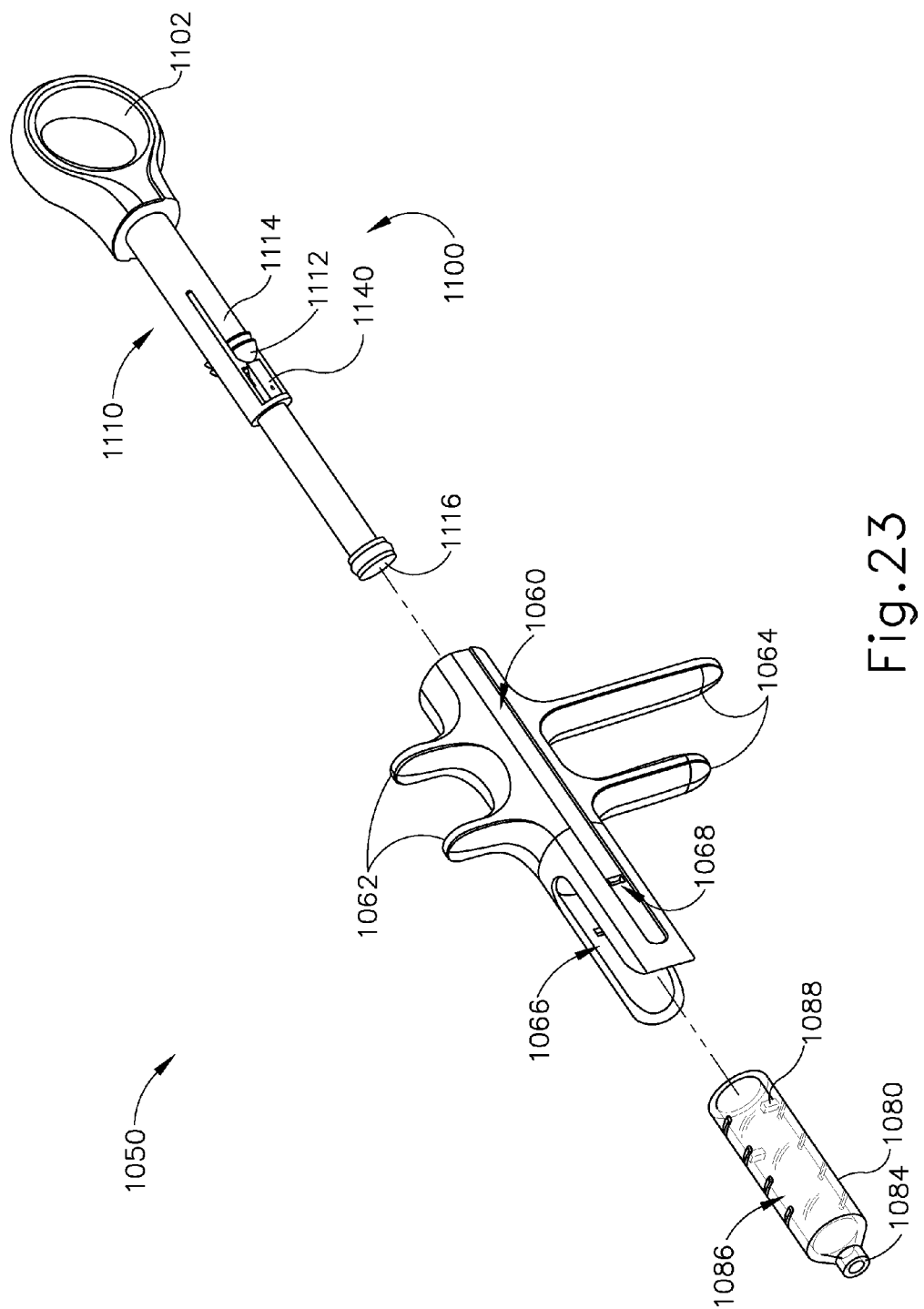
FIG. 23 depicts an exploded view of the inflator of FIG. 23.
Figure 24:
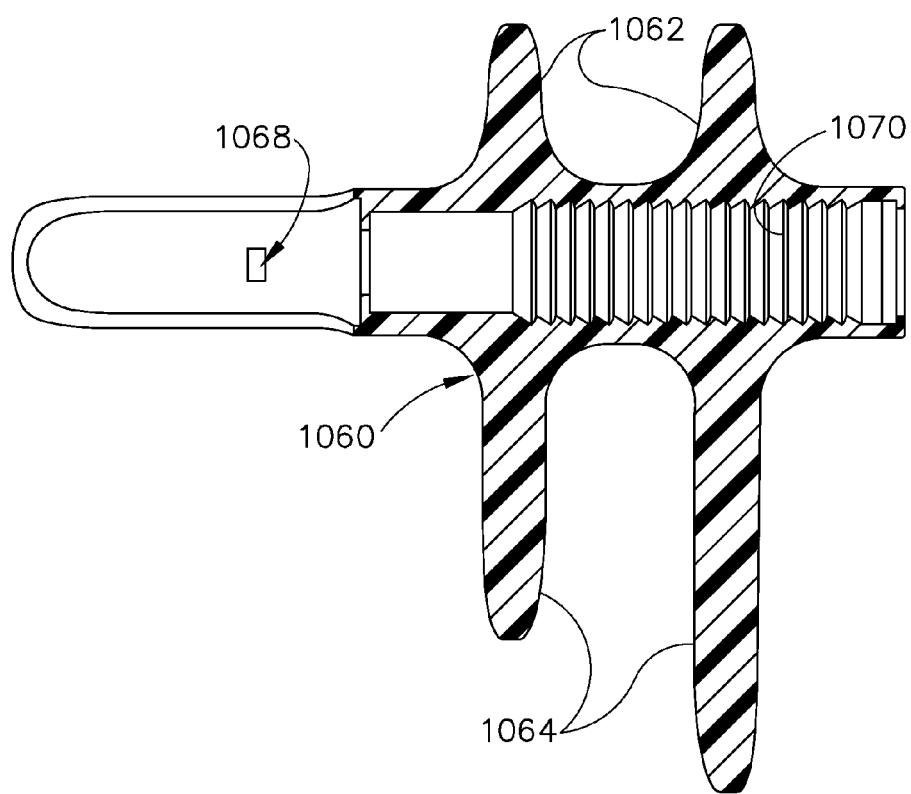
FIG. 24 depicts a cross-sectional side view of the housing of the inflator of FIG. 23.

As best seen in FIGS. 22-23, housing (1060) of the present example defines a pair of notches (1068) that are configured to receive complementary tabs (1088) of syringe barrel (1080) to provide a secure snap-fit engagement between housing (1060) and syringe barrel (1080). Housing (1060) also defines a syringe barrel viewing recess (1066) that permits visualization of the amount of fluid within syringe barrel (1080) during use of inflator (1050). As best seen in FIG. 24, the interior of housing (1060) includes a longitudinal array of annular interior ribs (1070). Ribs (1070) each have a sawtooth profile. Other suitable features and configurations for housing (1060) will be apparent to those of ordinary skill in the art in view of the teachings herein.

Figure 25:
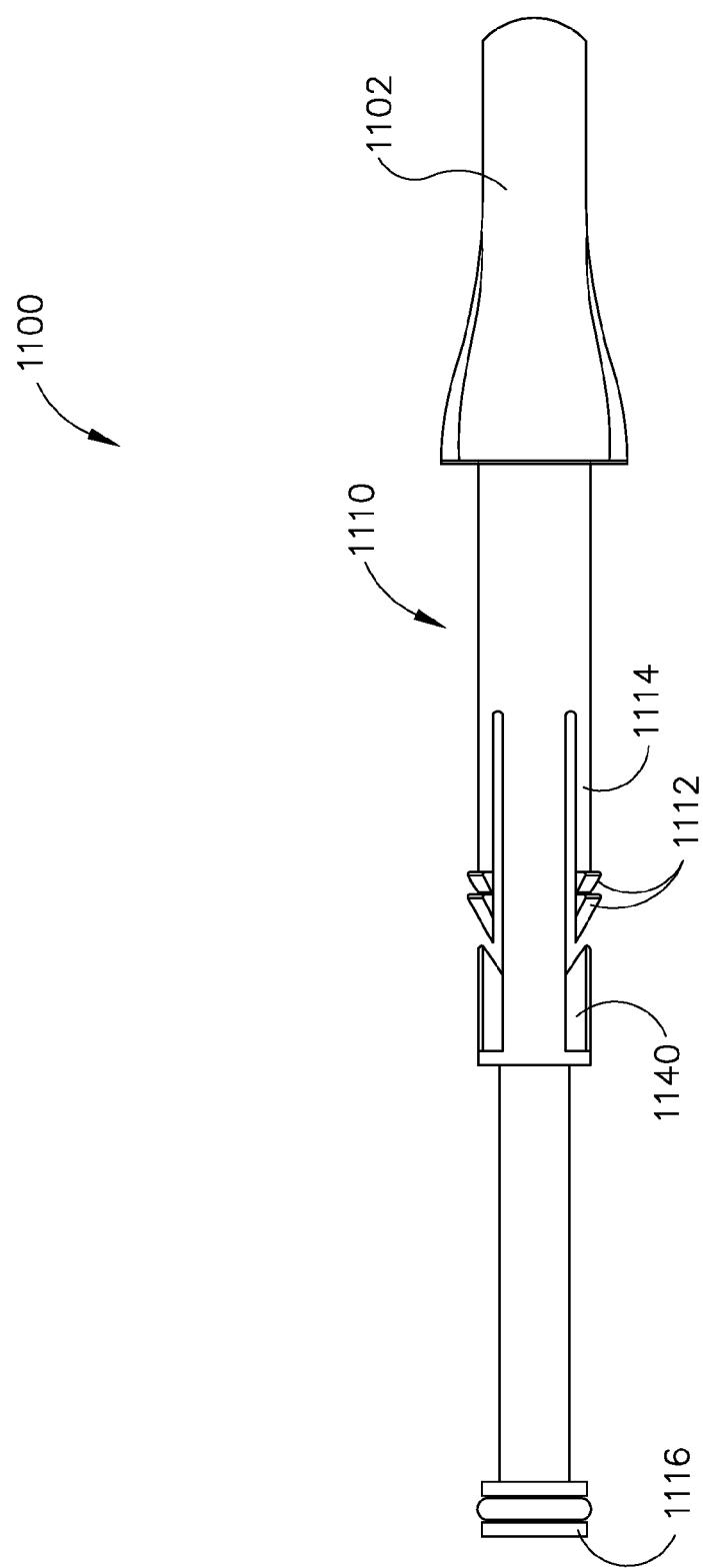
FIG. 25 depicts a top plan view of the plunger actuation assembly of the inflator of FIG. 23.
Figure 26:
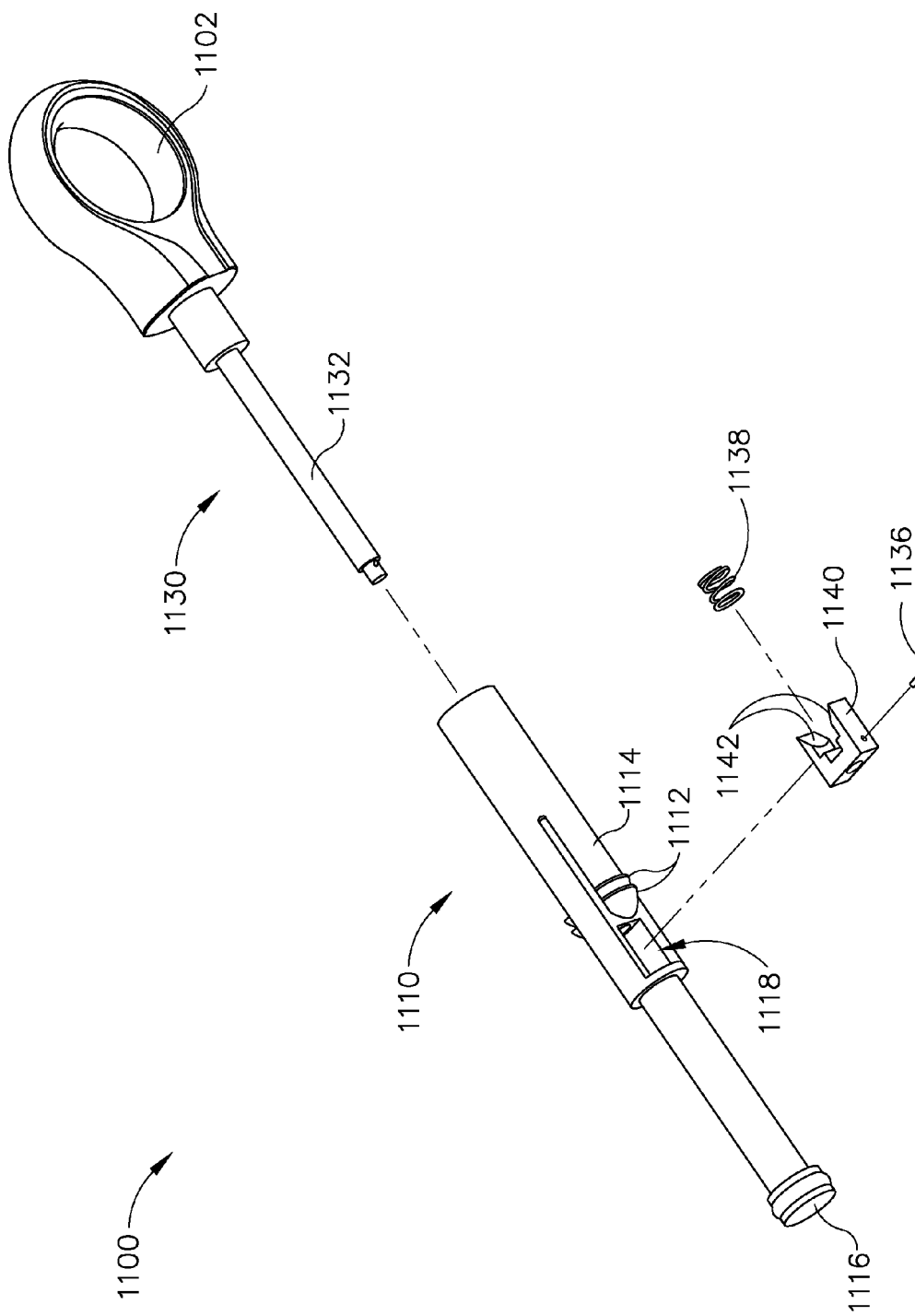
FIG. 26 depicts an exploded view of the plunger actuation assembly of FIG. 25.

As best seen in FIGS. 25-26, plunger actuator assembly (1100) of the present example comprises a plunger driver (1110) and a cam driver (1130). Plunger driver includes a pair of lateral ratchet features (1112) positioned at the distal ends of respective resilient arms (1114). Resilient arms (1114) extend parallel to the longitudinal axis defined by plunger driver (1110), yet are capable of deflecting inwardly toward the longitudinal axis defined by plunger driver (1110) as will be described in greater detail below. The distal end of plunger driver (1110) includes a piston (1116), which is positioned within syringe barrel (1080). Plunger actuator assembly (1100) is operable to translate relative to housing (1060), to thereby reciprocate piston (1116) within syringe barrel (1080). It should be understood that such reciprocation will selectively vary the volume of reservoir (1086) in syringe barrel (1080), to thereby draw fluid into or expel fluid from reservoir (1086).

Cam driver (1130) includes a rod (1132) that is integral with thumb ring (1102). Rod (1132) is slidably disposed within a bore in plunger driver (1110), such that cam driver (1130) and plunger driver (1110) are coaxially aligned. A cam feature (1140) is secured to the distal end of rod (1132) by a pin (1136). Cam feature (1140) is positioned within a transverse channel (1118) of plunger driver (1110) and projects laterally from channel (1118). Cam feature (1140) includes a pair of proximally presented cam surfaces (1142) that are positioned to selectively engage of lateral ratchet features (1112) of plunger driver (1110) as will be described in greater detail below. A spring (1138) is positioned about rod (1132) and is configured to bias cam driver (1130) distally relative to plunger driver (1110). While spring (1138) comprises a coil spring in the present example, any other suitable type of resilient member may be used. Furthermore, spring (1138) may be positioned elsewhere in inflator (1050).

Figure 27A:
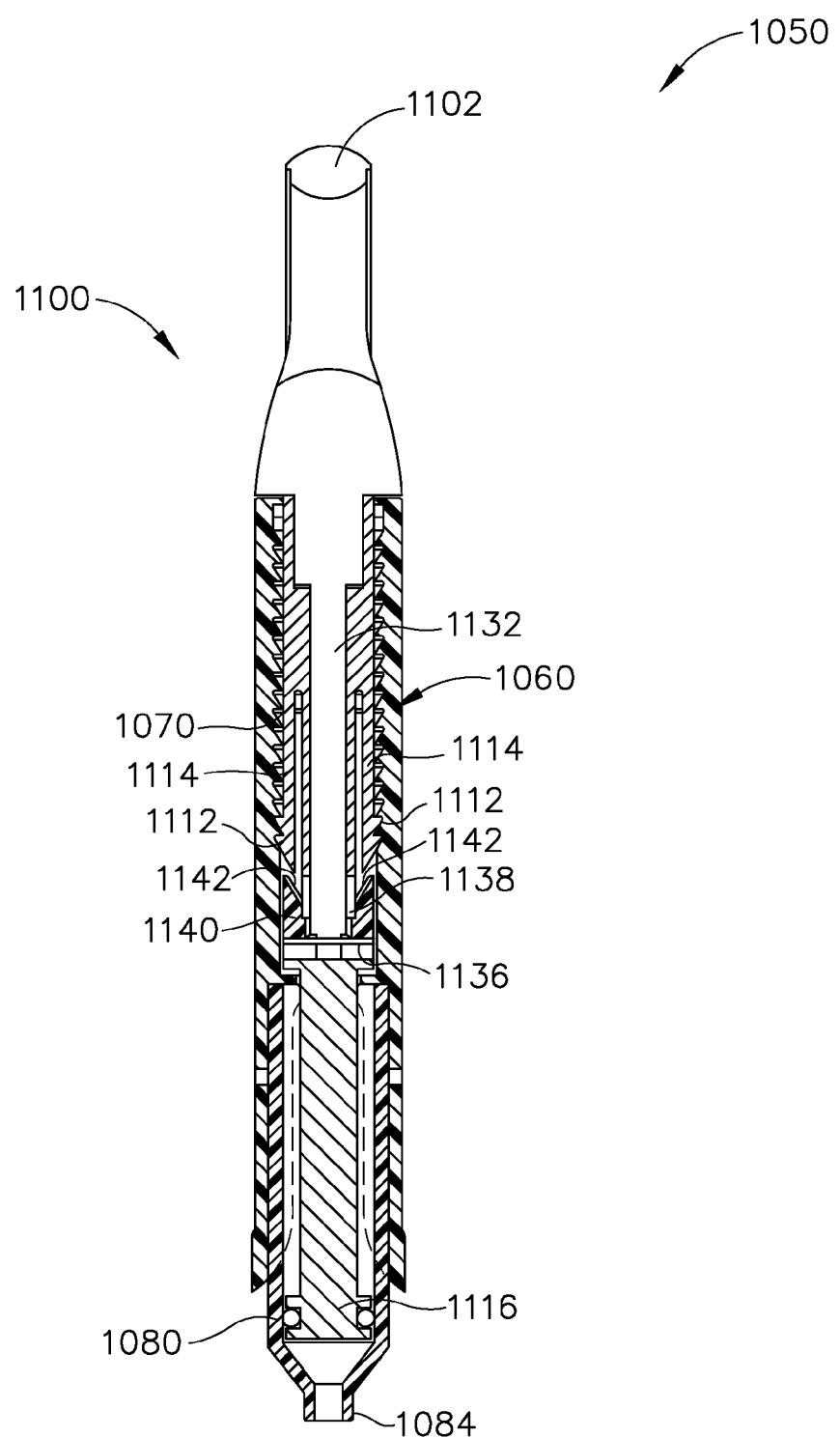
FIG. 27A depicts a cross-sectional top view of the inflator of FIG. 23, with the plunger in a distal position and with the plunger actuation assembly in a locked configuration.
Figure 27B:
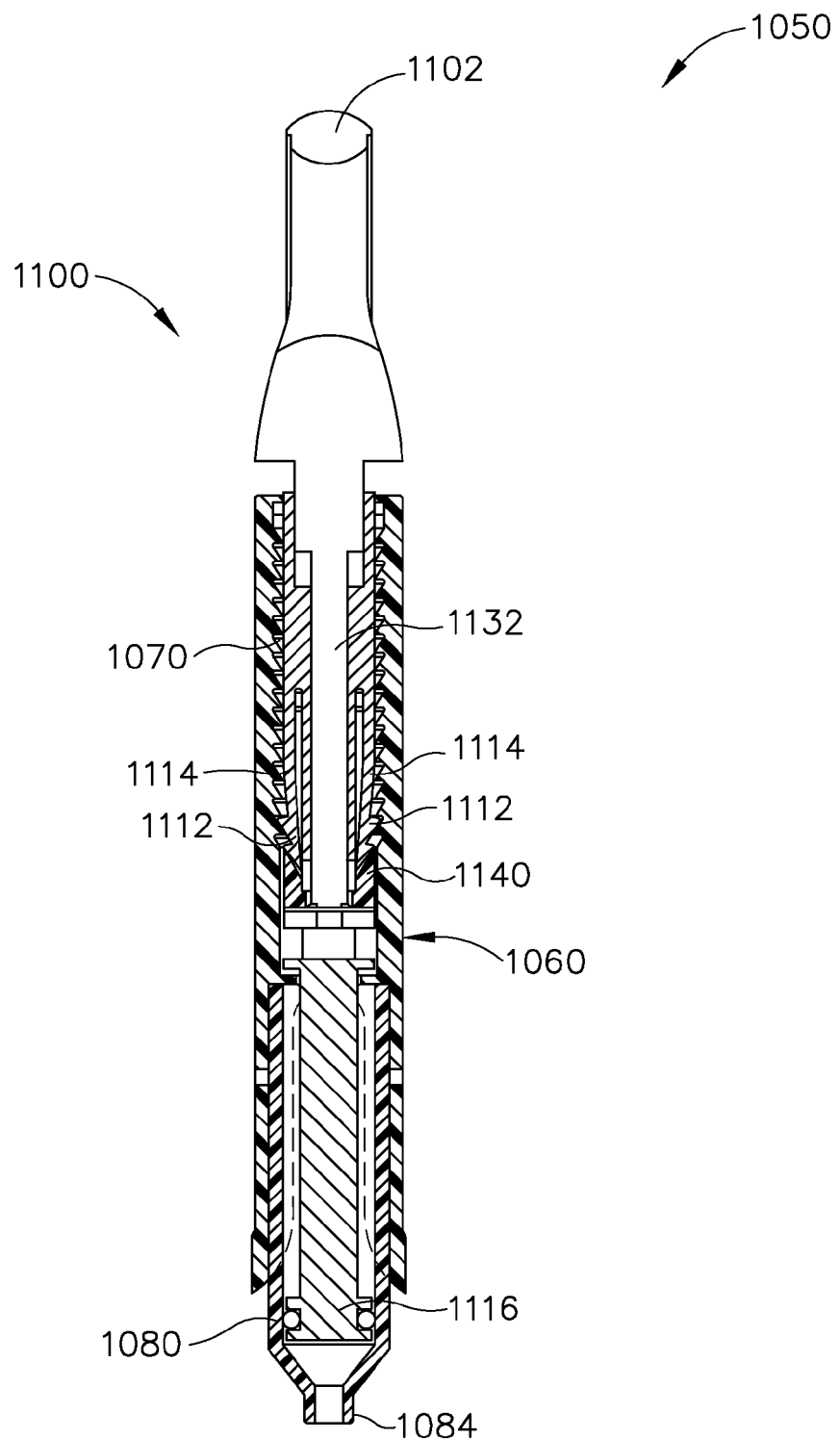
FIG. 27B depicts a cross-sectional top view of the inflator of FIG. 23, with the plunger in a distal position and with the plunger actuation assembly in an unlocked configuration.
Figure 27C:
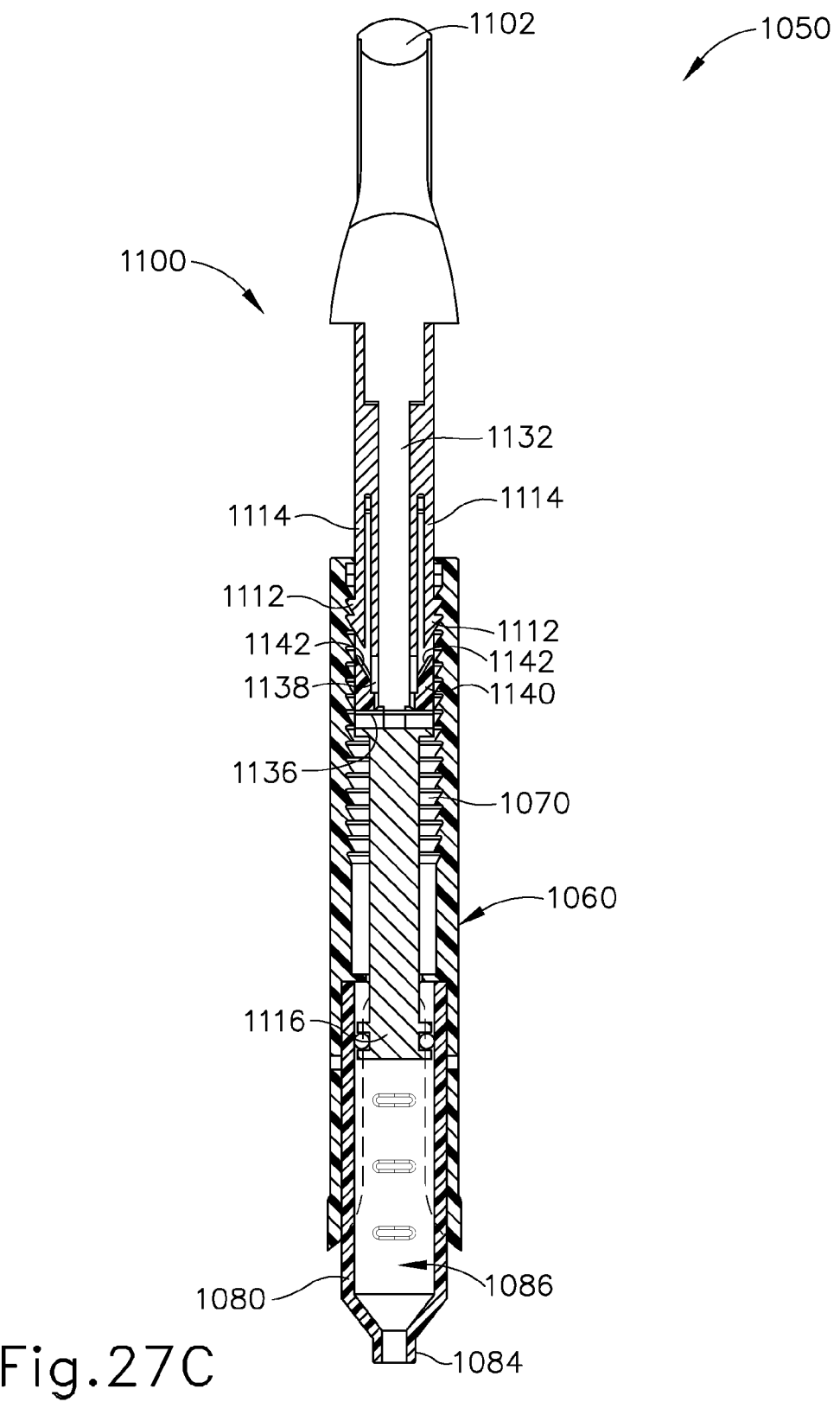
FIG. 27C depicts a cross-sectional top view of the inflator of FIG. 23, with the plunger in a proximal position and with the plunger actuation assembly in a locked configuration.

FIGS. 27A-27C depict a series showing interactions between the above-described components during operation of inflator (1050). In particular, FIG. 27A shows plunger actuation assembly (1100) in a distal position. Lateral ratchet features (1112) are engaged with ribs (1070) of housing (1060), preventing plunger driver (1110) from translating proximally relative to housing (1060). When the user pulls proximally on thumb ring (1102), this translates cam driver (1130) proximally relative to plunger driver (1100), which remains longitudinally fixed relative to housing (1060). As shown in FIG. 27B, this retraction of cam driver (1130) drives cam feature (1140) into lateral ratchet features (1112). Cam surfaces (1142) drive lateral ratchet features (1112) inwardly, causing arms (1114) to bend. This disengages ratchet features (1112) from ribs (1070). With ratchet features (1112) disengaged from ribs (1070), plunger driver (1110) is free to translate proximally relative to housing (1060) as the user continues to pull proximally on thumb ring (1102). Once plunger driver (1110) reaches a proximal position as shown in FIG. 27C, the user may substantially release thumb ring (1102). This will enable spring (1138) to drive cam driver (1130) distally relative to plunger driver (1110). With cam driver (1130) driven distally relative to plunger driver (1110), cam feature (1140) disengages ratchet features (1112), which deflect back outwardly under the resilient bias of arms (1114). The outwardly deflected ratchet features (1112) once again engage ribs (1070). As plunger actuator assembly (1100) is thereafter advanced distally relative to housing (1060), ratchet features (1112) ratchet along ribs (1070) and prevent plunger driver (1110) from translating proximally when thumb ring (1102) is released.

In an exemplary use of inflator (1050), a user may start with plunger actuator assembly (1100) advanced to a distal position as shown in FIG. 27A. The user may then position port (1084) of syringe barrel (1080) in a bowl or other container of saline to draw fluid from. In instances where port (1084) is coupled with one end of conduit (60), the user may position the other end of conduit (60) in the saline. In either case, the user may then pull thumb ring (1102) proximally to drive cam feature (1140) proximally, to thereby disengage ratchet features (1112) from ribs (1070) as shown in FIG. 27B. The user may continue to pull thumb ring (1102) proximally to retract plunger actuation assembly (1100) proximally toward the position shown in FIG. 27C. This will in turn translate piston (1116) proximally within syringe barrel (1080), thereby drawing the saline (or other fluid) into reservoir (1086). The user may then remove port (1084) or conduit (60) from the saline container.

At this stage, the user may advance plunger actuator assembly (1100) distally in order to purge air from reservoir (1086). For instance, the user may orient inflator (1050) such that port (1084) is positioned upwardly to gather air at the top of reservoir (1086) before pushing thumb ring (1102) distally to advance plunger actuator assembly (1100) distally in order to purge air from reservoir (1086). As the user advances plunger actuator assembly (1100) distally, ratchet features (1112) will ratchet along ribs (1070) to prevent plunger actuator (1000) from retracting proximally if and when the user releases thumbring (1102).

Once reservoir (1086) has been sufficiently filled with fluid and air has been purged, the user may couple inflator (1050) with dilation catheter (10), such as by coupling port (1084) with side arm Luer connector (22) via a flexible conduit (60). In some instances, a conventional fluid pressure gauge (not shown) may be coupled in the fluid path between port (1084) and side arm Luer connector (22) (e.g., via a "T" fitting, etc.). Of course, inflator (1050) may alternatively include an integral pressure gauge. With dilator (14) being suitably positioned within an anatomical passageway (e.g., a sinus ostium (SO), etc.), the user may then advance plunger actuator assembly (1100) distally relative to housing (1060) to advance piston (1116) within syringe barrel (1080), thereby transferring fluid from reservoir (1086) to dilator (14). The user may observe the pressure reading at the pressure gauge while advancing plunger actuator assembly (1100) distally in order to determine when the appropriate fluid pressure level has been reached. Again, ratchet features (1112) will ratchet along ribs (1070) as the user advances plunger actuator assembly (1100) distally, to prevent plunger actuator assembly (1100) from retracting proximally if and when the user releases thumb ring (1102).

Once the user has attained the desired level of pressure in dilator (14) within the anatomical passageway to dilate the anatomical passageway, the user may pause for an approximate, predetermined period of time (e.g., approximately three seconds, etc.). The user may then pull thumb ring (1102) proximally to drive cam feature (1140) proximally, to thereby disengage ratchet features (1112) from ribs (1070). This will allow plunger driver (1110) to translate proximally relative to housing (1060). The user may continue to pull thumb ring (1102) proximally to retract plunger actuation assembly (1100) proximally toward the position shown in FIG. 27C. This will in turn translate piston (1116) proximally within syringe barrel (1080), thereby drawing the saline (or other fluid) from dilator (14) back into reservoir (1086). With dilator (14) now deflated, dilator (14) may be retracted from the patient. Alternatively, if the user wishes to dilate additional anatomical passageways, dilator (14) may be positioned in the next anatomical passageway, and the user may repeat the above steps to dilate that next anatomical passageway. Thus, the same volume of fluid within reservoir (1086) may be used repeatedly to dilate a plurality of anatomical passageways, without having to withdraw dilator (14) from the patient, and without having to decouple inflator (1050) from the rest of system (1), until all of the desired dilations have been completed. Other suitable variations of inflator (1050) will be apparent to those of ordinary skill in the art in view of the teachings herein. Similarly, other suitable ways in which inflator (1050) may be used will be apparent to those of ordinary skill in the art in view of the teachings herein.

II. Exemplary Method of Use of the System

While the above discussion of inflators (50, 150, 250, 350, 450, 550, 650, 750, 850, 950, 1050) includes discussion of how each particular inflator (50, 150, 250, 350, 450, 550, 650, 750, 850, 950, 1050) may be used with system (1), the below discussion provides additional examples of how system (1) may be used regardless of which inflator (50, 150, 250, 350, 450, 550, 650, 750, 850, 950, 1050) is being incorporated into system (1). It should be understood that system (1) is capable of many other uses. Similarly, each inflator (50, 150, 250, 350, 450, 550, 650, 750, 850, 950, 1050) may be used in system (1) in ways that are different from the examples described herein. Various other suitable ways in which system (1) and inflators (50, 150, 250, 350, 450, 550, 650, 750, 850, 950, 1050) may be used will be apparent to those of ordinary skill in the art in view of the teachings herein.

In an exemplary use of system (1), dilation catheter (10) is prepared for use separately from the guide catheter (70). Guide catheter (70) is initially inserted into the nose of the patient (along with an endoscope) and is advanced to a position that is within or near the ostium to be dilated. An endoscope is used to view the advancement and positioning of guide catheter (70), and fluoroscopy may also be used to verify that guide catheter (70) is properly positioned near or within the ostium. After guide catheter (70) has been positioned, the operator may insert the distal end of the guidewire into the proximal end of guide catheter (70) and may advance the guidewire (GW) through guide catheter (70) such that a distal portion of the guidewire (GW) passes through the sinus ostium (SO) and becomes coiled within the sinus cavity. Fluoroscopy (or any other suitable technique) may be used to verify that the guidewire has become coiled within the intended sinus cavity.

Dilation catheter (10) may be loaded for use. Dilation catheter (10) may be disconnected from dilator (14) such that the distal end of shaft (12) is free, while the proximal end of dilation catheter (10) is coupled to inflator (50, 150, 250, 350, 450, 550, 650, 750, 850, 950, 1050). The distal end of shaft (12) may be placed in saline. Plunger (167, 267, 367, 467, 567, 667, 767) or piston (944, 1008, 1116) of inflator (50, 150, 250, 350, 450, 550, 650, 750, 850, 950, 1050) may be positioned at a distal position (position A in FIG. 7). Inflator (50, 150, 250, 350, 450, 550, 650, 750, 850, 950, 1050) may be actuated to move plunger (167, 267, 367, 467, 567, 667, 767) or piston (944, 1008, 1116) to a proximal position. As plunger (167, 267, 367, 467, 567, 667, 767) or piston (944, 1008, 1116) moves from a distal position to a proximal position, a vacuum is created to pull water into reservoir (168, 268, 368, 468, 568, 668, 768, 886, 986, 1086). Inflator (50, 150, 250, 350, 450, 550, 650, 750, 850, 950, 1050) may then be actuated to move plunger (167, 267, 367, 467, 567, 667, 767) or piston (944, 1008, 1116) to an intermediate or slightly distal position to purge any air from reservoir (168, 268, 368, 468, 568, 668, 768, 886, 986, 1086). Indicators may be used on inflator (50, 150, 250, 350, 450, 550, 650, 750, 850, 950, 1050) to indicate when plunger (167, 267, 367, 467, 567, 667, 767) or piston (944, 1008, 1116) has reached a desired position (e.g., detents, tactile feedback, etc.). Dilation catheter (10) may then be coupled to dilator (14).

Thereafter, the proximal end of the guidewire (GW) is inserted into the distal end of dilation catheter (10), and dilation catheter (10) (with dilator (14) in a non-expanded state) is advanced over the guidewire and through guide catheter (70) to a position where dilator (14) is positioned within the sinus ostium (SO), or other targeted anatomical passageway. The endoscope may be used to view the advancement and positioning of dilation catheter (10). Although the distal portion of dilator (14) may be within the sinus and out of the field of view of endoscope, endoscope may be used to view the proximal end of dilator (14) and/or optional marker (19) (if present) on the proximal end of dilator (14). Fluoroscopy may be used to image radiographic markers (40, 42) and the ostium to confirm that mid-region (44) of dilator (14) is positioned within the ostium.

After dilator (14) has been positioned within the ostium, dilator (14) may be inflated, thereby dilating the ostium. To inflate dilator (14), inflator (50, 150, 250, 350, 450, 550, 650, 750, 850, 950, 1050) may be actuated to move plunger (167, 267, 367, 467, 567, 667, 767) or piston (944, 1008, 1116) from the intermediate or slightly distal position to the distal position. As plunger (167, 267, 367, 467, 567, 667, 767) or piston (944, 1008, 1116) moves distally, saline in reservoir (168, 268, 368, 468, 568, 668, 768, 886, 986, 1086) may be pushed through dilation catheter (10) into dilator (14). Dilator (14) may be inflated to a volume size to achieve about 10 to about 12 atmospheres. Dilator (14) may be held at this volume for a few seconds to sufficiently open the ostium or targeted anatomical passageway. Dilator (14) may then be deflated (or returned to a non-expanded state) by actuating inflator (50, 150, 250, 350, 450, 550, 650, 750, 850, 950, 1050) to bring plunger (167, 267, 367, 467, 567, 667, 767) or piston (944, 1008, 1116) back to the intermediate or slightly distal position. Dilator (14) may be repeatedly inflated and deflated in different ostia and/or other targeted anatomical passageways. The successful dilation of the ostium may be confirmed visually using an endoscope and/or radiographically using a fluoroscope. Thereafter, dilation catheter (10), guidewire (GW), and guide catheter (70) may be removed from the patient.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the present invention have application in conventional endoscopic and open surgical instrumentation as well as application in robotic-assisted surgery. An exemplary robotic-assist surgery systems is disclosed in U.S. Pat. No. 6,783,524, entitled "Robotic Surgical Tool with Ultrasound Cauterizing and Cutting Instrument," published Aug. 31, 2004, the disclosure of which is incorporated by reference herein.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body, wherein the body includes a first locking feature, wherein the first locking feature comprises a helical groove defined by the body;
   (b) a plunger slidably disposed in the body, wherein the plunger and body cooperate to define a fluid capacity, wherein the plunger is movable relative to the body to vary the fluid capacity, wherein the plunger is rotatable relative to the body to selectively vary the fluid capacity;
   (c) a second locking feature secured to the plunger, wherein the second locking feature is configured to selectively engage the first locking feature to selectively maintain a position of the plunger at a selected one of a plurality of discrete positions in relation to the body, wherein the second locking feature comprises a ball configured to selectively engage the helical groove, wherein the ball is configured to travel linearly along a path that is transverse to a longitudinal axis defined by the plunger to selectively engage the helical groove; and
   (d) a translating member comprising an actuator, wherein the translating member is configured to translate relative to the plunger from a first position to a second position in response to manual actuation of the actuator, wherein the translating member is configured to translate relative to the plunger to selectively engage and disengage the ball with the helical groove, wherein the translating member is resilient biased to drive the ball into engagement with the helical groove;
   wherein the first and second locking features are configured to engage each other in response to the translating member transitioning from the first position to the second position.

2. The apparatus of claim 1, wherein the body defines a handpiece.

3. The apparatus of claim 2, wherein the body further comprises a syringe body disposed within the handpiece, wherein the plunger is inserted in the syringe body.

4. The apparatus of claim 1, wherein the translating member defines a lateral recess configured to receive the ball when the ball is disengaged from the helical groove.

* * * * *

UNITED STATES PATENT AND TRADEMARK OFFICE
CERTIFICATE OF CORRECTION

Page 1 of 1

PATENT NO. : 9,962,531 B2
APPLICATION NO. : 13/837577
DATED : May 8, 2018
INVENTOR(S) : Johnson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 985 days.

Signed and Sealed this
Fourth Day of September, 2018

Andrei Iancu
*Director of the United States Patent and Trademark Office*